US010357513B2

(12) United States Patent
Braithwaite et al.

(10) Patent No.: US 10,357,513 B2
(45) Date of Patent: Jul. 23, 2019

(54) DOSING REGIMEN FOR TREATMENT OF COGNITIVE AND MOTOR IMPAIRMENTS WITH BLOOD PLASMA AND BLOOD PLASMA PRODUCTS

(71) Applicant: Alkahest, Inc., San Carlos, CA (US)

(72) Inventors: Steven P. Braithwaite, Redwood City, CA (US); Eva Czirr, Foster City, CA (US); Ian Gallager, Half Moon Bay, CA (US); Nina Huber, Redwood City, CA (US); S. Sakura Minami, San Francisco, CA (US)

(73) Assignee: Alkahest, Inc., San Carlos, CA (US)

( * ) Notice: Subject to any disclaimer, the term of this patent is extended or adjusted under 35 U.S.C. 154(b) by 0 days.

(21) Appl. No.: 15/961,618

(22) Filed: Apr. 24, 2018

(65) Prior Publication Data
US 2018/0311280 A1 Nov. 1, 2018

Related U.S. Application Data

(60) Provisional application No. 62/490,519, filed on Apr. 26, 2017, provisional application No. 62/584,571, filed on Nov. 10, 2017, provisional application No. 62/623,468, filed on Jan. 29, 2018, provisional application No. 62/641,194, filed on Mar. 9, 2018.

(51) Int. Cl.
| *A61K 35/14* | (2015.01) |
| *A61K 35/16* | (2015.01) |
| *A61P 25/28* | (2006.01) |
| *A61K 9/00* | (2006.01) |
| *A61K 38/17* | (2006.01) |
| *A61K 38/01* | (2006.01) |

(52) U.S. Cl.
CPC ............ *A61K 35/16* (2013.01); *A61K 9/0026* (2013.01); *A61K 38/017* (2013.01); *A61K 38/1722* (2013.01); *A61P 25/28* (2018.01)

(58) Field of Classification Search
None
See application file for complete search history.

(56) References Cited

U.S. PATENT DOCUMENTS

| 4,900,720 | A | 2/1990 | Kotitschke |
| 5,916,202 | A | 6/1999 | Haswell |
| 6,632,174 | B1 | 10/2003 | Breznitz |
| 6,946,546 | B2 | 9/2005 | Vaughan et al. |
| 7,785,601 | B2 | 8/2010 | Schaebitz et al. |
| 7,851,446 | B2 | 12/2010 | Roura |
| 2002/0143283 | A1 | 10/2002 | Braverman et al. |
| 2002/0151064 | A1 | 10/2002 | Rothenberg et al. |
| 2003/0157687 | A1 | 8/2003 | Greene et al. |
| 2004/0120937 | A1 | 6/2004 | Wilson |
| 2004/0127445 | A1 | 7/2004 | Liew et al. |
| 2004/0141946 | A1 | 7/2004 | Schaebitz et al. |
| 2004/0254152 | A1 | 12/2004 | Monje et al. |
| 2005/0221348 | A1 | 10/2005 | Ray et al. |
| 2006/0094064 | A1 | 5/2006 | Ray et al. |
| 2006/0198851 | A1 | 9/2006 | Basi et al. |
| 2006/0263759 | A1 | 11/2006 | Alves-Filho et al. |
| 2007/0037200 | A1 | 2/2007 | Ray et al. |
| 2007/0155725 | A1 | 7/2007 | Li et al. |
| 2007/0190055 | A1 | 8/2007 | Ambati |
| 2008/0026485 | A1 | 1/2008 | Hueber et al. |
| 2008/0057590 | A1 | 3/2008 | Urdea et al. |
| 2009/0111740 | A1 | 4/2009 | Grifols Roura |
| 2009/0143394 | A1 | 6/2009 | Wyss-Coray et al. |
| 2009/0181008 | A1 | 7/2009 | Ray et al. |
| 2009/0239241 | A1 | 9/2009 | Ray et al. |
| 2010/0080850 | A1 | 4/2010 | Hubbel et al. |
| 2010/0124756 | A1 | 5/2010 | Ray et al. |
| 2010/0258496 | A1 | 10/2010 | Hidaka et al. |
| 2010/0310609 | A1 | 12/2010 | Watson et al. |
| 2010/0324079 | A1 | 12/2010 | Ohyagi |
| 2011/0117100 | A1 | 5/2011 | Britschgi et al. |
| 2011/0202284 | A1 | 8/2011 | McReynolds et al. |
| 2011/0212854 | A1 | 9/2011 | Ray et al. |
| 2011/0243947 | A1 | 10/2011 | Doody et al. |
| 2012/0095000 | A1 | 4/2012 | Wyss-Coray et al. |
| 2012/0258075 | A1 | 10/2012 | Wyss-Coray et al. |
| 2013/0040844 | A1 | 2/2013 | Wyss-Coray et al. |
| 2013/0302322 | A1 | 11/2013 | Wong et al. |
| 2014/0011689 | A1 | 1/2014 | Sandip et al. |
| 2014/0121438 | A1 | 6/2014 | Quirk |
| 2014/0255424 | A1 | 9/2014 | Wyss-Coray et al. |
| 2015/0079045 | A1 | 3/2015 | Kong |
| 2015/0157664 | A1 | 6/2015 | Wyss-Coray et al. |
| 2016/0143996 | A1 | 5/2016 | Wyss-Coray et al. |
| 2016/0208011 | A1 | 7/2016 | Wyss-Coray et al. |
| 2017/0081415 | A1 | 3/2017 | Wong et al. |
| 2017/0232118 | A1 | 8/2017 | Wyss-Coray et al. |

FOREIGN PATENT DOCUMENTS

| EP | 19930184040 B1 | 4/1993 |
| EP | 2111868 B1 | 8/2013 |
| RU | 2428997 C1 | 9/2011 |
| RU | 2470677 C1 | 12/2012 |
| UA | 35656 C2 | 4/2001 |
| WO | WO2005052592 A2 | 6/2005 |
| WO | WO2005106492 A2 | 11/2005 |

(Continued)

OTHER PUBLICATIONS

Castellano et al, Human umbilical cord plasma proteins revitalize hippocampal function in aged mice. Nature, (Apr. 27, 2017) vol. 544, No. 7651, pp. 488-492. Electronic Publication Date: Apr. 19, 2017 (Year: 2017).*

(Continued)

*Primary Examiner* — Qiuwen Mi
(74) *Attorney, Agent, or Firm* — Bret E. Field; Bozicevic, Field & Francis LLP

(57) ABSTRACT

Methods and compositions for treating and/or preventing aging-related conditions are described. The compositions used in the methods include blood plasma and blood plasma fractions derived from blood plasma with efficacy in treating and/or preventing aging-related conditions such as cognitive disorders. The methods relate to a regimen of pulsed dosing of blood plasma or blood plasma fractions.

10 Claims, 49 Drawing Sheets

(56) References Cited

FOREIGN PATENT DOCUMENTS

| WO | WO2006133423 A1 | 12/2006 |
| WO | WO2007059135 A2 | 5/2007 |
| WO | WO2009023814 A2 | 2/2009 |
| WO | WO2009055729 A1 | 4/2009 |
| WO | WO2011094535 A2 | 8/2011 |
| WO | WO2013142135 A1 | 9/2013 |
| WO | WO2015088915 A1 | 6/2015 |
| WO | WO2016187217 A2 | 11/2016 |
| WO | WO2016205004 A2 | 12/2016 |
| WO | WO2017120461 A1 | 7/2017 |

OTHER PUBLICATIONS

Baker et al, Aerobic exercise reduces phosphorylated tau protein in cerebrospinal fluid in older adults with mild cognitive impairment. Alzheimer's and Dementia, (Jul. 2015) vol. 11, No. 7, Supp. SUPPL. 1, pp. P324 (Year: 2015).*

Adair et al., "Measurement of gelatinase B (MMP-9) in the cerebrospinal fluid of patients with vascular dementia and Alzheimer disease." Stroke. Jun. 2004;35(6):e159-62.

Adkins et al., "Toward a Human Blood Serum Proteome", (2002) Molecular & Cellular Proteomics 1: 947-955.

Anderson et al., "The Human Plasma Proteome", (2002) Molecular & Cellular Proteomics 1: 845-867.

Anderson et al., "High resolution two-dimensional electrophoresis of human plasma proteins", (1977) Proc. Natl. Acad. Sci. vol. 74, No. 12, pp. 5421-5425.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Bouchard et al., "Aging and brain rejuvenation as systemic events," J. Neurochem. Jan. 2015; 132(1):5-19.

Britschgi et al., "Blood protein signature for the early diagnosis of Alzheimer disease." Arch Neurol. Feb. 2009;66(2):161-5.

Cheung et al., "Serum β-2 microglobulin predicts mortality in people with diabetes." Eur J Endocrinol. May 17, 2013;169(1):1-7.

Fedoroff et al., "Role of colony stimulating factor-1 in brain damage caused by ischemia." Neurosci Biobehav Rev. Mar. 1997;21(2):187-91.

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jha, "Young blood can reverse some effects of ageing, study finds," The Guardian, Oct. 17, 2012, 4 pages.

Kwak et al., "Aging, exercise, and extracellular matrix in the heart." J Exerc Rehabil. Jun. 30, 2013;9(3):338-47.

Lin et al., "Discovery of a cytokine and its receptor by functional screening of the extracellular proteome." Science. May 9, 2008;320(5877):807-11.

Luo et al., "Colony-stimulating factor 1 receptor (CSF1R) signaling in injured neurons facilitates protection and survival." J. Exp. Med. (2013) 210(1):157-172.

Lysaght et al., "Beta-2 microglobulin removal during continuous ambulatory peritoneal dialysis (CAPD)." Perit Dial Int. 1989;9(1):29-35.

Malkki, "Ageing: Could young blood combat age-related cognitive decline?" Nat. Rev. Neurol. Jun. 2014;10(6):307.

Manzo et al., "Role of chemokines and chemokine receptors in regulating specific leukocyte trafficking in the immune/inflammatory response." Clin Exp Rheumatol. Jul.-Aug. 2003;21(4):501-8.

McLaurin et al., "Microglial pilgrimage to the brain." Nat Med. Dec. 2010;16(12):1380-1.

Middeldorp et al., "A young systemic environment reverses degeneration in a mouse model of Alzheimer's disease," Neuroscience 2012, Presentation Abstract, Oct. 16, 2012, 2 pages.

Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.

Mizuno et al., "Interleukin-34 selectively enhances the neuroprotective effects of microglia to attenuate oligomeric amyloid-β neurotoxicity." Am J Pathol. Oct. 2011;179(4):2016-27.

Palop et al., "A network dysfunction perspective on neurodegenerative diseases." Nature. Oct. 19, 2006;443(7113):768-73.

Prakasam et al., "Amyloid and neurodegeneration: Alzheimer's disease and retinal degeneration." Chapter 7, Handbook of Neurochemistry and Molecular Neurobiology, Lajtha ed., 2009, 131-163. (Year: 2009).

Ron-Harel et al., "Age-Dependent Spatial Memory Loss Can Be Partially Restored by Immune Activation," Rejuvenation Resarch (2008), 11(5):903-13.

Royer et al., "A novel antagonist of prostaglandin 02 blocks the locomotion of eosinophils and basophils." Eur J Clin nvesl. Sep. 2008;38(9):663-71.

Schwartz et al., "How Do Immune Cells Support and Shape the Brain in Health, Disease, and Aging?" The Journal of Neuroscience, Nov. 6, 2013, 33(45):17587-96.

Sellebjerg et al., "Identification of new sensitive biomarkers for the in vivo response to interferon-beta treatment in multiple sclerosis using DNA-array evaluation." Eur J Neurol. Dec. 2009;16(12):1291-8.

Shin et al., "Association of eotaxin gene family with asthma and serum total IgE." Hum Mol Genet. Jun. 1, 2003;12(11):1279-85.

Skovronsky et al., "Neurodegenerative diseases: new concepts of pathogenesis and their therapeutic Implications." Annu Rev Pathol. 2006;1:151-70.

Smith et al., "β2-microglobulin is a systemic pro-aging factor that impairs cognitive function and neurogenesis." Nat Med. Aug. 2015;21(8):932-7.

Strobel et al., "Chicago: the vampire principle—young blood rejuvenates aging brain?" Alzheimer Research Forum (Nov. 2009), p. 1-3.

Stubbs et al., "Indomethacin causes prostaglandin 0(2)-like and eotaxin-like selective responses in eosinophils and basophils." J Biol Chem. Jul. 19, 2002;277(29):26012-20.

Teixeira et al., "Increased serum levels of CCL 11/eotaxin in schizophrenia," "Process in neuro-psychopharmacology & biological psychiatry," vol. 32, No. 3, pp. 710-714, 2008.

Thomson et al., "Young blood for a keener mind," New Scientist (2012), 216(2887): 10.

Villeda et al., "Changes in the systemic milieu modulate neurogenesis during aging." Abstract, 39th Annual Neuroscience Meeting, Chicago, IL, Society for Neuroscience, Oct. 2009, 1-2. (Year: 2009).

Villeda et al., "The aging systemic milieu negatively regulates neurogenesis and cognitive function," Nature, Aug. 31, 2011, 477(7362):90-4.

Villeda et al., "Young blood reverses age-related cognitive impairments," Neuroscience 2012, Presentation Abstract, Oct. 17, 2012, 2 pages.

Villeda et al., "Young blood reverses age-related impairments in cognitive function and synaptic plasticity in mice," Nat Med. (Jun. 2014), 20(6):659-63.

Vincent et al., "Macrophage colony stimulating factor prevents NMDA-induced neuronal death in hippocampal organotypic cultures." J Neurochem. Sep. 2002;82(6):1388-97.

Wang et al., "Expression of colony stimulating factor-1 receptor (CSF-1R) by CNS neurons in mice." J Neurosci Res. Sep. 1, 1999;57(5):616-32.

Wang et al., "Matrix metalloproteinases and their multiple roles in Alzheimer's disease." Biomed Res Int. 2014;2014:908636.

Wilson et al., "Beta2-microglobulin as a biomarker in peripheral arterial disease: proteomic profiling and clinical studies." Circulation. Sep. 18, 2007;116(12):1396-403.

(56) References Cited

OTHER PUBLICATIONS

Yagihashi et al., "Macrophage colony stimulating factor (M-CSF) protects spiral ganglion neurons following auditory nerve injury: morphological and functional evidence." Exp Neurol. Mar. 2005;192(1):167-77.

Yamane et al., "CSF-1 receptor-mediated differentiation of a new type of monocytic cell with B cell-stimulating activity: its selective dependence on IL-34." J Leukoc Biol. Jan. 2014;95(1):19-31.

Ye et al., "Haptoglobin-alpha subunit as potential serum biomarker in ovarian cancer: identification and characterization using proteomic profiling and mass spectrometry." Clinical Cancer Research (Aug. 2003), 9(8):2904-11.

Bhattacharya, "Placental umbilical cord whole blood transfusion. A safe and genuine blood substitute for patients of the under-resourced areas of this country at emergency." J Am Coll Surg. 2005. Submitted 34 pages.

Bhattacharya, "Study of the utility of placental cord blood in meeting the transfusion needs of beta-thalassaemic patients." Regional Health Forum, 2008. pp. 16-27.

Borlongan et al., "Central Nervous System Entry of Peripherally Injected Umbilical Cord Blood Cells is Not Required for Neuroprotection in Stroke." Stroke. 2004. pp. 2385-2389. Dallas, Texas.

Conboy et al., "Heterochronic parabiosis for the study of the effects of aging on stem cells and their niches." Cell Cycle. 2012. pp. 2260-2268.

Conboy et al., "Heterochronic parabiosis: Historical perspective and methodological considerations for studies of aging and longevity," Aging Cell, available online Apr. 2013. pp. 525-530.

Conboy et al., "Rejuvination of aged progenitor cells by exposure to a young systemic environment" Nature. 2005. pp. 760-764.

Catcher, "Studies that Shed New Light on Aging." Biochemistry (Moscow), Sep. 2013. pp. 1061-1070.

Loffredo et al., "Growth Differentiation Factor 11 is a Circulating Factor that Reverses Age-Related Cardiac Hypertrophy." Cell. May 2013. pp. 828-839.

Krementsov, "A Martian Stranded on Earth: Alexander Bogdanov, Blood Transfusions, and Proletarian Science." pp. 57-59, 85, 86, and 88. University of Chicago Press, Chicago, United States, 2011.

Boada et al., "Treatment of Alzheimer disease using combination therapy with plasma exchange and haemapheresis with albumin and intravenous immunoglobulin: Rationale and treatment approach of the AMBAR (Alzheimer Management by Albumin Replacement) study." Neurologia, vol. 31, No. 7, pp. 473-481 (Jul. 29, 2016). See abstract; p. 479.

Hughes et al., "Clinical applications of intravenous immunoglobulins in neurology." Clinical and Experimental Immunology, vol. 158, supple.1, pp. 34-42 (2009). See abstract; pp. 38-40.

Website document entitled "Plasma Protein Composition" (available at http://www.sigmaaldrich.com/life-science/metabolomics/enzyme-explorer/learning-center/plasma-blood-proteins/plasma-protein-composition.html). Downloaded on Jun. 27, 2017.

"Young blood can reverse some effects of ageing, study finds," Society for Neuroscience, The Observer, Oct. 24, 2012, 2 pages, Retrieved online: http://gonzoj.wordpress.com/tag/society-for-neuroscience/.

* cited by examiner

Cell survival in Plasma and Plasma Products

Neurogenesis in Plasma and Plasma Products

2x/week

3x/week

Analysis 48h post last dose pulse dosing

Analysis 21 days post last dose

CD68

GFAP

Figure 47A
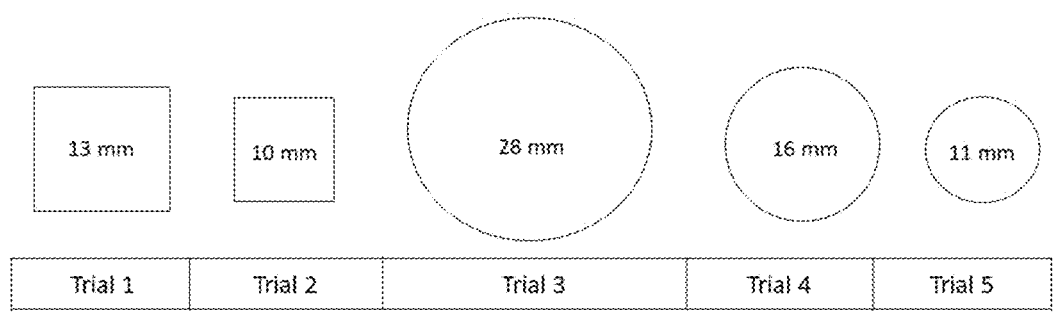
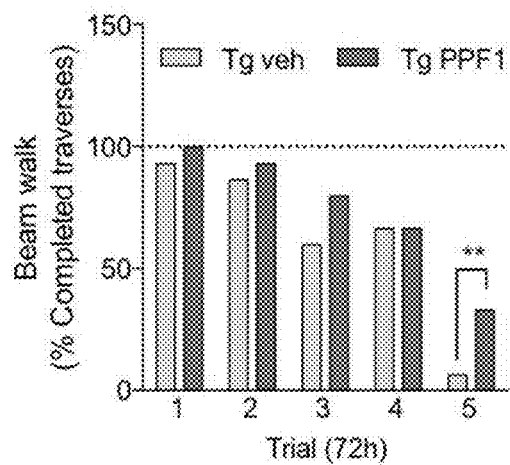
Figure 47B
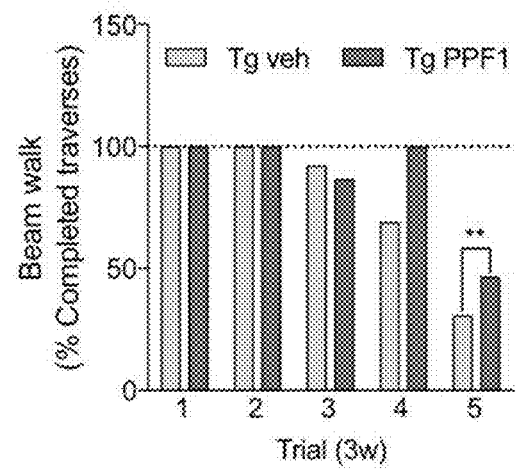
Figure 47C

DOSING REGIMEN FOR TREATMENT OF COGNITIVE AND MOTOR IMPAIRMENTS WITH BLOOD PLASMA AND BLOOD PLASMA PRODUCTS

CROSS-REFERENCE TO RELATED APPLICATIONS

Pursuant to 35 U.S.C. § 119 (e), this application claims priority to the filing dates of: U.S. Provisional Patent Application No. 62/490,519 filed Apr. 26, 2017; U.S. Provisional Patent Application No. 62/584,571 filed Nov. 10, 2017; U.S. Provisional Patent Application No. 62/623,468 filed Jan. 29, 2018; and U.S. Provisional Patent Application No. 62/641,194 filed Mar. 9, 2018; the disclosures of which applications are herein incorporated by reference.

FIELD

This invention pertains to the prevention and treatment of aging-associated disease. The invention relates to the use of blood products, such as blood plasma fractions to treat and/or prevent conditions associated with aging, such as cognitive disorders, motor disorders, and neuroinflammation using various dosing paradigms.

BACKGROUND

The following is offered as background information only and is not admitted as prior art to the present invention.

Aging is an important risk factor for multiple human diseases including cognitive impairment, cancer, arthritis, vision loss, osteoporosis, diabetes, cardiovascular disease, and stroke. In addition to normal synapse loss during natural aging, synapse loss is an early pathological event common to many neurodegenerative conditions and is the best correlate to the neuronal and cognitive impairment associated with these conditions. As such, aging remains the single most dominant risk factor for dementia-related neurodegenerative diseases such as Alzheimer's disease (AD) (Bishop, N. A. et al., *Neural mechanisms of ageing and cognitive decline*. Nature 464(7288), 529-535 (2010); Heeden, T. et al., *Insights into the ageing mind: a view from cognitive neuroscience*. Nat. Rev. Neurosci. 5(2), 87-96 (2004); Mattson, M. P., et al., *Ageing and neuronal vulnerability*. Nat. Rev. Neurosci. 7(4), 278-294 (2006)). Aging affects all tissues and functions of the body including the central nervous system, and neurodegeneration and a decline in functions such as cognition or motor skills, can severely impact quality of life. Treatment for cognitive decline, motor impairment, and neurodegenerative disorders has had limited success in preventing and reversing impairment. It is therefore important to identify new treatments for maintaining cognitive integrity by protecting against, countering, or reversing the effects of aging. Further, when new treatments are developed, dosing paradigms must be investigated to optimize the efficacy of those treatments.

Although parabiosis experiments between old and young mice have shown that cognitive function can be improved in old mice in heterochronic blood exchange with young mice, recent reports find that there is no enhancement of neurogenesis in old mice by one exchange of young blood. (Rebo, J. et al. *A single heterochronic blood exchange reveals rapid inhibition of multiple tissues by old blood*. Nat. Comm (2016)). Further, there is doubt that cognitive function resulting from infusions of young plasma and neurogenesis are linked. Thus, a dosing regimen using blood plasma or blood plasma fractions that stimulates neurogenesis and improved cognitive function had yet to be described.

SUMMARY

The present invention is based on the production and use of blood products for treating and/or preventing age-related disorders, such as cognitive impairment conditions, age-related dementia, impairment of motor function, neuroinflammation, and neurodegenerative disease. The present invention recognizes, among other things, the need for new therapies for the treatment and/or prevention of cognitive impairment, age-related dementia, motor impairment, neuroinflammation, and neurodegenerative disease. Derived from blood and blood plasma, the present compositions of the invention relate to a solution for the failures and shortcomings of current therapies through utilization of blood plasma fractions exhibiting efficacy in the treatment and/or prevention of cognitive impairment, age-related dementia, motor impairment, neuroinflammation, and neurodegenerative disease.

The invention recognizes that blood plasma proteins have an average half-life of 2-3 days. The invention uses a blood plasma or Plasma Fraction dosing regimen that optimizes neurogenesis, cell survival, decline in neuroinflammation, and improved cognition or motor function in the treated subject. The dosing regimen of the invention has been found to trigger all of these processes (neurogenesis, cell survival, improved cognition, decreased neuroinflammation, and improved motor function) in subjects, and the processes have all been found to be active even weeks after the final dose.

An embodiment of the invention includes treating a subject diagnosed with a cognitive impairment by administering to the subject an effective amount of blood plasma or Plasma Fraction. Another embodiment of the invention includes administering the effective amount of blood plasma or Plasma Fraction and subsequently monitoring the subject for improved cognitive function. Another embodiment of the invention includes treating a subject diagnosed with a cognitive impairment by administering to the subject an effective amount of blood plasma or Plasma Fraction wherein the blood plasma or Plasma Fraction is administered in a manner resulting in improved cognitive function or neurogenesis.

An embodiment of the invention includes treating a subject diagnosed with a neurodegenerative motor disorder such as, by way of example and not limitation Parkinson's Disease, by administering to the subject an effective amount of blood plasma or Plasma Fraction. Another embodiment of the invention includes administering the effective amount of blood plasma or Plasma Fraction and subsequently monitoring the subject for improved motor function. Another embodiment of the invention includes treating a subject diagnosed with a neurodegenerative motor disorder by administering to the subject an effective amount of blood plasma or Plasma Fraction wherein the blood plasma or Plasma Fraction is administered in a manner resulting in improved motor function or neurogenesis.

An embodiment of the invention includes treating a subject diagnosed with neuroinflammation or a neuroinflammation-associated disorder by administering to the subject an effective amount of blood plasma or Plasma Fraction. Another embodiment of the invention includes administering the effective amount of blood plasma or Plasma Fraction and subsequently monitoring the subject for reduced neuroinflammation. Another embodiment of the invention includes treating a subject diagnosed with neuroinflammation or a neuroinflammation-associated disorder by administering to the subject an effective amount of blood plasma or Plasma Fraction wherein the blood plasma or Plasma Fraction is administered in a manner resulting in reduced neuroinflammation.

Another embodiment of the invention includes administering the blood plasma or Plasma Fraction via a dosing regimen of at least two consecutive days. A further embodiment of the invention includes administering the blood plasma or Plasma Fraction via a dosing regimen of at least 3, 4, 5, 6, 7, 8, 9, 10, 11, 12, 13, or 14 consecutive days (referred to as "Pulsed Dosing," "Pulsed Dose," "Pulse Dosing," "Pulse Dose," or "Pulse Dosed" herein). Yet another embodiment of the invention includes administering the blood plasma or Plasma Fraction via a dosing regimen of at least 2 consecutive days and after the date of last administration. Another embodiment of the invention includes administering the blood plasma or Plasma Fraction via a dosing regimen of 2 to 14 non-consecutive days wherein each gap between doses may be between 0-3 days each. Another embodiment of the invention includes monitoring the subject for improved cognitive or motor function, decreased neuroinflammation, or improved neurogenesis at least 3 days after the date of last administration. Another embodiment of the invention includes monitoring the subject for improved cognitive or motor function, decreased neuroinflammation, or improved neurogenesis beyond when the average half-life of the proteins in the blood plasma or Plasma Fraction has been reached.

In some instances, Pulsed Dosing in accordance with the invention includes administration of a first set of doses, e.g., as described above, followed by a period of no dosing, e.g., a "dosing-free period", which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

The current invention also recognizes that differences in protein content between different blood plasma fractions (e.g. fractions, effluents, Plasma Protein Fraction, Human Albumin Solution) can be responsible for preventing and/or improving certain cognitive or motor impairments and alleviating neurodegenerative disease. By way of example, and not limitation, embodiments of the current invention demonstrate that mere higher albumin concentration of recombinant human albumin or Human Albumin Solution (HAS) preparations is not the driving force behind improved cognition, improved motor function, reduced neuroinflammation, cell survival, or neurogenesis associated with Plasma Protein Fraction (PPF) preparations with lower albumin concentrations.

Blood and blood plasma from young donors have exhibited improvement and reversal of the pre-existing effects of brain aging, including at the molecular, structural, functional, and cognitive levels. (Saul A. Villeda, et al. *Young blood reverses age-related impairments in cognitive function and synaptic plasticity in mice*. Nature Medicine 20 659-663 (2014)). The present invention relates to fractions and effluents of the blood plasma, some of which have been traditionally used to treat patient shock, and the discovery that they are effective as methods of treatment of aging-associated cognitive impairment, reduced motor function, and neuroinflammation or neurodegenerative-related disease.

In accordance with aspects of the invention, then, methods of treatment of aging-associated cognitive impairment, age-related dementia, motor impairment, neuroinflammation, and/or neurodegenerative disease using blood product fractions of blood plasma are provided. Aspects of the methods include administering a blood plasma fraction to an individual suffering from or at risk of developing aging-associated cognitive impairment, motor impairment, neuroinflammation, or neurodegenerative disease. Additional aspects of the methods include administering a blood plasma fraction derived from a pool of donors of a specific age range to an individual suffering from or at risk of developing aging-associated cognitive impairment, motor impairment, neuroinflammation, or neurodegenerative disease. Further aspects of the methods include administration of blood plasma or Plasma Fractions using a Pulsed Dosing regimen. Also provided are reagents, devices, and kits thereof that find use in practicing the subject methods.

In an embodiment, the blood plasma fraction may be, for example, one of several blood plasma fractions obtained from a blood fractionation process, such as the Cohn fractionation process described below. In another embodiment, the blood plasma fraction may be of the type, herein referred to as "Plasma Fraction," which is a solution comprised of normal human albumin, alpha and beta globulins, gamma globulin, and other proteins, either individually or as complexes. In another embodiment, the blood plasma fraction may be a type of blood plasma fraction known to those having skill in the art as a "Plasma Protein Fraction" (PPF). In another embodiment, the blood plasma fraction may be a "Human Albumin Solution" (HAS) fraction. In yet another embodiment, the blood plasma fraction may be one in which substantially all of the clotting factors are removed in order to retain the efficacy of the fraction with reduced risk of thromboses. Embodiments of the invention may also include administering, for example, a fraction derived from a young donor or pools of young donors. Another embodiment of the invention may include the monitoring of cognitive improvement, improved motor function, decreased neuroinflammation, or increased neurogenesis in a subject treated with a blood plasma fraction.

An embodiment of the invention includes treating a subject diagnosed with a cognitive impairment, neurodegenerative motor impairment, or a neuroinflammation-associated disease by administering to the subject an effective amount of blood plasma or Plasma Fraction. Another embodiment of the invention includes administering the effective amount of blood plasma or Plasma Fraction and subsequently monitoring the subject for improved cognitive function, improved motor function, decreased neuroinflammation, or increased neurogenesis. Another embodiment of the invention includes administering the blood plasma or Plasma Fraction via a dosing regimen of at least two consecutive days and monitoring the subject for improved cognitive function, improved motor function, decreased neuroinflammation, or increased neurogenesis at least 2 days after the date of last administration. A further embodiment of the invention includes administering the blood plasma or Plasma Fraction via a dosing regimen of at least 3, 4, 5, 6, 7, 8, 9, 10, 11, 12, 13, or 14 days and monitoring the subject for improved cognitive function, improved motor function, decreased neuroinflammation, or increased neurogenesis at least 3 days after the date of last administration. Yet another embodiment of the invention includes administering the blood plasma or Plasma Fraction via a dosing regimen of a least 2 consecutive days and after the date of last administration, monitoring for cognitive improvement, improved motor function, decreased neuroinflammation, or increased neurogenesis after the average half-life of the proteins in the blood plasma or Plasma Fraction has been reached.

An embodiment of the invention includes treating a subject diagnosed with a cognitive impairment, impaired motor function, neuroinflammation, or a decline in neurogenesis by administering to the subject an effective amount of blood plasma or Plasma Fraction, with the subject following an exercise regimen after the administration. Another embodiment of the invention includes following an exercise regimen that is prescribed to the subject. Another embodiment of the invention includes the subject exercising at a higher intensity and/or greater frequency than the subject exercised preceding the administration. Another embodiment of the invention includes the subject exercising at a similar intensity and/or frequency as the subject exercised preceding the administration.

An embodiment of the invention includes treating a subject diagnosed with a cognitive impairment, impaired motor function, neuroinflammation, or a decline in neurogenesis by administering to the subject an effective amount of blood plasma or Plasma Fraction in a subject who is undergoing, will undergo, or has received stem cell therapy. Another embodiment of the invention includes administering to a subject an effective amount of blood plasma or Plasma Fraction where the subject is undergoing, will undergo, or has received stem cell therapy, and wherein the stem cells used in the therapy can be embryonic stem cells, non-embryonic stem cells, induced pluripotent stem cells (iPSCs), cord blood stem cells, amniotic fluid stem cells, and the like. Another embodiment of the invention includes treating a subject diagnosed with traumatic spinal cord injury, stroke, retinal disease, Huntington's disease, Parkinson's Disease, Alzheimer's Disease, hearing loss, heart disease, rheumatoid arthritis, or severe burns, and who is undergoing, will undergo, or has received stem cell therapy, with an effective amount of blood plasma or Plasma Fraction.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 47A shows different beam shapes and sizes used in five different beam walk trials of increasing difficulty.

FIG. 47B reports the results of five different beam walk trials in 4 to 4.5-month-old male alpha-synuclein mice (Line 61) (a model for Parkinson's Disease) treated with a seven-consecutive day Pulsed Dosing regimen using PPF1 or vehicle control. The beam walk trials were performed 72 hours after the last treatment dose.

FIG. 47C reports the results of five different beam walk trials in 4 to 4.5-month-old male alpha-synuclein mice (Line 61) (a model for Parkinson's Disease) treated with a seven-consecutive day Pulsed Dosing regimen using PPF1 or vehicle control. The beam walk trials were performed 3 weeks after the last treatment dose.

DETAILED DESCRIPTION

1. Introduction

Figure 1A:
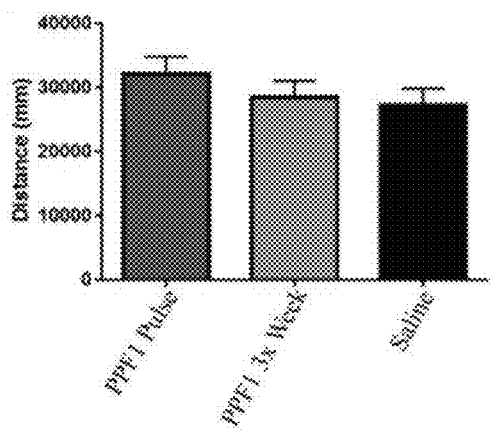
FIG. 1A depicts distance traveled in an open field test in mice treated with PPF1 using Pulse Dose and 3x/week dosing regimens.

The present invention relates to the identification and discovery of methods and compositions for the treatment and/or prevention of cognitive and motor impairment, including age-associated dementia or decline in motor function and/or neurodegenerative disease. Described herein are methods and compositions for the treatment of subjects suffering from such disorders, which are aspects of the present invention. Also described herein are dosing regimens which trigger neurogenesis or decreased neuroinflammation and/or cognitive or motor improvement in subjects suffering from cognitive or motor impairment. The methods and compositions described herein are useful in: preventing cognitive or motor impairment, age-associated dementia, neuroinflammation, and/or neurodegenerative disease; ameliorating the symptoms of cognitive or motor impairment, age-associated dementia, neuroinflammation, and/or neurodegenerative disease; slowing progression of aging-associated cognitive or motor impairment, age-associated dementia, neuroinflammation and/or neurodegenerative disease; and/or reversing the progression of aging-associated cognitive or motor impairment, age-associated dementia, neuroinflammation, and/or neurodegenerative disease. An implementation of the invention includes using blood plasma fractions as treatment, such as one or more fractions or effluents obtained from blood fractionation processes, e.g., like the Cohn fractionation process described below. An embodiment of the invention includes using Plasma Fraction (a solution comprised of normal human albumin, alpha and beta globulins, gamma globulin, and other proteins either individually or as complexes, hereinafter referred to as "Plasma Fraction"). Another embodiment of the invention includes using Plasma Protein Fraction (PPF) as treatment. Another embodiment of the invention includes using Human Albumin Solution (HAS) fraction as treatment. Yet another embodiment includes using effluents from blood fractionation processes such as Effluent I or Effluent II/III described below. An additional embodiment includes a blood plasma fraction from which substantially all the clotting factors have been removed in order to retain efficacy while reducing the risk of thromboses (for example, see U.S. Patent Application Nos. 62/236,710 and 63/376,529, which are incorporated by reference in their entirety herein).

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

2. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the newborn. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

By "an individual suffering from or at risk of suffering from an aging-associated cognitive impairment" is meant an individual that is about more than 50% through its expected lifespan, such as more than 60%, e.g., more than 70%, such as more than 75%, 80%, 85%, 90%, 95% or even 99% through its expected lifespan. The age of the individual will depend on the species in question. Thus, this percentage is based on the predicted life-expectancy of the species in question. For example, in humans, such an individual is 50 year old or older, e.g., 60 years old or older, 70 years old or older, 80 years old or older, 90 years old or older, and usually no older than 100 years old, such as 90 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old or older, or any age between 50-1000, that suffers from an aging-associated condition as further described below, e.g., cognitive impairment associated with the natural aging process; an individual that is about 50 years old or older, e.g., 60 years old or older, 70 years old or older, 80 years old or older, 90 years old or older, and usually no older than 100 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old, that has not yet begun to show symptoms of an aging-associated condition e.g., cognitive impairment; an individual of any age that is suffering from a cognitive impairment due to an aging-associated disease, as described further below, and an individual of any age that has been diagnosed with an aging-associated disease that is typically accompanied by cognitive impairment, where the individual has not yet begun to show symptoms of cognitive impairment. The corresponding ages for non-human subjects are known and are intended to apply herein.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc. The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

In some embodiments, the aging-associated condition that is treated is an aging-associated impairment in cognitive ability in an individual. By cognitive ability, or "cognition," it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

In some embodiments, the aging-associated condition that is treated is an aging-associated impairment in motor ability in an individual. By motor ability, it is meant the motor processes that include the ability to perform complex muscle-and-nerve actions that produce movement such as fine motor skills producing small or precise movements (e.g. writing, tying shoes) and gross motor skills for large movements (e.g. walking, running, kicking). By "motor decline", it is meant a progressive decrease in one or more of these abilities, e.g., a decline in find movement or gross motor skills, etc. By "motor impaired" and "motor impairment", it is meant a reduction in motor ability/skills relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated motor impairment," it is meant an impairment or decline in motor ability that is typically associated with aging, including, for example, motor impairment associated with the natural aging process and motor impairment or decline associated with an aging-associated disorder, that is, a disorder that is seen with increasing frequency with increasing senescence, e.g., a neurodegenerative condition such as Parkinson's disease, amyotrophic lateral sclerosis, and the like.

In some embodiments, the aging-associated condition that is treated is an aging-associated increase in neuroinflammation in an individual. By "neuroinflammation" it is meant biochemical and cellular responses of the nervous system to injury, infection, or neurodegenerative diseases. Such responses are directed at decreasing the triggering factors by involving central nervous system immunity to defend against potential harm. Neurodegeneration occurs in the central nervous system and exhibits hallmarks of loss of neuronal structure and function. Neuroinflammatory diseases or neuroinflammatory-associated conditions or diseases, includes by way of example and not limitation, neurodegenerative diseases such as Alzheimer's disease; Parkinson's disease, multiple sclerosis and the like.

Blood Products Comprising Plasma Components.

In practicing the subject methods, a blood product comprising plasma components is administered to an individual in need thereof, e.g., an individual suffering or at risk of suffering from a cognitive or motor impairment, neuroinflammation and/or age-related dementia. As such, methods according to embodiments of the invention include administering a blood product comprising plasma components from an individual (the "donor individual", or "donor") to an individual at least at risk of suffering or suffering from cognitive or motor impairment, neuroinflammation, neurodegeneration, and/or age-related dementia (the "recipient individual" or "recipient"). By a "blood product comprising plasma components," it is meant any product derived from blood that comprises plasma (e.g. whole blood, whole plasma, or fractions thereof). The term "plasma" is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), blood products consisting of plasmapheretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of Blood Products Comprising Plasma Components.

Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In a preferred embodiment, the process of plasmapheresis is used to obtain the plasma comprising blood products. Plasmapheresis can comprise the removal of a weight-adjusted volume of plasma with the return of cellular components to the donor. In the preferred embodiment, sodium citrate is used during plasmapheresis in order to prevent cell clotting. The volume of plasma collected from a donor is preferably between 690 to 880 mL after citrate administration, and preferably coordinates with the donor's weight.

3. Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See Johan, Current Approaches to the Preparation of Plasma Fractions in (Biotechnology of Blood) 165 (Jack Goldstein ed., 1st ed. 1991)). Dr. Cohn's procedure of purifying plasma fractions utilized cold ethanol for its denaturing effect and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction (or effluent from a prior separation step) contains or potentially contains therapeutically-useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions.

More recently, fractionation has reached further complexity, and as such, comprises additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. One of ordinary skill in the art would recognize that the parameters described above may be adjusted to obtain specifically-desired plasma protein-containing fractions.

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 4,624,780, 5,219,995, 5,288,853, and U.S.

patent application nos. 20140343255 and 20150343025, which disclosures are incorporated by reference in their entirety herein.

In an embodiment of the invention, the plasma fraction may comprise a plasma fraction containing a substantial concentration of albumin. In another embodiment of the invention, the plasma fraction may comprise a plasma fraction containing a substantial concentration of IgG or intravenous immune globulin (IGIV) (e.g. Gamunex-C®). In another embodiment of the invention the plasma fraction may comprise an IGIV plasma fraction, such as Gamunex-C® which has been substantially depleted of immune globulin (IgG) by methods well-known by one of ordinary skill in the art, such as for example, Protein A-mediated depletion. (See Keshishian, H., et al., Multiplexed, Quantitative Workflow for Sensitive Biomarker Discovery in Plasma Yields Novel Candidates for Early Myocardial Injury, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

4. Albumin Products

To those having ordinary skill in the art, there are two general categories of Albumin Plasma Products ("APP"): plasma protein fraction ("PPF") and human albumin solution ("HAS"). PPF is derived from a process with a higher yield than HAS but has a lower minimum albumin purity than HAS (>83% for PPF and >95% for HAS). (Production of human albumin solution: a continually developing colloid, P. Matejtschuk et al., British J. of Anaesthesia 85(6): 887-95, at 888 (2000)). In some instances, PPF has albumin purity of between 83% and 95% or alternatively 83% and 96%. The albumin purity can be determined by electrophoresis or other quantifying assays such as, for example, by mass spectrometry. Additionally, some have noted that PPF has a disadvantage because of the presence of protein "contaminants" such as PKA. Id. As a consequence, PPF preparations have lost popularity as Albumin Plasma Products, and have even been delisted from certain countries' Pharmacopoeias. Id. Contrary to these concerns, the invention makes beneficial use of these "contaminants." Besides α, β, and γ globulins, as well as the aforementioned PKA, the methods of the invention utilize additional proteins or other factors within the "contaminants" that promote processes such as neurogenesis, neuronal cell survival, improved cognition or motor function and decreased neuroinflammation.

Those of skill in the art will recognize that there are, or have been, several commercial sources of PPF (the "Commercial PPF Preparations.") These include Plasma-Plex™ PPF (Armour Pharmaceutical Co., Tarrytown, N.Y.), Plasmanate™ PPF (Grifols, Clayton, N.C.), Plasmatein™ (Alpha Therapeutics, Los Angeles, Calif.), and Protenate™ PPF (Baxter Labs, Inc. Deerfield, Ill.).

Those of skill in the art will also recognize that there are, or have been, several commercial sources of HAS (the "Commercial HAS Preparations.") These include Albuminar™ (CSL Behring), AlbuRx™ (CSL Behring), Albutein™ (Grifols, Clayton, N.C.), Buminate™ (Baxatla, Inc., Bannockburn, Ill.), Flexbumin™ (Baxatla, Inc., Bannockburn, Ill.), and Plasbumin™ (Grifols, Clayton, N.C.).

a. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF's source material is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0+/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including α1, α2, β, and γ globulins) and other plasma proteins, and no more than 1% gamma globulin as determined by electrophoresis. (Hink, J H, Jr., et al., Preparation and Properties of a Heat-Treated Human Plasma Protein Fraction, VOX SANGUINIS 2(174) (1957)). PPF can also refer to a solid form, which when suspended in solvent, has similar composition. The total globulin fraction can be determined through subtracting the albumin from the total protein. (Busher, J., Serum Albumin and Globulin, CLINICAL METHODS: THE HISTORY, PHYSICAL, AND LABORATORY EXAMINATIONS, Chapter 10, Walker H K, Hall W D, Hurst J D, eds. (1990)).

b. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein concentration. Final product shall conform to one of the following concentrations: 4.0+/−0.25 percent; 5.0+/−0.30 percent; 20.0+/−1.2 percent; and 25.0+/−1.5 percent solution of protein.

(b) Protein composition. At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including α1, α2, β, and γ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

5. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating or preventing an aging-related condition such as cognitive or motor impairment, neuroinflammation or neurodegeneration in a subject. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application No. 62/376,529 filed on Aug. 18, 2016, which is incorporated by reference in its entirety herein.

6. Protein-Enriched Plasma Protein Products Treatment

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III are all effectively devoid of clotting factors. Such plasma fractions are hereinafter referred to as "protein-enriched plasma protein products". For example, an embodiment of the invention may use a protein-enriched plasma protein product comprised of 82% albumin and 18% α, β, and γ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0% albumin and 100% of α, β, and γ globulins and other plasma proteins Embodiments of the invention described above may also have total gamma globulin concentrations of 1-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

7. Preparation of Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution for inhibition of coagulation, with further separation of Fractions I, II+III, IV, and PPF as per the method disclosed in Hink et al. (See Hink, J H, Jr., et al., Preparation and Properties of a Heat-Treated Human Plasma Protein Fraction, VOX SANGUINIS 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III ("Effluent II/III") through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II/III at −6° C. for 6 hours. Precipitated Fraction VI-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one-part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C.

The recovered proteins (stable plasma protein fraction) can be dried (e.g. by freeze drying) to remove alcohol and H20. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

One having ordinary skill in the art would recognize that each of the different fractions and effluents described above could be used with the methods of the invention to treat disease. For example, and not by way of limitation, Effluents I or Effluent II/III may be utilized to treat such diseases as cognitive, motor, and neurodegenerative disorders and are embodiments of the invention.

The preceding methods of preparing plasma fractions and plasma protein fraction (PPF) are only exemplary and involves merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional plasma fractions. For example, the invention, among other things, demonstrates that specific concentrations of albumin are not critical for improving cognitive or motor activity. Hence, fractions with reduced albumin concentration, such as those fractions having below 83% albumin, are contemplated by the invention.

8. Treatment

Aspects of the methods of the inventions described herein include treatment of a subject with a plasma comprising blood product, such as a blood plasma fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment and/or prevention of cognitive or motor impairment, neuroinflammation, neurodegeneration, and/or age-related dementia. In one embodiment, the plasma comprising blood product is administered immediately, e.g., within about 12-48 hours of collection from a donor, to the individual suffering or at risk from a cognitive or motor impairment, neuroinflammation, neurodegeneration, and/or age-related dementia. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is PPF or HAS. In a further embodiment of the invention, the plasma fraction is one of the Commercial PPF Preparations of the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

9. Administration

Aspects of the methods of the inventions described herein include treatment of a subject with a plasma comprising blood product, such as a blood plasma or Plasma Fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment and/or prevention of cognitive or motor impairment, neuroinflammation, neurodegeneration, and/or age-related dementia. In one embodiment, the plasma comprising blood product is administered immediately, e.g., within about 12-48 hours of collection from a donor, to the individual suffering or at risk from a cognitive or motor impairment, neuroinflammation, neurodegeneration, and/or age-related dementia. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is PPF or HAS. In a further embodiment of the invention, the plasma fraction is one of the Commercial PPF Preparations of the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

An embodiment of the invention includes treating a subject diagnosed with a cognitive or motor impairment, neurodegeneration, or neuroinflammation by administering to the subject an effective amount of blood plasma or Plasma Fraction. Another embodiment of the invention includes administering the effective amount of blood plasma or Plasma Fraction and subsequently monitoring the subject for improved cognitive or motor function, or a reduction in neuroinflammation or increase in neurogenesis. Another embodiment of the invention includes treating a subject diagnosed with a cognitive or motor impairment, neurodegeneration, or neuroinflammation by administering to the subject an effective amount of blood plasma or Plasma Fraction wherein the blood plasma or Plasma Fraction is administered in a manner resulting in improved cognitive or motor function, decreased neuroinflammation, or improved neurogenesis after the mean or median half-life of the blood plasma proteins or Plasma Fraction proteins been reached, relative to the most recent administered dose (referred to as "Pulsed Dosing" or "Pulse Dosed" herein). Another embodiment of the invention includes administering the blood plasma or Plasma Fraction via a dosing regimen of at least two consecutive days and monitoring the subject for improved cognitive or motor function, decreased neuroinflammation or improved neurogenesis at least 3 days after the date of last administration. A further embodiment of the invention includes administering the blood plasma or Plasma Fraction via a dosing regimen of at least 3, 4, 5, 6, 7, 8, 9, 10, 11, 12, 13, or 14 consecutive days and monitoring the subject for improved cognitive or motor function, decreased neuroinflammation, or increased neurogenesis at least 3 days after the date of last administration. Yet another embodiment of the invention includes administering the blood plasma or Plasma Fraction via a dosing regimen of at least 2 consecutive days and after the date of last administration, monitoring for cognitive or motor function improvement, decreased neuroinflammation, or increased neurogenesis beyond when the average half-life of the proteins in the blood plasma or Plasma Fraction has been reached. Another embodiment of the invention includes administering the blood plasma or Plasma Fraction via a dosing regimen of 2 to 14 non-consecutive days wherein each gap between doses may be between 0-3 days each.

In some instances, Pulsed Dosing in accordance with the invention includes administration of a first set of doses, e.g., as described above, followed by a period of no dosing, e.g., a "dosing-free period", which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse the progression of the cognitive or impairment, neuroinflammation, neurodegeneration, or age-associated dementia.

10. Plasma Protein Fraction

In practicing methods of the invention, a plasma fraction is administered to the subject. In an embodiment, the plasma fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Further embodiments of this embodiment used in practicing methods of the invention include, for example, the embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

11. Plasma Fractions of Specific Donor Age

Additional embodiments of the invention include administering a plasma protein fraction derived from the plasma of individuals of certain age ranges. An embodiment includes administering PPF or HAS which have been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range.

12. Indications

The subject methods and plasma-comprising blood products and fractions find use in treating, including preventing, aging-associated conditions, such as impairments in the cognitive or motor ability of individuals, e.g., cognitive disorders, including (but not limited to) age-associated dementia, immunological conditions, cancer, and physical and functional decline; and motor disorders such as (but not limited to) Parkinson's disease. Individuals suffering from or at risk of developing an aging-associated cognitive or motor impairment, neuroinflammation, and/or neurodegeneration that will benefit from treatment with the subject plasma-comprising blood product, e.g., by the methods disclosed herein, include individuals that are about 50 years old or older, e.g., 60 years old or older, 70 years old or older, 80 years old or older, 90 years old or older, and 100 years old or older, i.e., between the age of about 50 and 100, e.g., 50, 55, 60, 65, 70, 75, 80, 85, 90, 95 or about 100 years old, and are suffering from cognitive or motor impairment, neuroinflammation, and/or neurodegeneration associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive or motor impairment, neuroinflammation and/or neurodegeneration. Examples of cognitive and motor, neuroinflammatory, and/or neurodegenerative impairments that are due to natural aging include the following:

a. Mild Cognitive Impairment (M.C.I.).

Mild cognitive impairment is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product or fraction, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

b. Alzheimer's Disease.

Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons>60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus coeruleus, and nucleus raphae *dorsalis*. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

c. Parkinson's Disease.

Parkinson's Disease (PD) is an idiopathic, slowly progressive, degenerative CNS disorder characterized by slow and decreased movement (bradykinesia), muscular rigidity, resting tremor (dystonia), muscle freezing, and postural instability. Originally considered primarily a motor disorder, PD is now recognized to also cause depression and emotional changes. PD also can affect cognition, behavior, sleep, autonomic function, and sensory function. The most common cognitive impairments include an impairment in attention and concentration, working memory, executive function, producing language, and visuospatial function. A characteristic of PD is symptoms related to reduced motor function usually precede those related to cognitive impairment, which aids in diagnosis of the disease.

In primary Parkinson's disease, the pigmented neurons of the substantia nigra, locus coeruleus, and other brain stem dopaminergic cell groups degenerate. The cause is not known. The loss of substantia nigra neurons, which project to the caudate nucleus and putamen, results in depletion of the neurotransmitter dopamine in these areas. Onset is generally after age 40, with increasing incidence in older age groups.

Parkinson's disease is newly diagnosed in about 60,000 Americans each year and currently affects approximately one million Americans. Even though PD is not fatal in itself, its complications are the fourteenth leading cause of death in the United States. At present, PD cannot be cured, and treatment is generally prescribed to control symptoms, with surgery prescribed in later, severe cases.

Treatment options for PD include administration of pharmaceuticals to help manage motor deficits. These options increase or substitute for the neurotransmitter, dopamine, of which PD patients have low brain concentrations. Such medications include: carbidopa/levodopa (which create more dopamine in the brain); apomorphine, pramipexolole, ropinirole, and rotingotine (dopamine agonists); selegiline and rasagiline (MAO-B inhibitors which prevent breakdown of dopamine); entacapone and tolcapone (Catechol-O-methyltransferase [COMT] inhibitors which make more levodopa available in the brain); benztropine and trihexyphenidyl (anticholinergics); and amantadine (controls tremor and stiffness). Exercise/physical therapy is also commonly prescribed to help maintain physical and mental function.

Current treatment options, however treat the symptoms of PD, are not curative, and fail to prevent disease progression. Additionally, current medications tend to lose efficacy in late stage PD. The most prescribed drug, levodopa, commonly results in adverse effects within 5 to 10 years after commencing the medication. These adverse effects can be severe and can result in motor fluctuations and unpredictable swings in motor control between doses as well as jerking/twitching (dyskinesia) which are difficult to manage and are even as disabling as PD's own symptoms. Thus, there remains a need for new therapies with new mechanisms of action which can either be administrated along or in combination with current PD medications.

d. Parkinsonism.

Secondary parkinsonism (also referred to as atypical Parkinson's disease or Parkinson's plus) results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including nigrostriatal degeneration. Certain disorders like Progressive Supranuclear Palsy (PSP), Multiple System Atrophy (MSA), Corticobasal degeneration (CBD) and Dementia with Lewy Bodies (DLB) can exhibit Parkinsonism symptoms before the cardinal symptoms necessary to the specific diagnosis can be made, and thus may be labeled as "Parkinsonism."

e. Frontotemporal Dementia.

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected:

Behavioral variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies." Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

f. Huntington's Disease.

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

g. Amyotrophic Lateral Sclerosis.

Amyotrophic lateral sclerosis (ALS) is a rapidly progressive, invariably fatal, neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years.

Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

h. Multiple Sclerosis.

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

i. Glaucoma.

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

j. Myotonic Dystrophy.

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotoninprotein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

k. Dementia.

Dementia describes a class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall.

Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (POD) would be the diagnosis when dementia onset is more than a year after the onset of Parkinson's. DLB is diagnosed when cognitive symptoms begin at the same time or within a year of Parkinson symptoms.

l. Progressive Supranuclear Palsy.

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

m. Ataxia.

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

n. Multiple-System Atrophy.

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation.

The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

o. Frailty.

Frailty Syndrome ("Frailty") is a geriatric syndrome characterized by functional and physical decline including decreased mobility, muscle weakness, physical slowness, poor endurance, low physical activity, malnourishment, and involuntary weight loss. Such decline is often accompanied and a consequence of diseases such as cognitive dysfunction and cancer. However, Frailty can occur even without disease. Individuals suffering from Frailty have an increased risk of negative prognosis from fractures, accidental falls, disability, comorbidity, and premature mortality. (C. Buigues, et al. Effect of a Prebiotic Formulation on Frailty Syndrome: A Randomized, Double-Blind Clinical Trial, Int. J. Mol. Sci. 2016, 17, 932). Additionally, individuals suffering from Frailty have an increased incidence of higher health care expenditure. (Id.)

Common symptoms of Frailty can be determined by certain types of tests. For example, unintentional weight loss involves a loss of at least 10 lbs. or greater than 5% of body weight in the preceding year; muscle weakness can be determined by reduced grip strength in the lowest 20% at baseline (adjusted for gender and BMI); physical slowness can be based on the time needed to walk a distance of 15 feet; poor endurance can be determined by the individual's self-reporting of exhaustion; and low physical activity can be measured using a standardized questionnaire. (Z. Palace et al., The Frailty Syndrome, Today's Geriatric Medicine 7(1), at 18 (2014)).

In some embodiments, the subject methods and compositions find use in slowing the progression of aging-associated cognitive, motor, neuroinflammatory, or other age-related impairment or condition. In other words, cognitive, motor, neuroinflammatory, or other abilities or conditions in the individual will decline more slowly following treatment by the disclosed methods than prior to or in the absence of treatment by the disclosed methods. In some such instances, the subject methods of treatment include measuring the progression of cognitive, motor, neuroinflammation, or other age-related ability or symptom decline after treatment, and determining that the progression of decline is reduced. In some such instances, the determination is made by comparing to a reference, e.g., the rate of decline in the individual prior to treatment, e.g., as determined by measuring cognitive, motor, neuroinflammatory, or other age-related abilities or conditions prior at two or more time points prior to administration of the subject blood product.

The subject methods and compositions also find use in stabilizing the cognitive, motor, neuroinflammatory, or other abilities or conditions of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive, motor, neuroinflammatory, or other age-related impairment in an individual suffering from an aging-associated impairment. In other words, the affected ability is improved in the individual following treatment by the subject methods. For example, the cognitive or motor ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-old or more, following treatment by the subject methods relative to the cognitive or motor ability that is observed in the individual prior to treatment by the subject methods.

In some instances, treatment by the subject methods and compositions restores the cognitive, motor, or other ability in the individual suffering from aging-associated cognitive or motor decline, e.g., to their level when the individual was about 40 years old or less. In other words, cognitive or motor impairment is abrogated. Methods of Diagnosing and Monitoring for Improvement 13. In some instances, among the variety of methods to diagnose and monitor disease progression and improvement in cognitive disease, motor impairment, neurodegenerative disease, and/or neuroinflammatory disease the following types of assessments are used alone or in combination with subjects suffering from neurodegenerative disease, as desired. The following types of methods are presented as examples and are not limited to the recited methods. Any convenient methods to monitor disease may be used in practicing the invention, as desired. Those methods are also contemplated by the methods of the invention.

a. General Cognition

Embodiments of the methods of the invention further comprise methods of monitoring the effect of a medication or treatment on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy. In one embodiment, monitoring the effect on cognitive impairment and/or age-related dementia includes a 1, 2, 3, 4, 5, 6, 7, 8, 9, 10, 11, or 12-point improvement using the Alzheimer's Disease Assessment Scale-Cognitive Subscale (ADAS-COG).

In one embodiment, examinations of the peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

b. Parkinson's Disease

Embodiments of the methods of the invention further comprise methods of monitoring the effect of a medication or treatment on a subject for treating motor impairment, the method comprising comparing motor function before and after treatment. Those having ordinary skill in the art recognize that there are well-known methods of evaluating motor function. For example, and not by way of limitation, the method may comprise evaluation of motor function based on medical history, family history, physical and neurological examinations by clinicians who specialize neurodegeneration and motor impairment, laboratory tests, and neurodegenerative assessment. Additional embodiments which are contemplated by the invention include employment of the rating scales discussed below.

Several rating scales have been utilized for evaluating the progression of PD. The most widely-used scales include the Unified Parkinson's Disease Rating Scale (UPDRS, which was introduced in 1987) (J. Rehabil Res. Dev., 2012 49(8): 1269-76), and the Hoehn and Yahr scale (Neruology, 1967 17(5): 427-42). Additional scales include the Movement Disorder Society (MDS)'s updated UPDRS scale (MDS-UPDRS) as well as the Schwab and England Activities of Daily Living (ADL) Scale.

The UPDRS scale evaluates 31 items that contributed to three subscales: (1) mentation, behavior, and mood; (2) activities of daily living; and (3) motor examination. The Hoehn and Yahr scale classifies PD into five stages with discreet substages: 0—no signs of disease; 1—symptoms on one side only; 1.5—symptoms on one side but also involving neck and spine; 2—symptoms on both sides with no balance impairment; 2.5—mild symptoms on both sides, with recovery when the 'pull' test is given; 3—balance impairment with mild to moderate disease; 4—severe disability, but ability to walk or stand unassisted; and 5—need a wheelchair or bedridden without assistance. The Schwab and England scale classifies PD into several percentages (from 100%—complete independent to 10%—total dependent).

General motor function can be evaluated using widely-used scales including the General Motor Function Scale (GMF). This tests three components: dependence, pain, and insecurity. (Aberg A. C., et al. (2003) Disabil. Rehabil. 2003 May 6; 25(9):462-72.). Motor function can also be assessed using home-monitoring or wearable sensors. For example:

gait (speed of locomotion, variability, leg rigidity) can be sensed with an accelerometer; posture (trunk inclination) by a gyroscope; leg movement by an accelerometer; hand movement by an accelerometer and gyroscope; tremor (amplitude, frequency, duration, asymmetry) by an accelerometer; falling by an accelerometer; gait freezing by an accelerometer; dyskinesia by an accelerometer, gyroscope, and inertial sensors; bradykinesia (duration and frequency) by an accelerometer plus gyroscope, and aphasia (pitch) using a microphone. (Pastorino M, et al., Journal of Physics: Conference Series 450 (2013) 012055).

c. Multiple Sclerosis

In addition to monitoring improvement for symptoms associated with cognition, the progression or improvement of neurodegeneration associated with multiple sclerosis (MS) can be monitored using techniques well-known to those having ordinary skill in the art. By way of example, and not limitation, monitoring can be performed through techniques such as: cerebrospinal fluid (CSF) monitoring; magnetic resonance imaging (MRI) to detect lesions and development of demyelinating plaques; evoked potential studies; and gait monitoring.

CSF analysis may be performed, for example, through lumbar puncture to obtain pressure, appearance, and CSF content. Normal values typically range as follows: pressure (70-180 mm H20); appearance is clear and colorless; total protein (15-60 mg/100 mL); IgG is 3-12% of the total protein; glucose is 50-80 mg/100 mL; cell count is 0-5 white blood cells and no red blood cells; chloride (110-125 mEq/L). Abnormal results may indicate the presence or progression of MS.

MRI is another technique that may be performed to monitor disease progression and improvement. Typical criteria for monitoring MS with MRI include the appearance of patchy areas of abnormal white matter in cerebral hemisphere and in paraventricular areas, lesions present in the cerebellum and/or brain stem as well as in the cervical or thoracic regions of the spinal cord.

Evoked potentials may be used to monitor the progression and improvement of MS in subjects. Evoked potentials measure slowing of electrical impulses such as in Visual Evoked Response (VER), Brain Stem Auditory Evoked Responses (BAER), and Somatosensory Evoked Responses (SSER). Abnormal responses help to indicate that there is a decrease in the speed of conduction in central sensory pathways.

Gait monitoring can also be used to monitor disease progression and improvement in MS subjects. MS is often accompanied by an impairment in mobility and an abnormal gait due in part to fatigue. Monitoring may be performed, for example, with the use of mobile monitoring devices worn by subjects. (Moon, Y., et al., Monitoring gait in multiple sclerosis with novel wearable motion sensors, PLOS One, 12(2):e0171346 (2017)).

d. Huntington's

In addition to monitoring improvement for symptoms associated with cognition, the progression or improvement of neurodegeneration associated with Huntington's Disease (HD) can be monitored using techniques well-known to those having ordinary skill in the art. By way of example, and not limitation, monitoring can be performed through techniques such as: motor function; behavior; functional assessment; and imaging.

Examples of motor function that may be monitored as an indication of disease progression or improvement include chorea and dystonia, rigidity, bradykinesia, oculomotor dysfunction, and gait/balance changes. Techniques for performing the monitoring of these metrics are well-known to those having ordinary skill in the art. (See Tang C, et al., Monitoring Huntington's disease progression through preclinical and early stages, Neurodegener Dis Manag 2(4):421-35 (2012)).

The psychiatric effects of HD present opportunities to monitor disease progression and improvement. For example, psychiatric diagnoses may be performed in order to determine whether the subject suffers from depression, irritability, agitation, anxiety, apathy and psychosis with paranoia. (Id.)

Functional assessment may also be employed to monitor disease progression or improvement. Total functional score techniques have been reported (Id.), and often declines by one point per year in some HD groups.

MRI or PET may be employed also to monitor disease progression or improvement. For example, there is a loss of striatal projection neurons in HD, and change in number of these neurons may be monitored in subjects. Techniques to determine neuronal change in HD subjects include imaging Dopamine D2 receptor binding. (Id.)

e. ALS

In addition to monitoring improvement for symptoms associated with cognition, the progression or improvement of neurodegeneration associated with Amyotrophic Lateral Sclerosis (ALS) can be monitored using techniques well-known to those having ordinary skill in the art. By way of example, and not limitation, monitoring can be performed through techniques such as: functional assessment; determining muscle strength; measuring respiratory function; measuring lower motor neuron (LMN) loss; and measuring upper motor neuron (UMN) dysfunction.

Functional assessment can be performed using a functional scale well-known to those having ordinary skill in the art, such as the ALS Functional Rating Scale (ALSFRS-R), which evaluates symptoms related to bulbar, limb, and respiratory function. The rate of change is useful in predicting survival as well as disease progression or improvement. Another measure includes the Combined Assessment of Function and Survival (CAFS), ranking subjects' clinical outcomes by combining survival time with change in ALSFRS-R. (Simon N G, et al., Quantifying Disease Progression in Amyotrophic Lateral Sclerosis, Ann Neurol 76:643-57 (2014)).

Muscle strength may be tested and quantified through use of composite Manual Muscle Testing (MMT) scoring. This entails averaging measures acquired from several muscle groups using the Medical Research Council (MRC) muscle strength grading scale. (Id.) Hand-held dynamometry (HHD) may also be used, among other techniques. (Id.)

Respiratory function can be performed using portable spirometry units, used to obtain Forced Vital Capacity (FVC) at baseline to predict the progression or improvement of the disease. Additionally, maximal inspiratory pressure, sniff nasal inspiratory pressure (SNIP), and supping FVC may be determined and used to monitor disease progression/improvement. (Id.)

Loss in lower motor neurons is another metric which can be utilized to monitor disease progression or improvement in ALS. The Neurophysiological Index may be determined by measuring compound muscle action potentials (CMAPs) on motor nerve conduction studies, of which parameters include CMAP amplitude and F-wave frequency. (Id. and de Carvalho M, et al., Nerve conduction studies in amyotrophic lateral sclerosis. Muscle Nerve 23:344-352, (2000)). Lower motor neuron unit numbers (MUNE) may be estimated as well. In MUNE, the number of residual motor axons supplying a muscle through estimation of the contribution of individual motor units to the maximal CMAP response is estimated, and used to determine disease progression or improvement. (Simon N G, et al., supra). Additional techniques for determining loss of LMN include testing nerve excitability, electrical impedance myography, and using muscle ultrasound to detect changes in thickness in muscles. (Id.)

Dysfunction of upper motor neurons is another metric which can be utilized to monitor disease progression or improvement in ALS. Techniques for determining dysfunction include performing MRI or PET scans on the brain and spinal cord, transcranial magnetic stimulation; and determining levels of biomarkers in the cerebrospinal fluid (CSF).

f. Glaucoma

In addition to monitoring improvement for symptoms associated with cognition, the progression or improvement of neurodegeneration associated with glaucoma can be monitored using techniques well-known to those having ordinary skill in the art. By way of example, and not limitation, monitoring can be performed through techniques such as: determining intraocular pressure; assessment of the optic disc or optic nerve head for damage; visual field testing for peripheral vision loss; and imaging of the optic disc and retina for topographic analysis.

g. Progressive Supranuclear Palsy (PSP)

In addition to monitoring improvement for symptoms associated with cognition, the progression or improvement of neurodegeneration associated with Progressive Supranuclear Palsy (PSP) can be monitored using techniques well-known to those having ordinary skill in the art. By way of example, and not limitation, monitoring can be performed through techniques such as: functional assessment (activities of daily living, or ADL); motor assessment; determination of psychiatric symptoms; and volumetric and functional magnetic resonance imaging (MRI).

The level of function of a subject in terms of independence, partial dependence upon others, or complete dependence can be useful for determining the progression or improvement in the disease. (See Duff, K, et al., Functional impairment in progressive supranuclear palsy, Neurology 80:380-84, (2013)). The Progressive Supranuclear Palsy Rating Scale (PSPRS) is a rating scale that comprises twenty-eight metrics in six categories: daily activities (by history); behavior; bulbar, ocular motor, limb motor and gait/midline. The result is a score ranging from 0-100. Six items are graded 0-2 and twenty-two items graded 0-4 for a possible total of 100. The PSPRS scores are practical measures, and robust predictors of patient survival. They are also sensitive to disease progression and useful in monitoring disease progression or improvement. (Golbe L I, et al., A clinical rating scale for progressive supranuclear palsy, Brain 130:1552-65, (2007)).

The ADL section from the UPDRS (Unified Parkinson's Disease Rating Scale) can also be used to quantify functional activity in subjects with PSP. (Duff K, et al., supra). Similarly, the Schwab & England Activities Daily Living Score (SE-ADL) can be used for evaluate independence. (Id.) Additionally, the motor function sections of the UPDRS are useful as a reliable measure for assessing disease progression in PSP patients. The motor section may contain, for example, 27 different measures for quantifying motor function in PSP patients. Examples of these include resting tremor, rigidity, finger tapping, posture, and gait). A subject's disease progression or improvement may also be assessed by performing a baseline neuropsychological evaluation completed by trained medical personnel, the assessment using the Neuropsychiatric Inventory (NPI) to determine the frequency and severity of behavior abnormalities (e.g. delusions, hallucinations, agitation, depression, anxiety, euphoria, apathy, disinhibition, irritability, and aberrant motor behavior). (Id.)

Functional MRI (fMRI) can be employed to monitor disease progression and improvement as well. fMRI is a technique using MRI to measure changes in brain activity in certain regions of the brain, usually based on blood flow to those regions. Blood flow is considered to correlate with brain region activation. Patients with neurodegenerative disorders like PSP can be subjected to physical or mental tests before or during being scanned in an MRI scanner. By way of example, and not limitation, tests can be a well-established force control paradigm where patients as asked to produce force with the hand most affected by PSP and maximum voluntary contraction (MVC) is measured by fMRI immediately after the test takes place. Burciu, R G, et al., Distinct patterns of brain activity in progressive supranuclear palsy and Parkinson's disease, Mov. Disord. 30(9): 1248-58 (2015)).

Volumetric MRI is a technique where MRI scanners determine volume differences in regional brain volume. This may be done, for example, by contrasting different disorders, or by determining differences in volume of a brain region in a patient over time. Volumetric MRI may be employed to determine disease progression or improvement in neurodegenerative disorders like PSP. The technique is well-known to those having ordinary skill in the art. (Messina D, et al., Patterns of brain atrophy in Parkinson's disease, progressive supranuclear palsy and multiple system atrophy, Parkinsonism and Related Disorders, 17(3):172-76 (2011)). Examples of cerebral regions which may be measured include, but are not limited to, intracranial volume, cerebral cortex, cerebellar cortex, thalamus, caudate, putamen, *pallidum*, hippocampus, amygdala, lateral ventricles, third ventricle, fourth ventricle, and brain stem.

h. Neurogenesis

The invention also contemplates treating or improving neurogenesis in a subject with declining or impaired neurogenesis, which may manifest itself, for example, through reduced cognitive or motor function, or through association with neuroinflammation. An embodiment of the invention includes administering, by way of example and not limitation, a blood plasma, a plasma fraction, or a PPF to the subject with reduced or impaired neurogenesis using a Pulsed Dosing treatment regimen.

An embodiment of the invention also contemplates determining the level of neurogenesis before, during, and/or after administration of the blood plasma, plasma fraction, or PPF. Noninvasive techniques for evaluating neurogenesis have been reported. (Tamura Y. et al., J. Neurosci. (2016) 36(31): 8123-31). Positron emission tomography (PET) used with the tracer, [18F]FLT, in combinations with the BBB transporter inhibitor probenecid, allows for accumulation of the tracer in neurogenic regions of the brain. Such imaging allows for an evaluation of neurogenesis in patients being treated for neurodegenerative disease.

i. Neuroinflammation

The invention also contemplates treating or improving neuroinflammation in a subject with heightened neuroinflammation, which may manifest itself, for example, through reduced cognitive or motor function, or through association with reduced neurogenesis or neurodegeneration. An embodiment of the invention includes administering, by way of example and not limitation, a blood plasma, a plasma fraction, or a PPF to the subject with neuroinflammation using a Pulsed Dosing treatment regimen.

An embodiment of the invention also contemplates determining the level of neuroinflammation before, during, and/or after administration of the blood plasma, plasma fraction, or PPF. Noninvasive techniques for evaluating neuroinflammation have been reported such as TSPO Positron Emission Tomography (TSPO PET) using $^{11}$C-PK11195 and other such tracers. (See Vivash L, et al., J. Nucl. Med. 2016, 57:165-68; and Janssen B, et al., Biochim. et Biophys. Acta, 2016, 425-41, herein incorporated by reference). Invasive techniques for evaluating neuroinflammation include drawing of cerebrospinal fluid and detecting, for example, expression levels of neuroinflammatory markers or factors such as (but not limited to) prostaglandin E2, cyclooxygenase-2, TNF-alpha, IL-6, IFN-gamma, IL-10, eotaxin, beta-2 microglobulin, VEGF, glial cell line-derived neurotrophic factor, chiotriosidase-1, MMP-9, CXC motif chemokine 13, terminal complement complex, chitinase-3-like-protein 1, and osteopontin. (See Vinther-Jensen T, et al., Neruol Neurimmunol Neuroinflamm, 2016, 3(6): e287; and Mishra et al., J. Neuroinflamm., 2017, 14:251 herein incorporated by reference).

14. Combination Stem Cell and Pulsed Dosing Therapy

An embodiment of the invention includes treating a subject diagnosed with a cognitive impairment, impaired motor function, neuroinflammation, or a decline in neurogenesis by administering to the subject an effective amount of blood plasma or Plasma Fraction in a subject who is undergoing, will undergo, or has received stem cell therapy. Another embodiment of the invention includes administering to a subject an effective amount of blood plasma or Plasma Fraction where the subject is undergoing, will undergo, or has received stem cell therapy, and wherein the stem cells used in the therapy can be embryonic stem cells, non-embryonic stem cells, induced pluripotent stem cells (iPSCs), cord blood stem cells, amniotic fluid stem cells, and the like.

Stem cell therapy and techniques to perform such therapy are known to those having ordinary skill in the art. (Andres R H, et al., Brain 2011, 134; 1777-89; Daadi M M, et al., Cell Transplant 2013, 22(5):881-92; Horie N, et al., Stem Cells 2011 29(2):doi: 10.1002/stem.584; Thomsen G M, et al., Stem Cells 2018, doi: 10.1002/stem.2825; U.S. patent application Ser. Nos. 09/973,198; 12/258,210; 12/596,884; and 13/290,439, which are all incorporated herein by reference). Another embodiment of the invention includes treating a subject diagnosed with traumatic spinal cord injury, stroke, retinal disease, Huntington's disease, Parkinson's Disease, Alzheimer's Disease, hearing loss, heart disease, rheumatoid arthritis, severe burns, or is in need of a bone marrow transplant and who is undergoing, will undergo, or has received stem cell therapy, with an effective amount of blood plasma or Plasma Fraction.

15. Methods of Screening Compositions

Also provided are methods of screening compositions for activity in treating cognitive or motor impairment, reducing neuroinflammation, or increasing neurogenesis. Such methods are contemplated by the invention and include those methods described in the experimental examples below. Compositions that may be screened by embodiments of the invention include: biological compositions (e.g. proteins, combinations of proteins, antibodies, small molecule antagonists); Plasma Fractions, or other blood compositions. Results from the methods of screening compositions include, but are not limited to: results of inflammation/inflammatory markers in the hippocampus (e.g. dentate gyrus) or other CNS regions; results of cell proliferation in the hippocampus or other CNS regions; cell survival in the hippocampus or other CNS regions; the cell fate (e.g. astrocytes, new neurons) of proliferating neuroprogenitor cells (NPCs) in the hippocampus or other CNS regions; and neurogenesis in the hippocampus or other CNS regions.

Additional embodiments of methods of screening compositions for activity in treating cognitive or motor impairment, reducing neuroinflammation, or increasing neurogenesis include determining acute effects of compositions on hippocampus inflammation and proliferation, comprising: 5-7 consecutive daily doses of BrdU with concurrent 5-7 consecutive daily administration of the composition being screened or control (Pulsed Dosed) in rodents or another animal model. Up to 10 days (i.e. 1, 2, 3, 4, 5, 6, 7, 8, 9, or 10 days) after conclusion of pulsed dosing of the composition being screened, the number of cells in the dentate gyrus is determined by BrdU staining, and the percent area exhibiting CD-68 staining (an indicator of inflammation) is determined.

Another embodiment of methods of screening compositions for activity in treating cognitive or motor impairment, reducing neuroinflammation, or increasing neurogenesis include administering BrdU for 5 consecutive days (once per day) before commencing a Pulsed Dosing regimen of 5-7 days of the composition being screened or control in rodents or other animal model. Four, five, six, seven, eight, nine, ten, eleven, or twelve weeks subsequently, hippocampus cell survival is determined as the number of cells in the dentate gyrus staining with BrdU, neurogenesis is determined as the number of cells in the dentate gyrus staining with doublecortin (DCX), and cell fate of neuroprogenitor cells becoming either astrocytes (associate with aging) or neurons (not associated with aging) are determined by co-localization of BrdU with GFAP or NeuN markers, respectively.

Another embodiment of methods of screening compositions for activity in treating cognitive or motor impairment, reducing neuroinflammation, or increasing neurogenesis include administering BrdU and the composition being screened or control concurrently (and daily) for 5-7 days, and subsequently determining the degree of neurogenesis by DCX staining in the hippocampus or cell fate of proliferating NPCs as described above.

Another embodiment of methods of screening compositions for activity in treating cognitive or motor impairment, reducing neuroinflammation, or increasing neurogenesis include administering a Pulsed Dose regimen of the composition to be screened or control, and determining improvement in cognitive or motor function in rodents or another animal model as described in the examples below.

16. Reagents, Devices, and Kits

Also provided are reagents, devices, and kits thereof for practicing one or more of the above-described methods. The subject reagents, devices, and kits thereof may vary greatly.

Reagents and devices of interest include those mentioned above with respect to the methods of preparing plasma-comprising blood product for transfusion into a subject in need hereof, for example, anti-coagulants, cryopreservatives, buffers, isotonic solutions, etc.

Kits may also comprise blood collection bags, tubing, needles, centrifugation tubes, and the like. In yet other embodiments, kits as described herein include two or more containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

17. Exercise

Exercise can be characterized by aerobic or anaerobic activity, and can involve high calorie-burning activity and moderate calorie-burning activity. Exercise may involve strength training (e.g. weight training or isometric exercise). Exercise may also involve, for example, running, bicycling, walking, dancing, marching, swimming, yoga, Tai Chi, balance exercises, leg bends, jumping rope, surfing, rowing, rotating or flexing the arms or legs, gardening, cleaning, active games such as bowling, aerobics, Pilates, and martial arts.

An exercise regimen may include performing a single exercise at a certain frequency, or a combination of exercises at a certain frequency. The frequency may be one, two, three, four, five, six, or seven times per week. The frequency may vary from week-to-week. The exercise regimen may be at the same level of intensity and/or frequency as the subject practiced before administration of the compositions of the invention. The exercise regimen may also be at a higher level of intensity and/or frequency compared to the levels the subject practiced before administration of the compositions of the invention. The exercise regimen may have been suggested or prescribed by a health or fitness professional, or the exercise regimen may have been initiated by the subject himself or herself.

18. Experimental Examples a. Example 1

Clarified young human plasma (young plasma) or a commercially-available PPF ("PPF1") was administered to aged immunocompromised mice (NOD.Cg-Prkdscid Il2rgtm 1 Wj1/SzJ, "NSG" strain). PPF1 is a PPF with approximately 88% normal human albumin (in relation to total protein), 12% alpha and beta globulins, and no more than 1% gamma globulin as determined by electrophoresis. Except where noted, PPF1 is administered in the examples herein in vivo using a 5% solution (w/v, 50 g/L). All mice were homogenized across treatment groups according to 4 different criteria: home cage nestlet scoring, initial body weight, open field distance traveled, and % center time in open field. Following group determination, mice were injected intraperitoneally (IP) with BrdU (5-bromo-2'-deoxyuridine) formulated in PBS (Phosphate buffered saline) at a final concentration of 10 mg/mL dosed at 150 mg/kg for 5 days. Following this, mice were injected intravenously (IV) 3 times weekly with 150 μL of PPF1 for 4 weeks. Behavior testing occurred in weeks 5 and 6, where mice received 2 injections per week to avoid injections during concurrent testing days. Mice were euthanized 24 hours after the final IV injection, for a total of 16 injections over a period of 6 weeks. Two additional cohorts of mice were injected intravenously (IV) for seven consecutive days with 150 μL of either PPF1 or saline (Pulse Dosed). Behavior testing occurred in weeks 5 and 6 at the same time as the 3 times per week group.

Behavioral assays were analyzed using CleverSys software (Reston, Va.). CleverSys TopScan V3.0 was used to track mouse behavior in the zero maze, Barnes maze, open field, and Y-maze. Barnes mazes were constructed by CleverSys. The Grip strength meter was designed and produced by Columbus Instruments (Columbus, Ohio). Y-maze and Open field chambers were constructed according to specifications of San Diego Instruments (San Diego, Calif.). Histological analysis of hippocampal sections was performed on Leica (Buffalo Grove, Ill.) imaging microscope model DM5500B with DCF7000T brightfield/fluorescent color microscope camera.

Figure 1B:
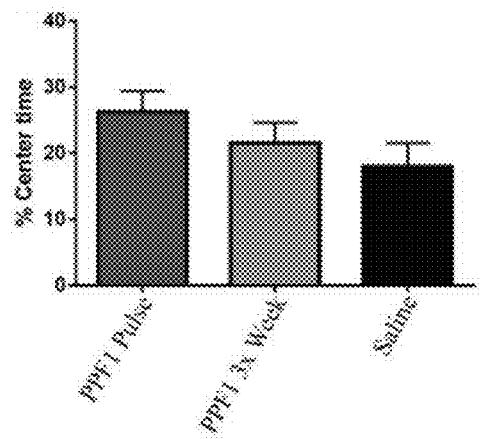
FIG. 1B depicts time spent in the center of the open field in mice treated with PPF1 using Pulse Dose and 3x/week dosing regimens.

Behavioral Testing:

FIG. 1A shows that the groups that were Pulse Dosed with PPF1 trended towards increased distance traveled in the open field test as compared to both the saline control group and the group treated three times weekly with PPF1. This result indicates a trend towards increased motility in the Pulse Dosed group. FIG. 1B shows that the groups that were Pulse Dosed with PPF1 trended toward increased percentage of time spent in the center of the open field compared to both the saline control group and the group treated three times weekly with PPF1. This result indicates a trend towards decreased anxiety in the Pulse Dosed group.

Figure 2:
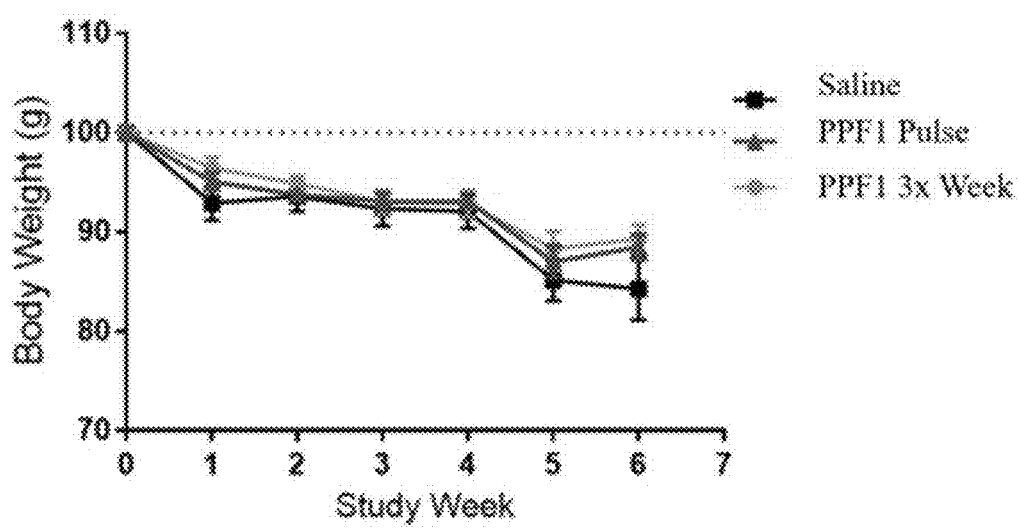
FIG. 2 depicts the body weight over time for mice treated with PPF1 using Pulse Dose and 3x/week dosing regimens.

Body Weight:

FIG. 2 charts the effect of PPF1 on body weight. Both PPF1-treated groups (via Pulsed Dosing or thrice weekly) exhibited no detrimental effects from injection.

Figure 3:
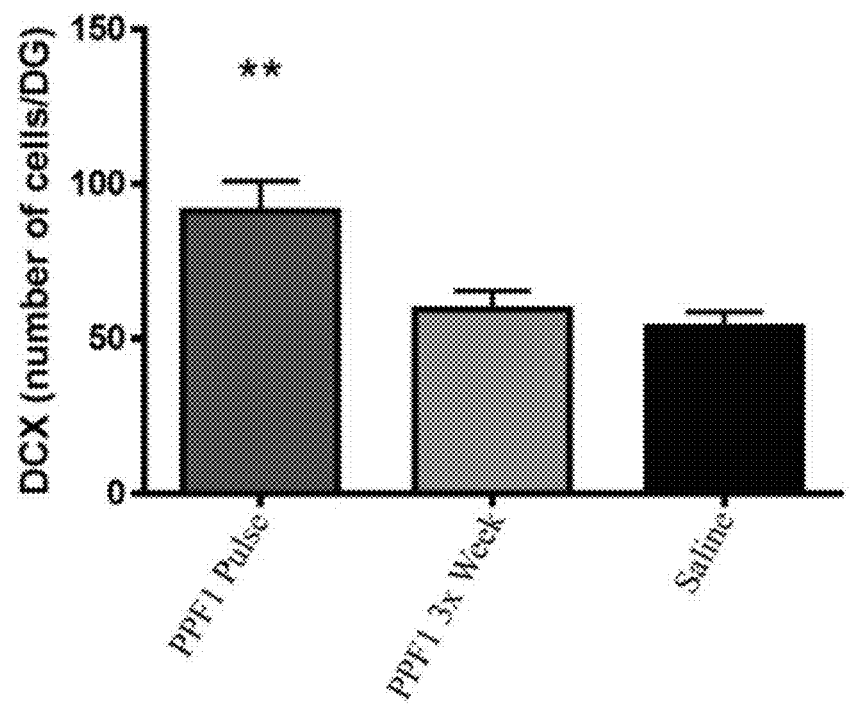
FIG. 3 reports the number of DCX labeled cells within the granule layer of the dentate gyrus in mice treated with PPF1 using Pulse Dose or 3x/week dosing regimens.
Figure 4:
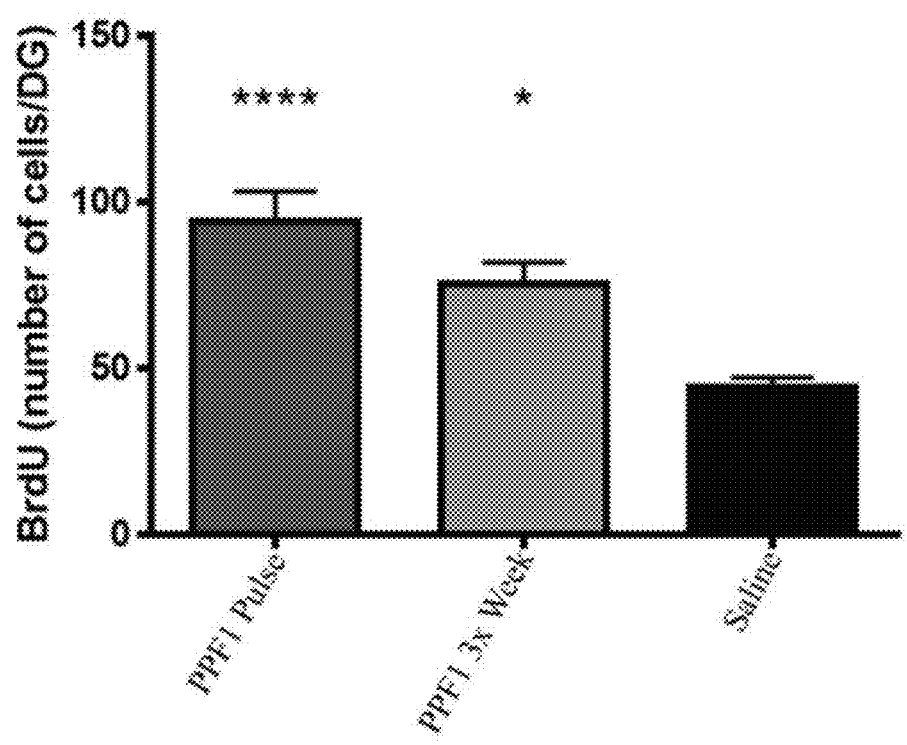
FIG. 4 reports the number of BrdU labeled cells within the granule layer of the dentate gyrus in mice treated with PPF1 using Pulse Dose or 3x/week dosing regimens.

Histology:

FIG. 3 reports the number of DCX positively-labeled cells within the granule layer of the dentate. There was a significant increase in neurogenesis between the Pulsed Dose PPF1-treated group compared to the thrice weekly treated group and saline group. All data shown are mean±s.e.m. $P<0.01$ One-Way ANOVA with Dunnett's multiple comparison Post-Hoc analysis (n: saline=8, PPF1 Pulsed Dosed=10, PPF1 3x/week=10). FIG. 4 reports the number of BrdU positively-labeled cells within the granule layer of the dentate gyrus of three separately treated groups of mice. There was a significant increase in cell survival between the Pulsed Dose PPF1-treated group compared to the thrice weekly treated group and saline group. All data shown are mean±s.e.m. **$P<0.0001$, * $P<0.05$ One-Way ANOVA with Dunnett's multiple comparison Post-Hoc analysis (n: saline=8, PPF1 Pulsed=10, PPF1 3x/week=10).

Analysis of hippocampal sections was performed on Leica (Buffalo Grove, Ill.) imaging microscope model DM5500B with DCF7000T brightfield/fluorescent color microscope camera. Ki67 staining Abcam (ab15580) at 1:500 and secondary is goat anti rabbit (Alex Fluor 555) (ab150090) at 1:300.

b. Example 2

Clarified young human plasma (YP), old human plasma (OP) or a Commercially-available PPF ("PPF1") were administered to aged immunocompromised mice (NOD.Cg-Prkdscid Il2rgtm 1 Wj1/SzJ, "NSG" strain). All mice were homogenized across treatment groups according to 4 different criteria: home cage nestlet scoring, initial body weight, open field distance traveled, and % center time in open field. Following group determination, mice were injected intraperitoneally (IP) with BrdU formulated in PBS (Phosphate buffered saline) at a final concentration of 10 mg/mL dosed at 150 mg/kg for 5 days. Following this, mice were injected intravenously (IV) either: 1) Three times per week for 6 weeks ("3x/Week"); 2) Three times in one week only ("3x"); 3) 7 days in one week with 150 µL of either clarified young human plasma or PPF1. An additional group of mice was administered saline pulsed for 7 days IV. The final group of mice received aged human plasma for either 3 times in one week or for 7 days in one week. All mice were sacrificed 6 weeks after the initiation of young or aged plasma, PPF1 or vehicle dosing.

Figure 5:
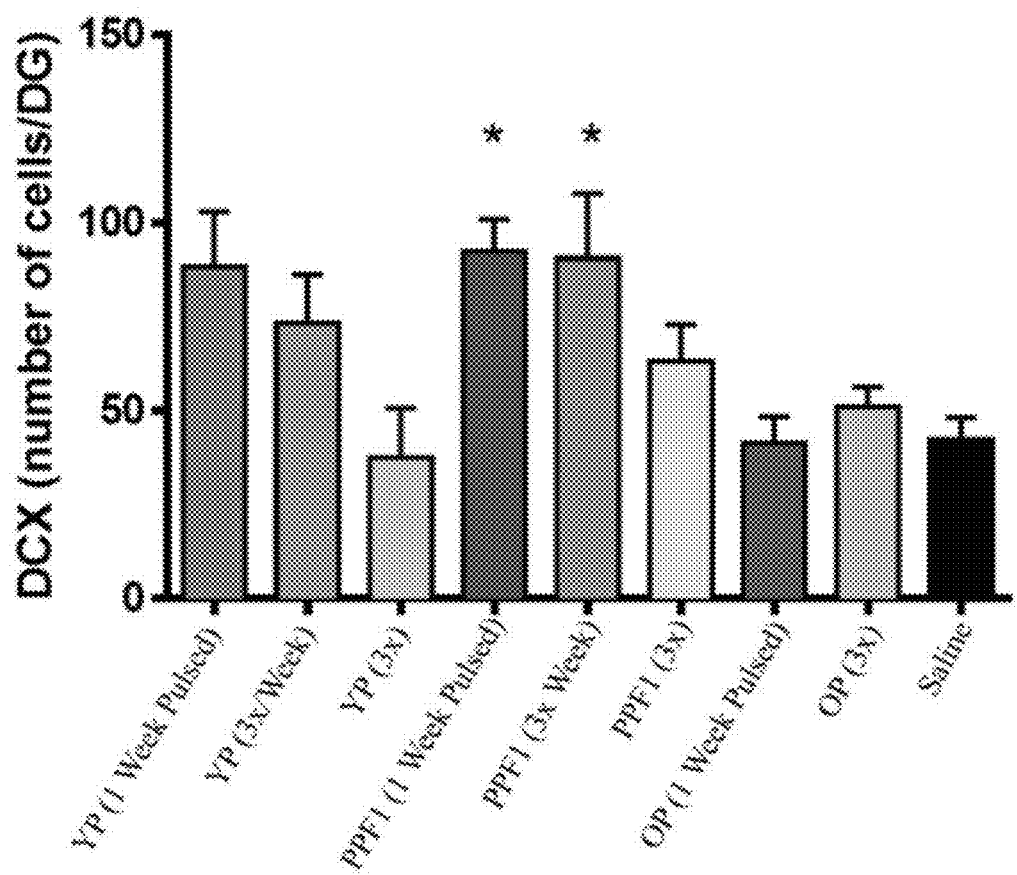
FIG. 5 reports the number of DCX labeled cells within the granule layer of the dentate gyrus in mice treated with PPF1 using Pulse Dose or 3x/week dosing regimens, young human plasma ("YP"), or old human plasma ("OP").

Histology:

FIG. 5 reports the number of DCX positively-labeled cells within the granule layer of the dentate gyrus of nine separately treated groups of mice treated with either young human plasma (YP), old human plasma (OP), PPF1, or saline. PPF1-treated mice either Pulse Dosed or treated thrice weekly both exhibited increased neurogenesis compared to the other groups. All data shown are mean±s.e.m; *$P<0.05$, ANOVA with Dunnett's post-hoc analysis PPF1 (pulsed or 3x/week) treatment and saline treatment (n: saline=4, PPF1 pulsed=5, PPF1 3x/week=5, PPF1 3x=4, YP pulsed=6, YP 3x/week=6, YP 3x=4, AP pulsed=6, AP 3x=6)

Figure 6:
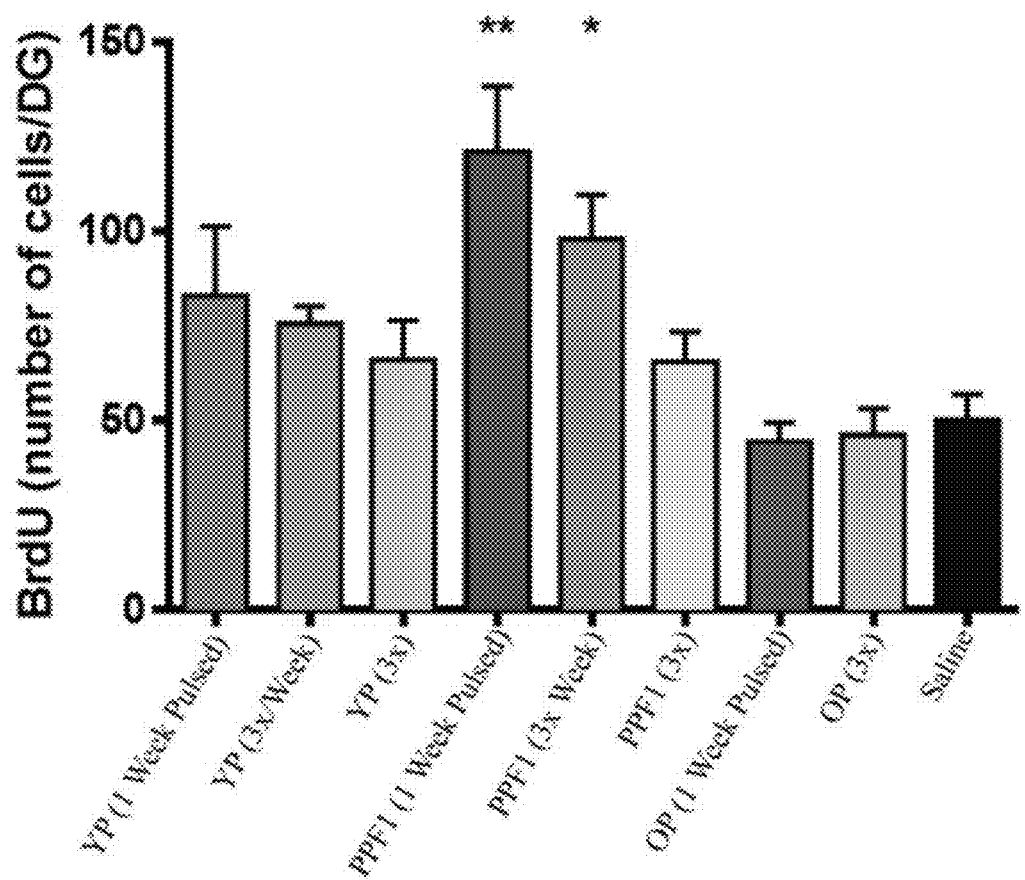
FIG. 6 reports the number of BrdU labeled cells within the granule layer of the dentate gyrus in mouse groups treated with PPF1 using Pulse Dose or 3x/week dosing regimens, YP, or OP.

FIG. 6 reports the number of BrdU positively-labeled cells within the granule layer of the dentate gyrus of nine separately treated groups of mice treated with either young human plasma (YP), old human plasma (OP), PPF1, or saline. PPF1-treated mice exhibited a significant increase in cell survival compared to the other groups, with Pulse-Dosed PPF1-treated mice exhibiting a larger significant difference than thrice weekly dosed PPF1-treated mice. All data shown are mean±s.e.m; **$P<0.01$, *$P<0.05$, ANOVA with Dunnett's post-hoc analysis PPF1 (pulsed or 3x/week) treatment and saline treatment (n: saline=4, PPF1 pulsed=5, PPF1 3x/week=5, PPF1 3x=4, YP pulsed=6, YP 3x/week=6, YP 3x=4, AP pulsed=6, AP 3x=6).

c. Example 3

Clarified young human plasma (YP), old human plasma (OP) or a commercially-available PPF ("PPF1") were administered to aged immunocompromised mice (NOD.Cg-Prkdscid Il2rgtm 1 Wj1/SzJ, "NSG" strain). Mice were treated with 7 daily intravenous (IV) doses in a 1 week regimen.

All mice were homogenized across treatment groups according to 4 different criteria: home cage nestlet scoring, initial body weight, open field distance traveled, and % center time in open field. Following group determination, mice were injected intraperitoneally (IP) with BrdU formulated in PBS (Phosphate buffered saline) at a final concentration of 10 mg/mL dosed at 150 mg/kg for 5 days. All mice were injected intravenously (IV) for seven consecutive days (referred to as Pulsed dosing) with 150 uL of young or aged human plasma, PPF1 or saline. Three weeks after pulsed dosing was completed, mice were injected intraperitoneally (IP) with EdU (5-ethynyl-2'-deoxyuridine) formulated in PBS (Phosphate buffered saline) at a final concentration of 10 mg/mL dosed at 30 mg/kg for 5 days. Barnes maze was performed during week 8 (6 weeks following the end of pulse dosing).

Behavioral assays were analyzed using CleverSys software (Reston, Va.). CleverSys TopScan V3.0 was used to track mouse behavior in the Barnes maze. Barnes maze was constructed by CleverSys. Analysis of hippocampal sections was performed on Leica (Buffalo Grove, Ill.) imaging microscope model DM5500B with DCF7000T brightfield/fluorescent color microscope camera.

Figure 7:
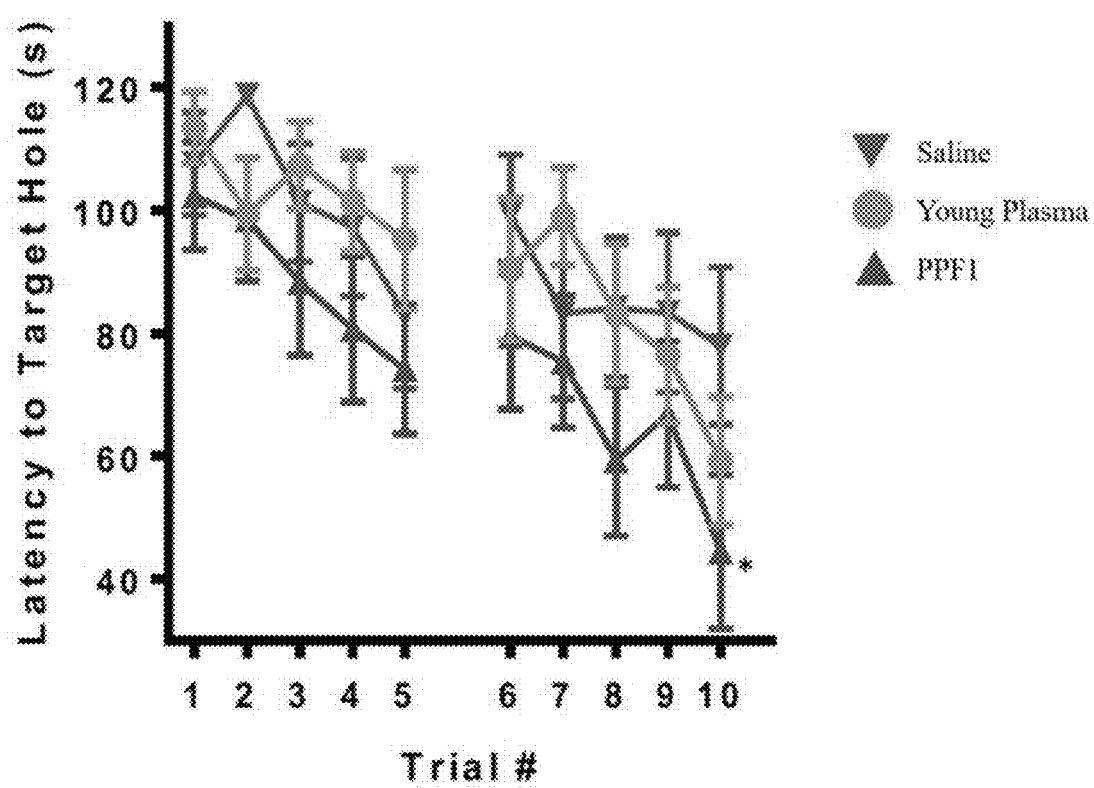
FIG. 7 reports the latency to find the target hole per trial per day for mice Pulse Dosed with PPF1 or YP.

Behavioral Testing:

FIG. 7 reports the latency to find the target hole per trial per day for each treatment group as tested by Barnes Maze. PPF1 Pulsed Dosed-treated mice exhibited significant decrease in trial latency for several individual testing sessions, indicating improved cognitive ability. *$P<0.05$ mean±s.e.m; unpaired t-test (n: saline=13, PPF1=13, AP=14, YP=14).

Figure 8:
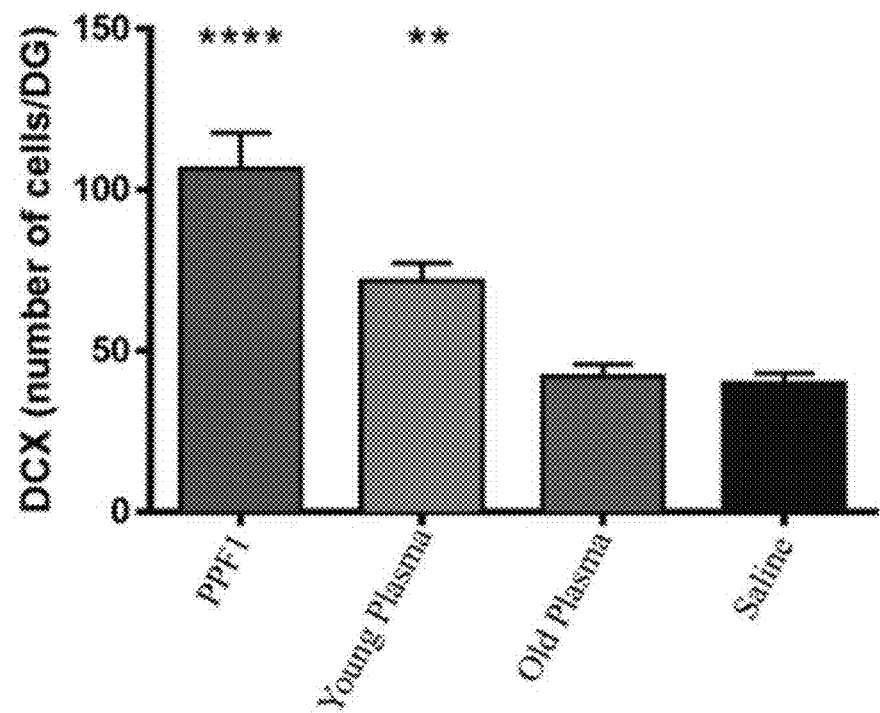
FIG. 8 reports the number of DCX labeled cells within the granule layer of the dentate gyrus in groups of mice treated with either young human plasma (YP), old human plasma (OP), or PPF1 using a Pulse Dosed regimen.

Histology:

FIG. 8 reports the number of DCX positively-labeled cells within the granule layer of the dentate gyrus of four separately treated groups of mice treated with either young human plasma (YP), old human plasma (OP), PPF1, or saline. There were significant increases in neurogenesis in Pulsed Dosed PPF1 and Pulse Dosed young human plasma as compared to saline treatment. All data shown are mean±s.e.m; **P<0.0001, P<0.01, One-Way ANOVA with Dunnett's multiple comparison Post-Hoc analysis. (n: saline=14, PPF1=14, AP=14, YP=15)

Figure 9:
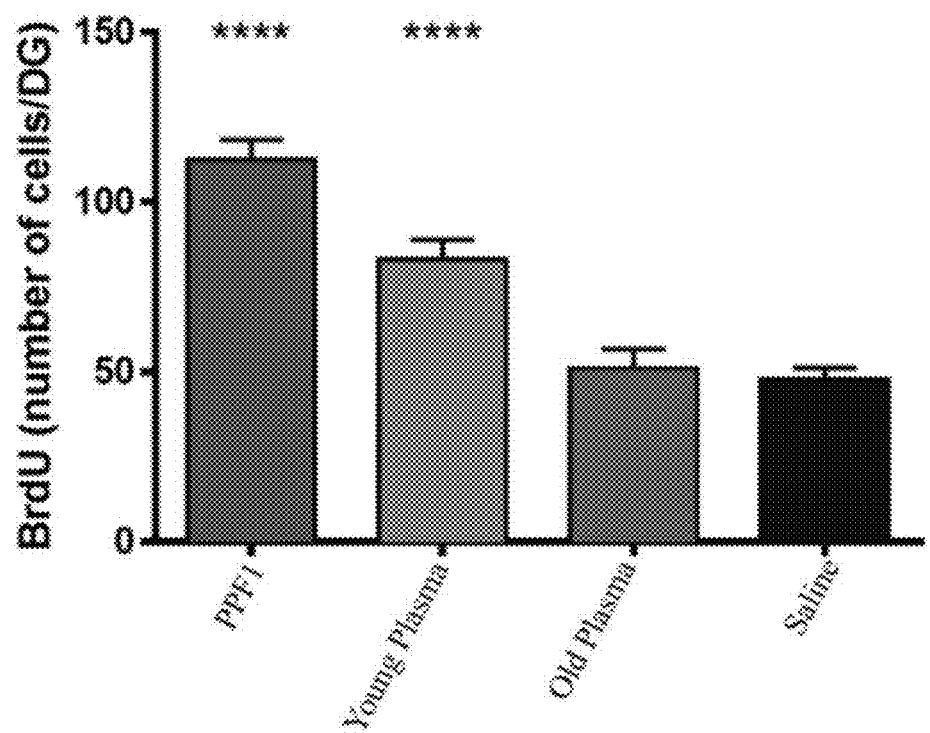
FIG. 9 reports the number of BrdU labeled cells within the granule layer of the dentate gyrus in groups of mice treated with either young human plasma (YP), old human plasma (OP), or PPF1 using a Pulse Dosed regimen.

FIG. 9 reports the number of BrdU labeled cells within the granule layer of the dentate gyrus of mice treated with either young human plasma (YP), old human plasma (OP), PPF1, or saline. There were significant increases in cell survival in Pulsed Dosed PPF1 and Pulse Dosed YP as compared to saline treatment. All data shown are mean±s.e.m; ****P<0.0001; mean±s.e.m; One-Way ANOVA with Dunnett's multiple comparison Post-Hoc analysis. (n: saline=14, PPF1=14, AP=14, YP=15).

d. Example 4

A Commercially-available PPF ("PPF1") was administered to aged immunocompromised mice (NOD.Cg-Prkdscid Il2rgtm 1 Wj1/SzJ, "NSG" strain). Twelve-month-old mice were treated with a 7-daily tail vein intravenous (IV) doses in 1 week regimen. After treatment, the mice were allowed to remain in their home cage environment for 4.5 weeks prior to behavior testing. All injections and behavioral testing took place over the course of 7 weeks for each cohort and conducted over a total span of 9 weeks. All mice received BrdU IP for 5 days prior to first dosing. Mice were sacrificed one day following the conclusion of the last behavior test.

Behavioral assays were analyzed using CleverSys software (Reston, Va.). CleverSys TopScan V3.0 was used to track mouse behavior in the Y-maze.

Figure 10:
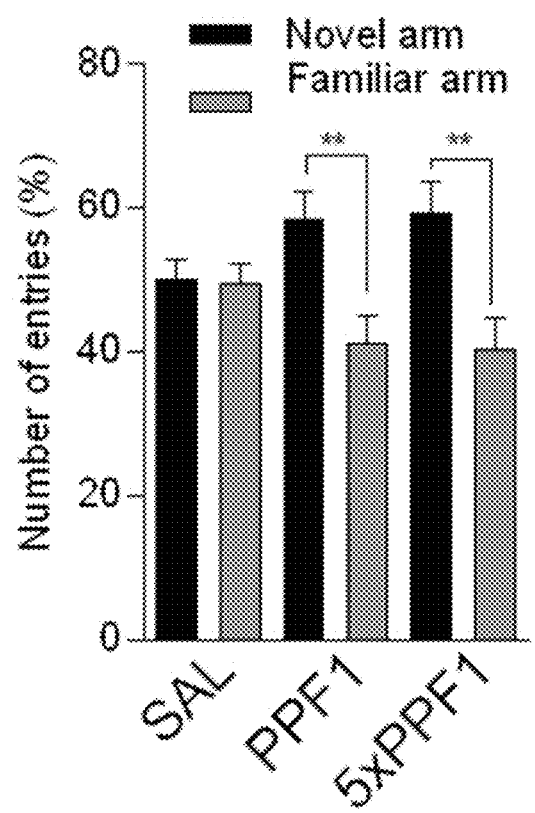
FIG. 10 reports the percent of total number of entries made into either the familiar or novel arm of total entries made into each arm by treatment group in the Y-maze test. Twelve-month-old mice were Pulse Dose treated with PPF1 or 5x concentrated PPF1.

Behavioral Testing:

FIG. 10 reports the percent of total number of entries made into either the familiar or novel arm of total entries made into each arm by treatment group in the Y-maze test. Twelve-month-old mice were Pulse Dose treated with saline, PPF1, or 5x concentrated PPF1. PPF1 and PPF1 (5x) Pulse Dose treated mice both showed a significant increase in entering the novel arm compared to the amount of entries into the novel arm by saline treated mice, indicating an improvement in cognition. All data shown are mean±s.e.m. *P<0.05, paired t-test.

Figure 11:
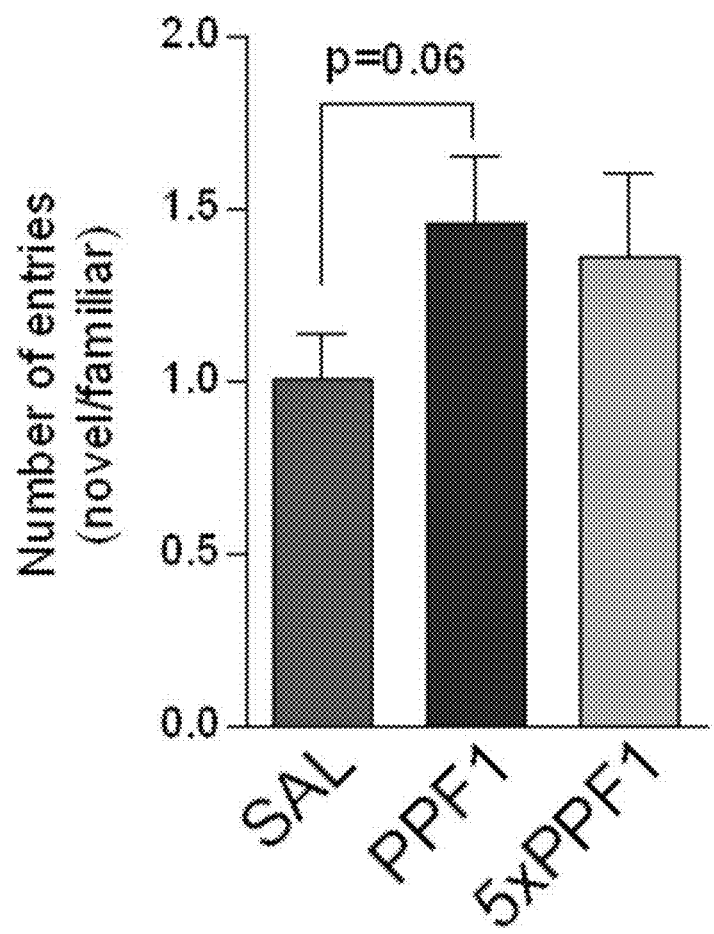
FIG. 11 reports the ratio of bouts into the novel versus the familiar arm of the Y-maze test. Twelve-month-old mice were Pulse Dose treated with PPF1 or 5x concentrated PPF1.

FIG. 11 reports the ratio of bouts into the novel versus the familiar arm of the Y-maze for each treatment group. Twelve-month-old mice were Pulse Dose treated with saline, PPF1, or 5x concentrated PPF1. PPF1 and PPF1 (5x) Pulse Dose treated mice both exhibited a trend in increased entry into the novel arm compared to saline treated mice. All data shown are mean±s.e.m.

Figure 12:
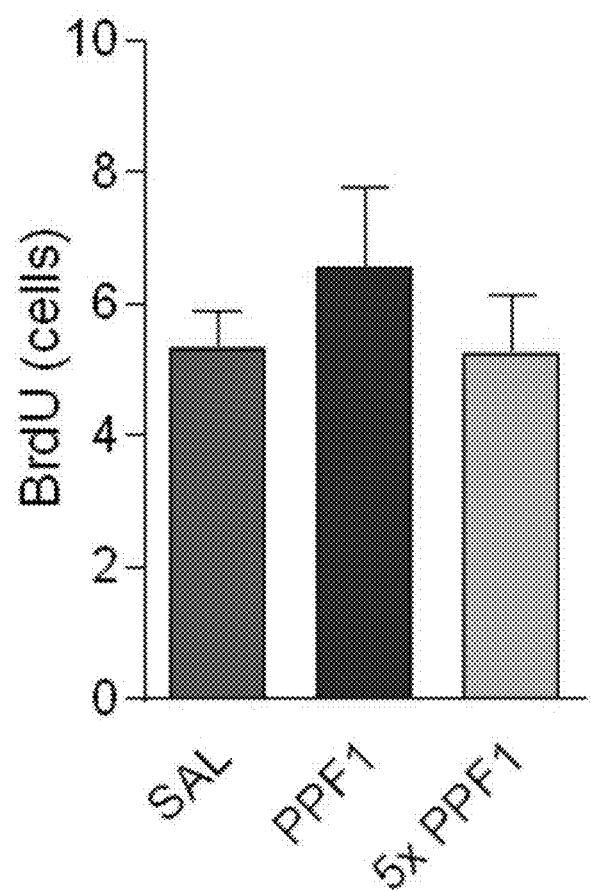
FIG. 12 reports the number of BrdU labeled cells per hippocampal section in twelve-month-old mice that were Pulse Dosed with PPF1 or 5x concentrated PPF1.

Histology:

FIG. 12 reports the number of BrdU positively-labeled cells within all hippocampal sections. PPF1 Pulse Dosed mice exhibited a trend for increased cell survival compared to saline and PPF1 (5x) treated mice. All data shown are mean±s.e.m.

Figure 13:
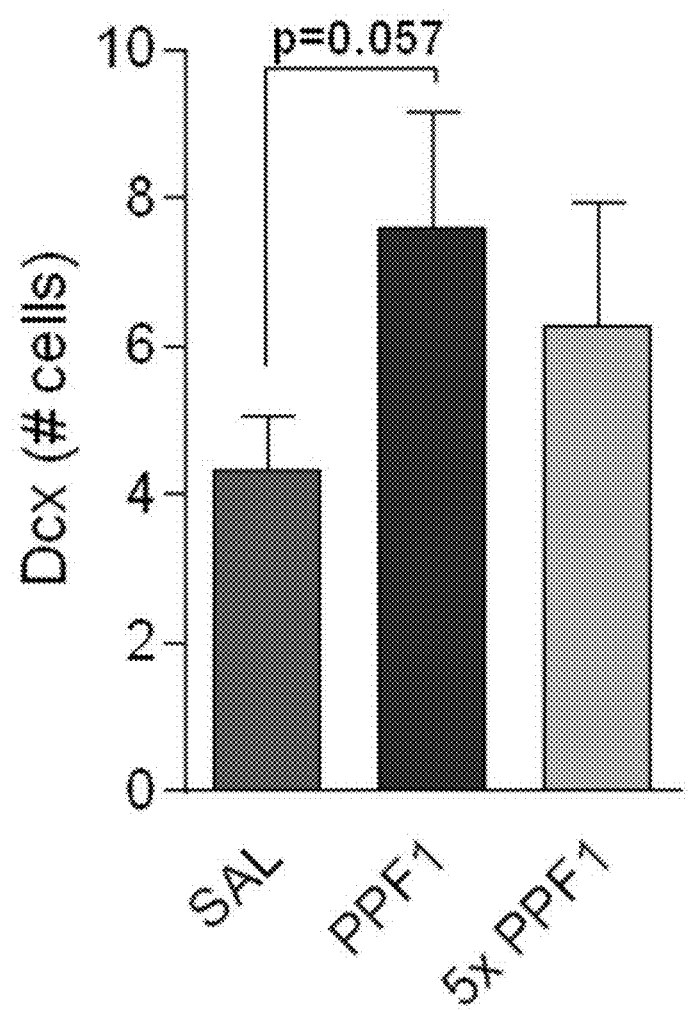
FIG. 13 reports the number of DCX labeled cells per hippocampal section in twelve-month-old mice that were Pulse Dosed with PPF1 or 5x concentrated PPF1.

FIG. 13 reports the number of DCX positively-labeled cells within all hippocampal sections. PPF1 and PPF1 (5x) Pulse Dosed mice exhibited a trend for increased neurogenesis compared to saline treated mice. All data shown are mean±s.e.m.

e. Example 5

Commercially-available PPF ("PPF1") was administered to aged (10.5-month-old) immunocompromised mice (NOD.Cg-Prkdscid Il2rgtm 1 Wj1/SzJ, "NSG" strain). All mice were homogenized across treatment groups according to four different criteria: home cage nestlet scoring, initial body weight, open field distance traveled, and percent center time in open field. Following group determination, mice were injected intraperitoneally (IP) with BrdU formulated in PBS (Phosphate buffered saline) at a final concentration of 10 mg/mL dosed at 150 mg/kg for 5 days. Following this, mice were injected PPF1 intravenously (IV) for either: 1) 5 sequential days [PPF1-5d] 2) 7 sequential days [PPF1-7d] 3) 5 sequential days with an additional 5 sequential days of boosted (B) dosing occurring 6 weeks after the completion of the initial dosing [PPF1-5d-B] 4) 7 sequential days with an additional 7 sequential days of boosted (B) dosing occurring 6 weeks after the completion of the initial dosing [PPF1-7d-B]. An additional group were injected with saline for 7 sequential days with an additional 7 sequential days of dosing occurring 6 weeks after the completion of the initial dosing [SAL-7d-B]. Five weeks after pulsed dosing, mice were injected IP with EdU (5-ethynyl-2'-deoxyuridine) formulated in PBS at a final concentration of 10 mg/mL dosed at 30 mg/kg for 5 days. All mice were sacrificed 12 weeks after the completion of pulse dosing PPF1 or vehicle.

Figure 14:
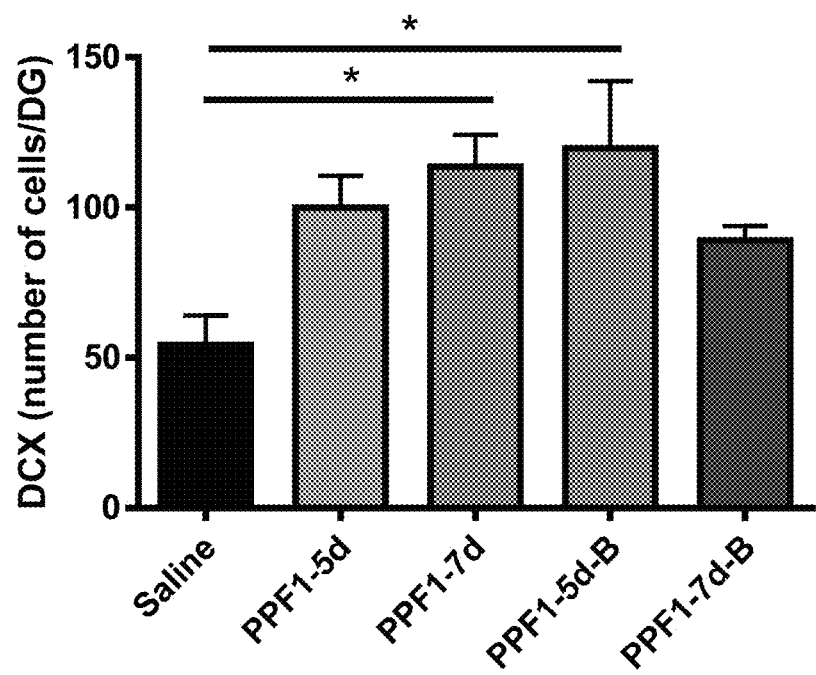
FIG. 14 reports the number of DCX labeled cells within the granule layer of the dentate gyrus in 10.5 month-old NSG mice that were Pulse Dosed with PPF1 or saline using one of the following regimens: (1) 5 sequential days [PPF1-5d]; (2) 7 sequential days [PPF1-7d]; (3) 5 sequential days with an additional 5 sequential days ("booster") of dosing occurring 6 weeks after the completion of the initial dosing [PPF1-5d-B]; or (4) 7 sequential days with an additional 7 sequential days ("booster") of dosing occurring 6 weeks after the completion of the initial dosing [PPF1-7d-B].

Analysis of hippocampal sections was performed on Leica (Buffalo Grove, Ill.) imaging microscope model DM5500B with DCF7000T brightfield/fluorescent color microscope camera. FIG. 14 reports the number of DCX positively labeled cells within the granule layer of the dentate gyrus in PPF1 and saline-treated animals. These results show that there is a significant improvement in the group treated for 5 sequential days followed by a booster, which is comparable to the group treated for 7 sequential days. All data shown are mean±s.e.m; PPF1-7d, PPF1-5d-B vs. saline *P<0.05, ANOVA with Dunnett's post-hoc analysis (n: saline=5, PPF1-5d=8, PPF1-7d=7, PPF1-5d-B=8, PPF1-7d-B=7).

Figure 15:
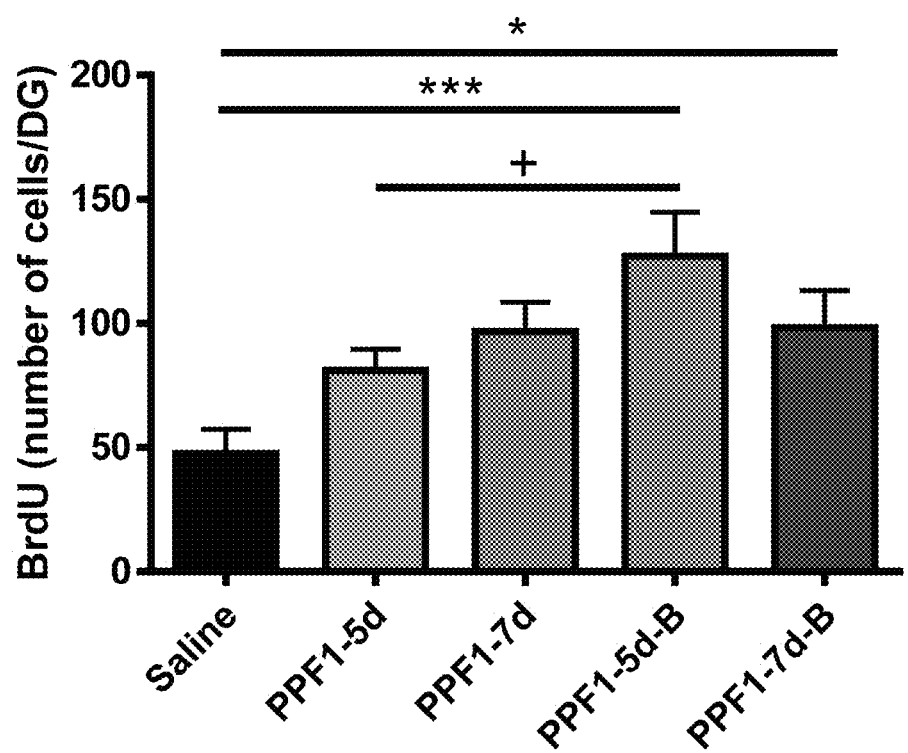
FIG. 15 reports the number of BrdU labeled cells within the granule layer of the dentate gyrus in 10.5 month-old NSG mice that were Pulse Dosed with PPF1 or saline using one of the following regimens: (1) 5 sequential days [PPF1-5d]; (2) 7 sequential days [PPF1-7d]; (3) 5 sequential days with an additional 5 sequential days ("booster") of dosing occurring 6 weeks after the completion of the initial dosing [PPF1-5d-B]; or (4) 7 sequential days with an additional 7 sequential days ("booster") of dosing occurring 6 weeks after the completion of the initial dosing [PPF1-7d-B].

FIG. 15 reports the number of BrdU positively labeled cells within the granule layer of the dentate gyrus in PPF1 and saline-treated animals. These results show that in terms of proliferating cells, inducement increases in earnest in the group treated 5 days sequentially followed by a booster, compared to the groups treated with 5 or 7 sequential days without a booster. Additionally, booster treatment significantly increases cell survival overall. All data shown are mean±s.e.m PPF1-5d-B, PPF1-7d-B vs. saline ***, P<0.001, *P<0.05, ANOVA with Dunnett's post-hoc analysis. PPF1-5d vs. PPF1-5d-B+P<0.05, Unpaired T-Test. (n: saline=7, PPF1-5d=8, PPF1-7d=7, PPF1-5d-B=8, PPF1-7d-B=7).

Figure 16:
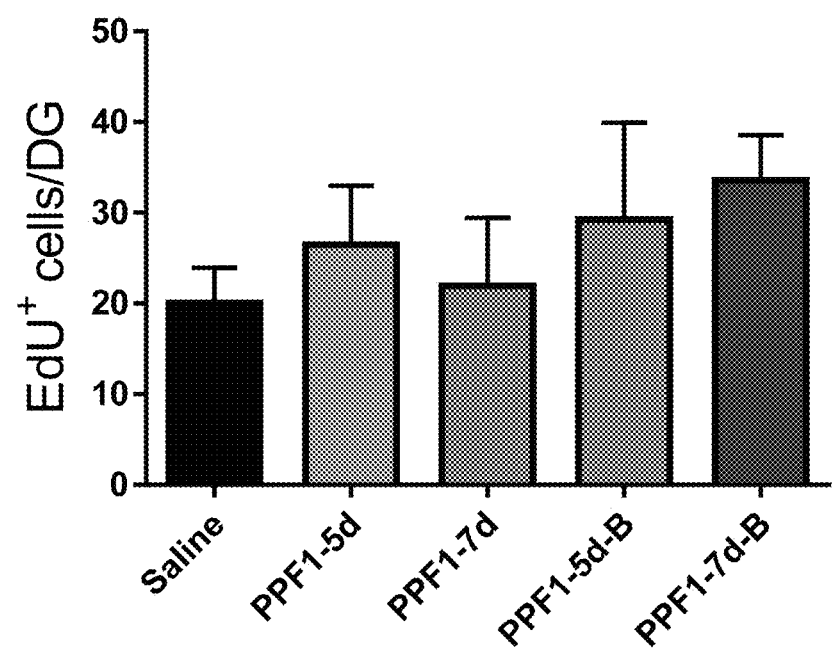
FIG. 16 reports the number of EdU labeled cells within the granule layer of the dentate gyrus in 10.5 month-old NSG mice that were Pulse Dosed with PPF1 or saline using one of the following regimens: (1) 5 sequential days [PPF1-5d]; (2) 7 sequential days [PPF1-7d]; (3) 5 sequential days with an additional 5 sequential days ("booster") of dosing occurring 6 weeks after the completion of the initial dosing [PPF1-5d-B]; or (4) 7 sequential days with an additional 7 sequential days ("booster") of dosing occurring 6 weeks after the completion of the initial dosing [PPF1-7d-B].

FIG. 16 reports the number of EdU positively labeled cells within the granule layer of the dentate gyrus in young plasma, PPF1 and saline-treated animals. These results show that the effects observed with booster dosing are not due to an increase in the total number of proliferating cells present, but to an enhanced survival mechanism elicited by booster administration. All data shown are mean±s.e.m; (n: saline=4, PPF1-5d=7, PPF1-7d=6, PPF1-5d-B=7, PPF1-7d-B=6).

f. Example 6

Commercially-available PPF ("PPF1") was administered to adult (3 and 6-month-old) immunocompromised mice (NOD.Cg-Prkdscid Il2rgtm 1 Wj1/SzJ, "NSG" strain). All mice were homogenized across treatment groups according to four different criteria: home cage nestlet scoring, initial body weight, open field distance traveled, and % center time in open field. Following group determination, mice were injected intraperitoneally (IP) with BrdU formulated in PBS (Phosphate buffered saline) at a final concentration of 10 mg/mL dosed at 150 mg/kg for 5 days. Following this, mice were injected with either saline or PPF1 intravenously (IV) for 7 sequential days (pulse dosing). A subset of mice from both saline and PPF1 treatments were provided running wheels in their home cage. Mice were sacrificed either 3 days, 10 days or 42 days post completion of pulse dosing.

Figure 17:
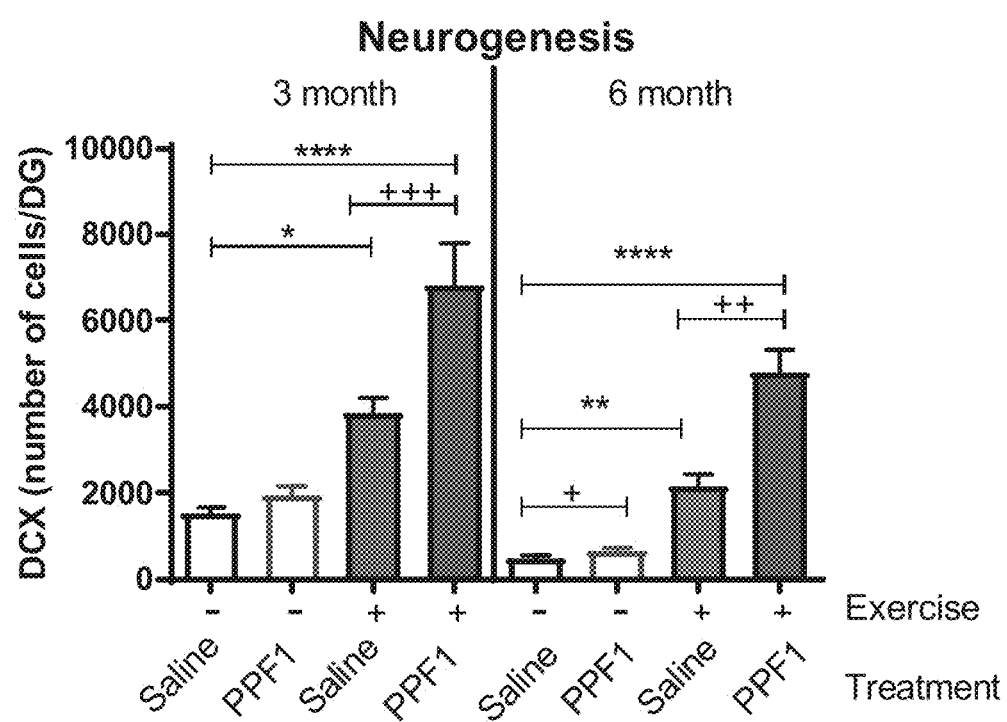
FIG. 17 reports the number of DCX labeled cells within the granule layer of the dentate gyrus in 3 and 6-month-old NSG animals treated with PPF1 or saline with or without running wheels.

FIG. 17 reports the number of DCX positively labeled cells within the granule layer of the dentate gyrus in 3-month-old NSG animals treated with PPF1 or saline-treatment with or without running wheels. All data shown are mean±s.e.m; Running wheel+PPF1 42d post, Running wheel 42d post vs. saline 42d post ****$P<0.0001$, *$P<0.05$, ANOVA with Dunnett's post-hoc analysis. Running wheel vs. PPF1 42d post+++$P<0.001$, Unpaired t-test. (n: saline 3d post=8, PPF1 3d post=8, PPF1 10d post=7, Vehicle 42d post=8, PPF1 42d post=8, Running wheel 42d post=8, Running wheel+PPF1 42d post=8). FIG. 17 also reports the number of DCX positively labeled cells within the granule layer of the dentate gyrus in 6-month-old NSG animals treated with PPF1 or saline-treatment with or without running wheels. All data shown are mean±s.e.m; Running wheel+PPF1 42d post, Running wheel 42d post vs. saline 42d post **$P<0.0001$, $P<0.01$, ANOVA with Dunnett's post-hoc analysis. Running wheel vs. PPF1 42d post+++ $P<0.001$, Unpaired t-test. PPF1 42d post vs. saline 42d post+$P<0.05$, Unpaired t-test. (n: saline 3d post=7, PPF1 3d post=8, PPF1 10d post=6, saline 42d post=8, PPF1 42d post=6, Running wheel 42d post=8, Running wheel+PPF1 42d post=9).

Figure 18:
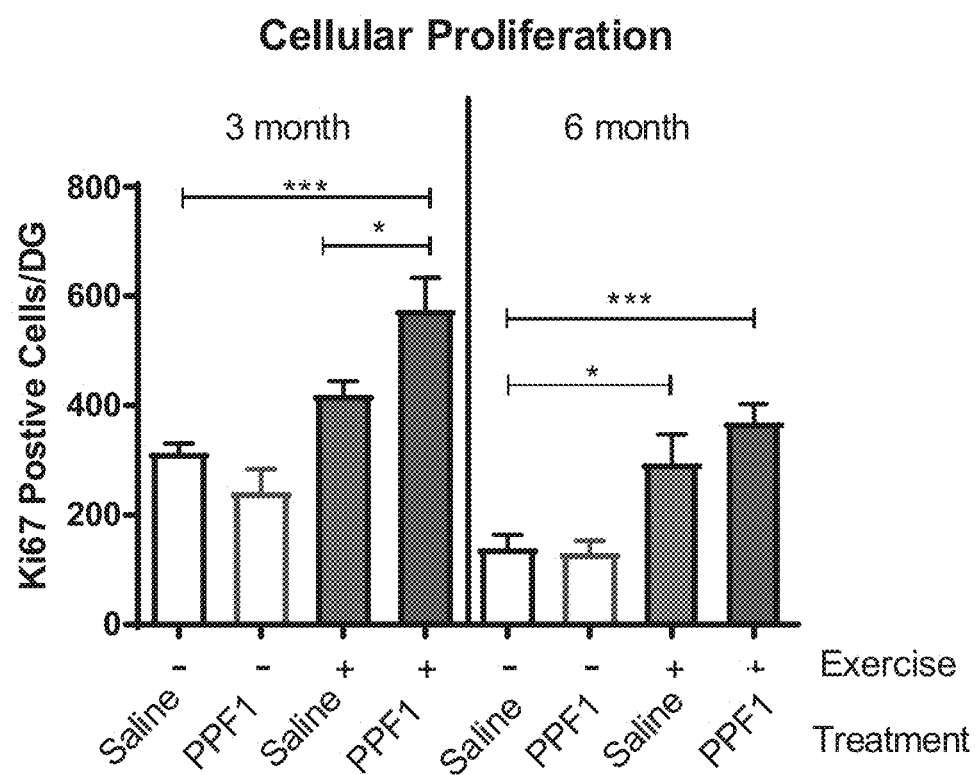
FIG. 18 reports the number of Ki67 positively-labeled cells within the granule layer of the dentate gyrus in 3 and 6-month-old NSG animals treated with PPF1 or saline with or without running wheels.

FIG. 18 reports the number of Ki67 positively labeled cells within the granule layer of the dentate gyrus in 3-month-old NSG animals treated with PPF1 or saline-treatment with or without running wheels. All data shown are mean±s.e.m; Running wheel+PPF1 42d vs. saline 42d post ***$P<0.001$, ANOVA with Dunnett's post-hoc analysis. (n: saline 3d post=6, PPF1 3d post=6, PPF1 10d post=7, saline 42d post=8, PPF1 42d post=8, Running wheel 42d post=8, Running wheel+PPF1 42d post=8).

FIG. 18 also reports the number of Ki67 positively labeled cells within the granule layer of the dentate gyrus in 6-month-old NSG animals treated with PPF1 or saline-treatment with or without running wheels. All data shown are mean±s.e.m; Running wheel+PPF1 42d post, Running wheel 42d post vs. saline 42d post ***$P<0.001$, *$P<0.05$, ANOVA with Dunnett's post-hoc analysis (n: saline 3d post=7, PPF1 3d post=7, PPF1 10d post=8, saline 42d post=8, PPF1 42d post=7, Running wheel 42d post=7, Running wheel+PPF1 42d post=9).

Figure 19:
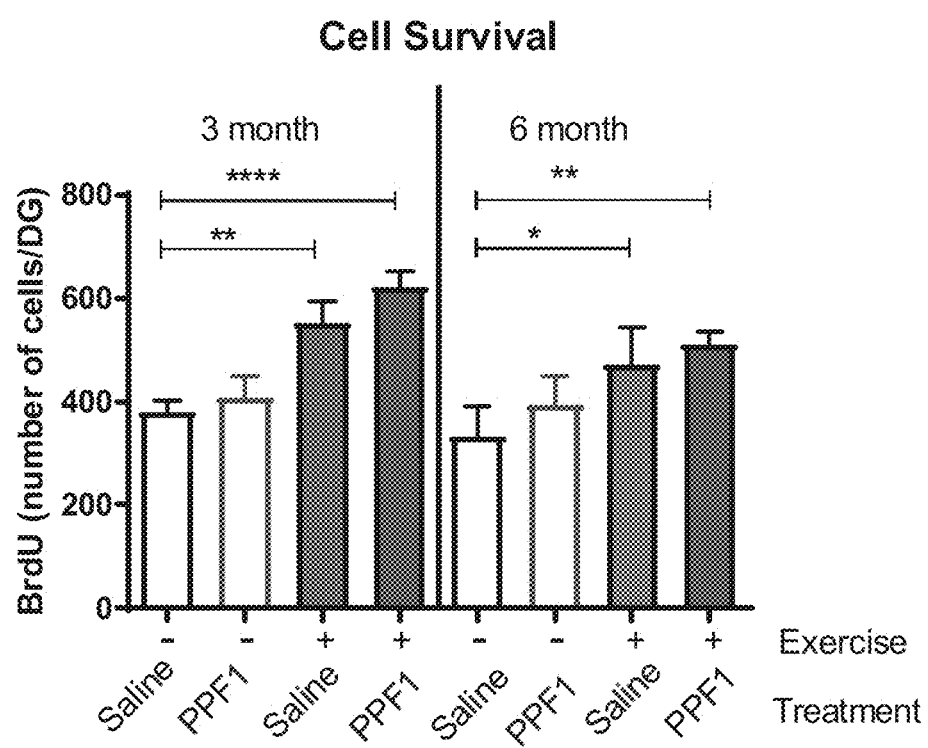
FIG. 19 reports the number of BrdU positively-labeled cells within the granule layer of the dentate gyrus in 3 and 6-month-old NSG animals treated with PPF1 or saline with or without running wheels.

FIG. 19 reports the number of BrdU positively labeled cells within the granule layer of the dentate gyrus in 3-month and 6-month-old NSG animals treated with PPF1 or saline-treatment with or without running wheels. All data shown are mean±s.e.m; Running wheel+PPF1 42d vs. Vehicle 42d post *$P<0.001$, ANOVA with Dunnett's post-hoc analysis. ( $P<0.0001$; * $P<0.001$; ** $P<0.01$; * $P<0.05$, ANOVA with Dunnett's post-hoc analysis).

These results show that there is significant enhancement in neurogenesis with PPF1 and running wheel compared to vehicle 6 weeks post-dosing in 3-month-old NSG mice. Additionally, there is significant enhancement in neurogenesis with PPF1 and running wheel compared to running wheel alone, 6 weeks post dosing in 3-month-old NSG mice. There is also significant enhancement in neurogenesis with PPF1 and running wheel compared to vehicle, 6 weeks post dosing in 6mo old NSG mice. These results also show significant enhancement in neurogenesis with PPF1 and running wheel compared to running wheel alone, 6 weeks post dosing in 6-month-old NSG mice. Further there is significant enhancement in progenitor cell proliferation with PPF1 and running wheel compared to vehicle, 6 weeks post dosing in both 3-month-old and 6-month-old NSG mice.

These findings in adult NSG mice at 6 months of age indicate potential synergistic effects with exercise and PPF1 administration which results in significant enhancement of neurogenesis as compared to either exercise or PPF1 treatments separately. This supports potential utility of PPF1 treatment in conjunction with an exercise regimen in clinical settings. Additionally, these data demonstrate that there is significant capacity for neurogenesis in the brain that can be accessed via multiple independent or overlapping mechanisms.

g. Example 7

PPF1 or saline control were administered to two treatment groups of 11-month-old immunocompromised mice (NOD.Cg-Prkdscid Il2rgtm 1 Wj1/SzJ, "NSG" strain). All mice received IV injections of 150 µL of PPF1 or saline per dose for seven consecutive days. A running wheel (MedAssociates) was placed in the cages of the mice designated as runners (n=8, n=8 for PPF1 and saline) starting on week 7 of the study. The number of wheel revolutions was recorded for 5 consecutive days, day and night.

Figure 20:
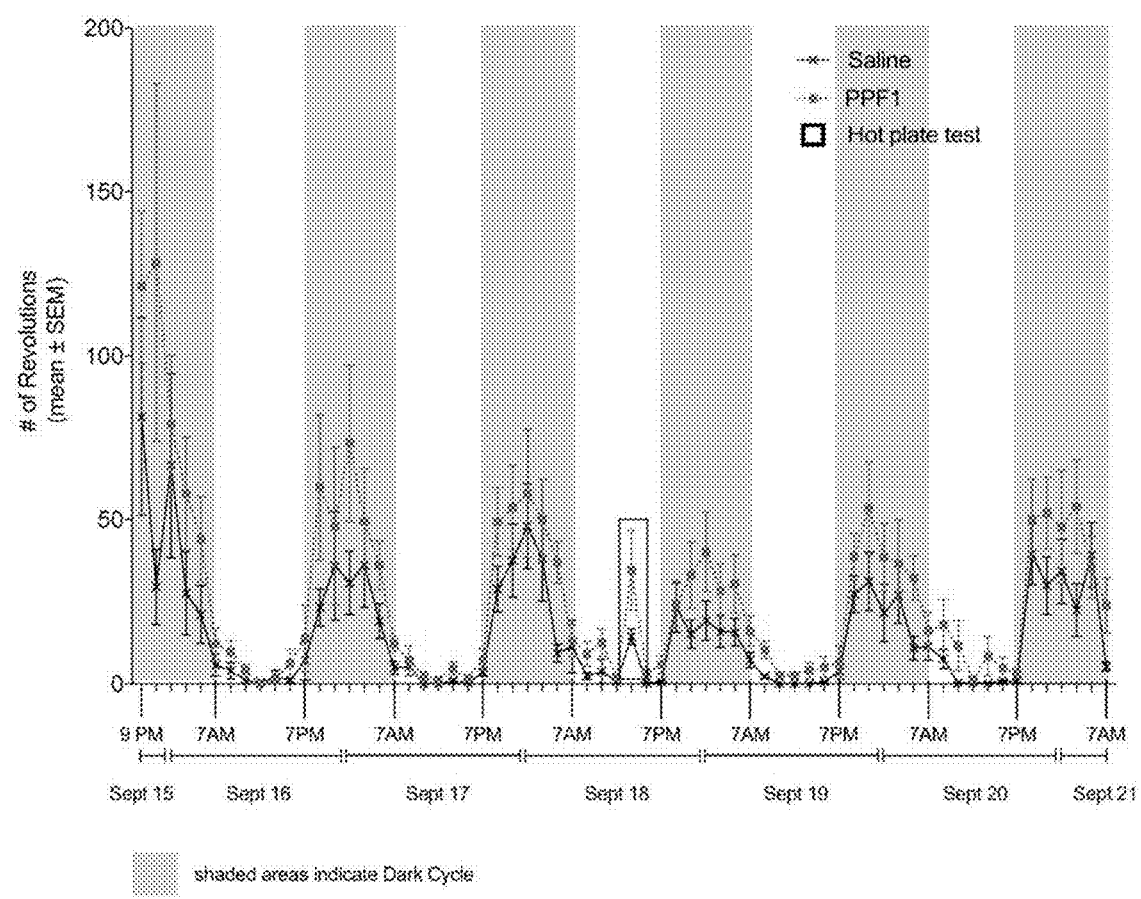
FIG. 20 reports the number of wheel revolutions during given time periods in 11-month-old NSG mice Pulse Dosed with either PPF1 or saline control. Shaded areas indicating a dark cycle, and boxed region when a hot plate test was administered.

FIG. 20 reports the number of wheel revolutions during given time periods, with shaded areas indicating a dark cycle. An unpaired t-test was used to assess statistical significance of total running for both treated and untreated groups in the light and dark cycles. Rhythmic expression profiles were extracted and characterized using time and frequency domain analysis for a 13-time point series, separately for each mouse from treated and untreated groups with five 13-time point series per mice. Period, phase and amplitude were the parameters defined for each rhythm and were compared between the two groups using unpaired two-sided t-test. Mice treated with PPF1 ran significantly more than untreated animals, an indicator of improved motor activity. Mice were subjected to a hot plate test to control for normal pain sensation in their paws. Loss of sensation could have affected prior behavioral readouts. Hot plate testing led to a slight increase in activity after returning to the running wheel cage environment as evident by the spike in wheel revolutions indicated in the boxed segment of FIG. 20.

h. Example 8

Recombinant human albumin ("rhAlbumin," Albumedix, Ltd, Nottingham, UK), clarified young human plasma ("YP"), or saline control were administered to 10.5-month-old immunocompromised mice (NOD.Cg-Prkdscid Il2rgtm 1 Wj1/SzJ, "NSG" strain). All animals received 50 mg/kg of BrdU IP in week 1 prior to 7-day pulse dosing. rhAlbumin and YP were diluted to 50 mg/mL in water for injections (WFI, 0.9% saline). All mice received IV injections of 150 µL of rhAlbumin, YP, or saline per dose for 7 consecutive days. Mice were sacrificed 6 weeks after the last day of treatment.

Figure 21A:
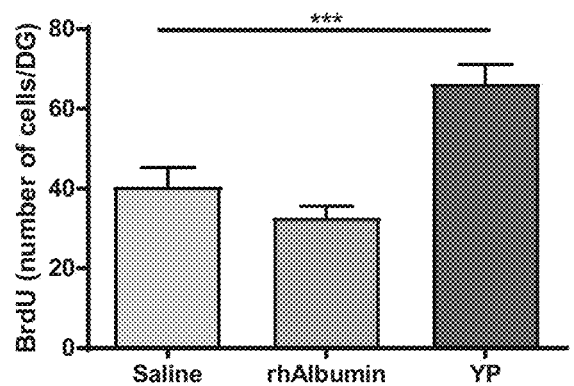
FIG. 21A shows the number of BrdU labeled cells within the granule layer of the dentate gyrus in three treatment groups of 10.5-month-old NSG mice, treated with young plasma, recombinant human albumin ("rhAlbumin"), and saline control.

FIG. 21A shows the amount of cell survival in all 3 treatment groups as determined by the number BrdU-labeled cells in the dentate gyrus ("DG"). Young plasma significantly increased cell survival compared to saline and rhAlbumin, whereas rhAlbumin had no significant effect on cell survival. All data shown are mean±s.e.m. (*** P<0.001 by unpaired t-test).

Figure 21B:
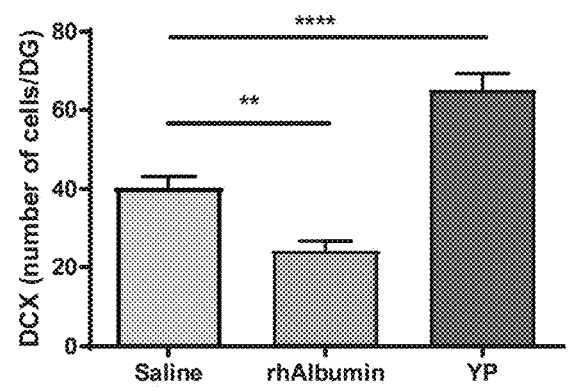
FIG. 21B shows the number of DCX labeled cells in the granule layer of the dentate gyrus for three treatment groups of 10.5-month-old NSG mice, treated with young plasma, recombinant human albumin ("rhAlbumin"), and saline control.

FIG. 21B shows the amount of DCX staining in all 3 treatment groups as determined by the number of DCX positive cells in the dentate gyrus ("DG"). Young plasma significantly increased neurogenesis compared to saline and rhAlbumin, whereas rhAlbumin was associated with a decrease in neurogenesis as compared to saline control. All data shown are mean±s.e.m. ( P<0.01; * P<0.001 by unpaired t-test).

i. Example 9

Dissociated mixed neuronal cells derived from mouse E16 cortex were plated and grown on a 48-well multielectrode array plate (Axion Biosystems). Each well contain 16 electrodes which are in physical contact with the plated neuronal cells and measure subtle changes in the cellular membrane properties. This setup allows assessing a variety of different parameters to get information about neuronal spiking activity and firing behavior at single electrode level, as well as information about the extent of neuronal connectivity by assessing synchrony of the neuronal firing properties across multiple electrodes within a well.

The neuronal cultures were maintained in the presence of the treatment conditions from day 1 onwards. Treatment conditions comprised Neurobasal medium plus B27 supplements containing 10% (v/v): recombinant human Albumin (("rhAlbumin," Albumedix, Ltd, Nottingham, UK); PPF1; or HAS1. PBS constituted the control. Neuronal activity was measured at day 7 and day 14 in culture.

Figure 22:
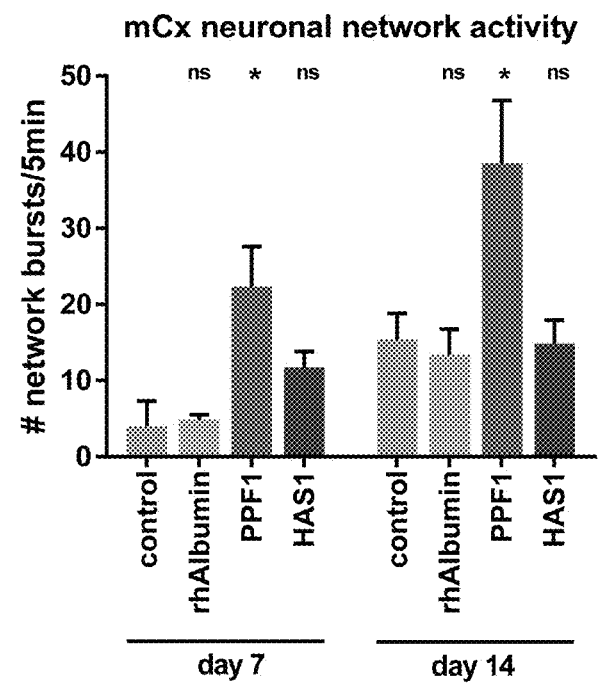
FIG. 22 reports the degree of increase in neuronal network activity in dissociated mixed neuronal cells derived from mouse E16 cortex treated with control, PPF1, HAS1, or rhAlbumin.

FIG. 22 shows that 7 days of PPF1 treatment leads to an increase in the neuronal network activity in comparison to control, rhAlbumin, or HAS1 treatment. HAS1 is a commercially-available HAS with over 95% human albumin (in relation to total protein) in a 5% solution (w/v, 50 g/L), prepared by a cold alcohol fractionation method, and derived from pooled human plasma from donors. Both PPF1 and HAS1 come in a 5% solution (w/v/, 50 g/L) and were diluted 1:10 in Neurobasal medium plus B27 supplements. The effect of PPF1 on neuronal network activity persists through to 14 days in culture. This indicates that PPF1 is associated with promotion of neuronal network maturation. Data shown as mean±s.e.m. (* P<0.05 by unpaired t-test).

j. Example 10

Figure 23:
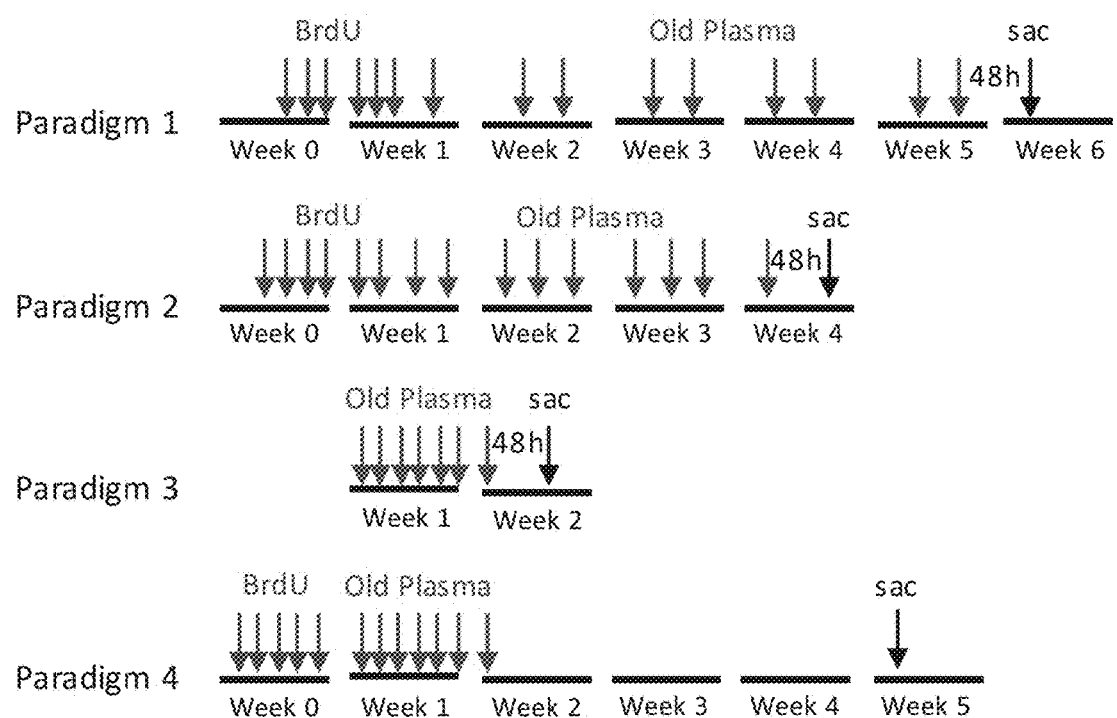
FIG. 23 depicts four paradigms of administration of clarified old human plasma (old plasma) or saline administered to 8-week-old (young) NSG mice.

Clarified old human plasma (OP) or sterile saline were administered to 8-week-old (young) immunocompromised mice (NOD.Cg-Prkdscid Il2rgtm 1 Wj1/SzJ, "NSG" strain). In each experiment mice were homogenized across treatment groups by weight. All mice were injected IP on 5 consecutive days with 150 mg/kg of BrdU in sterile PBS. BrdU injection was followed by IV administration of old plasma in different treatment paradigms at 150 μL per dose. All paradigms are outlined in FIG. 23.

Paradigm 1 involves twice weekly injections for a total of 10 injections over 5 weeks. Histological analysis was performed 48 hours after the last plasma dose. Paradigm 2 involves thrice weekly injections for a total of 10 injections over 4 weeks, with histological analysis 48 hours after the last dose. In Paradigm 3 mice were injected daily for 7 consecutive days and analyzed histologically 48 hours after the last dose. In Paradigm 4, mice were injected daily for 7 consecutive days and analyzed 21 days after the last dose. The brains of old plasma treated mice were analyzed for a marker of endothelial inflammation, VCAM-1 in hippocampus, and for the number of newborn neurons as marked by doublecortin (DCX) positive cells in the dentate gyrus. VCAM-1 was imaged on a Hamamatsu NanoZoomer HT (Hamamatsu) after immunohistochemistry on 30 μm free floating sections and analyzed using Image Pro Software (Media Cybernetics). DCX positive cells in the dentate gyrus were counted live on a Leica wide field microscope (Leica).

Figure 24A:
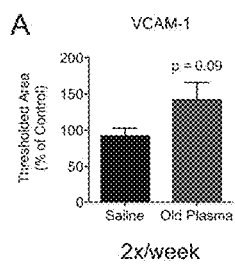
FIG. 24A depicts VCAM-1 positive labeling in the hippocampus in 8-week-old (young) NSG mice treated with twice weekly dosing of old plasma, 48 hours after the last dose was administered.
Figure 24B:
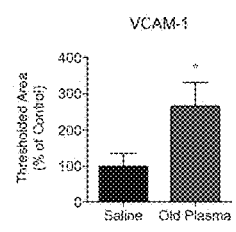
FIG. 24B depicts VCAM-1 positive labeling in the hippocampus in 8-week-old (young) NSG mice treated with thrice weekly dosing of old plasma, 48 hours after the last dose was administered.
Figure 24C:
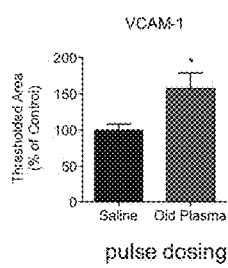
FIG. 24C depicts VCAM-1 positive labeling in the hippocampus in 8-week-old (young) NSG mice treated with Pulsed Dosing of old plasma, 48 hours after the last dose was administered.
Figure 24D:
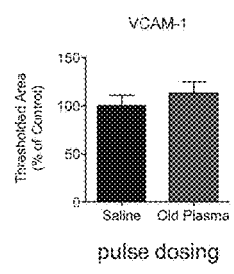
FIG. 24D depicts VCAM-1 positive labeling in the hippocampus in 8-week-old (young) NSG mice treated with Pulsed Dosing of old plasma, 21 days after the last dose was administered.

Analysis of the percent VCAM-1 positive area in the hippocampus (FIGS. 24A-24D) shows that endothelial inflammation is significantly increased 48 hours after the last plasma administration, with a trend at twice weekly dosing (FIG. 24A) and significant increases after thrice weekly (FIG. 24B) and Pulsed Dosing (FIG. 24C). VCAM-1 levels were no longer significantly enhanced 21 days after the last plasma dose was administered (FIG. 24D).

Figure 25A:
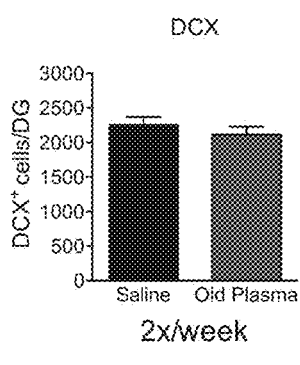
FIG. 25A depicts the number of DCX-positive cells in the dentate gyrus in 8-week-old (young) NSG mice treated with twice weekly dosing of old plasma, 48 hours after the last dose was administered.
Figure 25B:
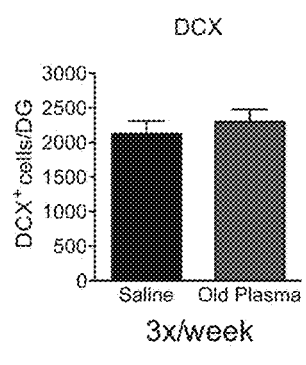
FIG. 25B depicts the number of DCX-positive cells in the dentate gyrus in 8-week-old (young) NSG mice treated with thrice weekly dosing of old plasma, 48 hours after the last dose was administered.
Figure 25C:
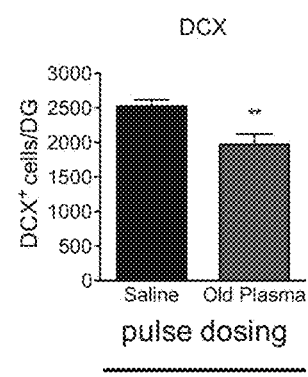
FIG. 25C depicts the number of DCX-positive cells in the dentate gyrus in 8-week-old (young) NSG mice treated with Pulsed Dosing of old plasma, 21 days after the last dose was administered.

Effects on doublecortin were only possible to observe after a 3-4 week time period, so the number of DCX positive cells were analyzed in the dentate gyrus in paradigms 1, 2 and 4. Analysis revealed that there was no effect of old plasma on neurogenesis with twice weekly (FIG. 25A) or thrice weekly (FIG. 25B) dosing paradigms, however pulsed dosing for 7 consecutive days (FIG. 25C) resulted in a significant decrease in the number of DCX positive cells. This data suggests that only pulsed dosing of old human plasma had significant effects on neurogenesis.

k. Example 11

Figure 26:
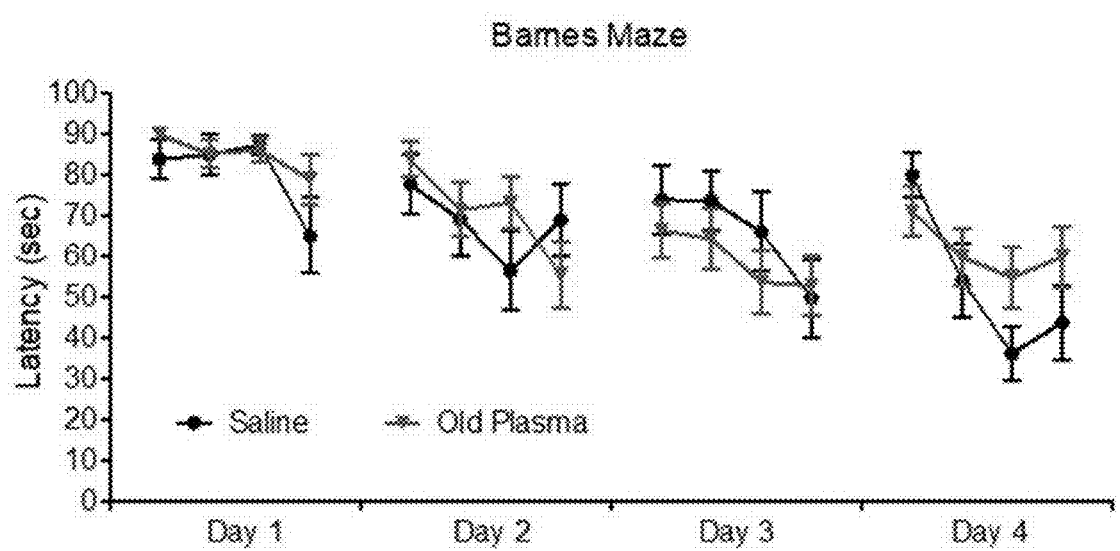
FIG. 26 shows the Barnes Maze escape latency time course and reports the time to reach and enter the escape hole for old plasma and saline-treated 8-week-old (young) NSG mice. The mice were treated for 7 consecutive days with old human plasma or saline and tested 4 weeks after the last injection.

Eight-week-old NSG mice treated for 7 consecutive days with old human plasma (65-68-year-old origin) were tested using the Modified Barnes Maze 4 weeks after the last injection old plasma. FIG. 26 shows the Barnes Maze escape latency time course and reports the time to reach and enter the escape hole for old plasma and saline-treated NSG mice. There were no significant differences in escape latency between groups, but on day 4 old plasma treated mice performed less well than the saline controls. This data indicates reduced learning and memory in a spatial memory task associated with hippocampal function. All data shown are mean±s.e.m. Two-way ANOVA, Sidak post-hoc test).

Figure 27:
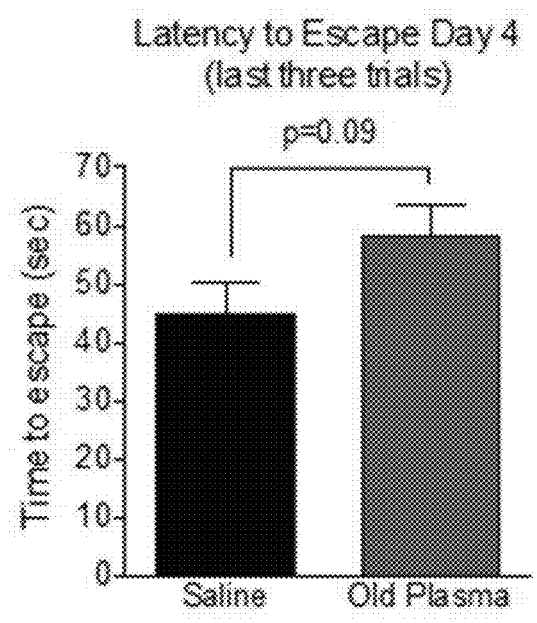
FIG. 27 depicts the average escape latency in the last three Barnes Maze trials on day 4 of testing of 8-week-old (young) NSG mice who were treated for 7 consecutive days with old human plasma or saline. Testing occurred 4 weeks after the last injection.

FIG. 27 depicts the average escape latency in the last three Barnes Maze trials on day 4. Old plasma treated mice showed a trend towards higher escape latency indicative of impaired memory function. All data shown are mean±s.e.m. (unpaired t-test).

Figure 28:
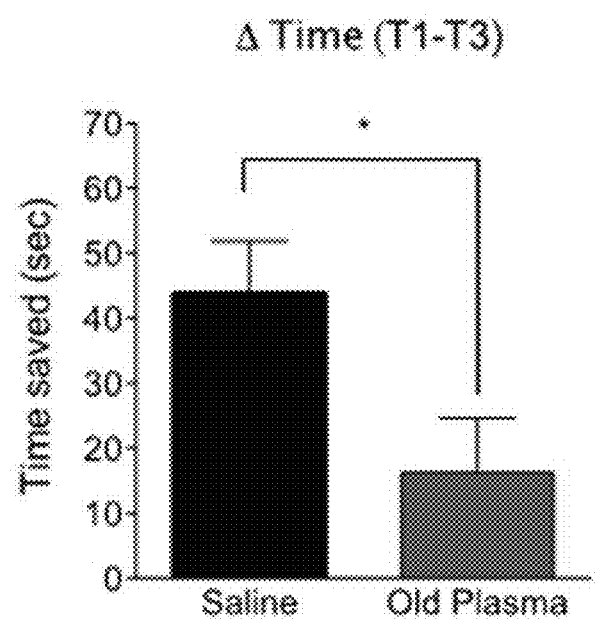
FIG. 28 depicts the difference in escape latency between Barnes Maze trials 1 and 3 in 8-week-old (young) NSG mice who were treated for 7 consecutive days with old human plasma or saline. Testing occurred 4 weeks after the last injection.

FIG. 28 depicts the difference in escape latency between Barnes Maze trials 1 and 3 and shows that these trials can be used as a measure of learning within a single day. Old plasma treated mice have a significantly lower difference in escape latency between these trials revealing decreased learning ability. All data shown are mean±s.e.m. (* P<0.05 by unpaired t-test).

Figure 29:
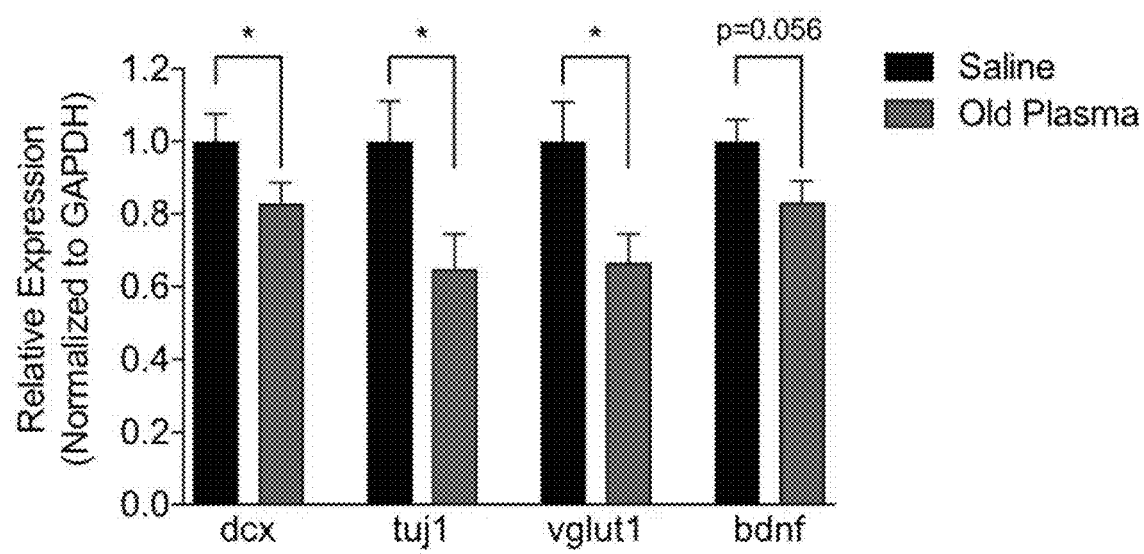
FIG. 29 reports the results of quantitative polymerase chain reaction (qPCR), quantifying mRNA levels of DCX, vesicular glutamate receptor (vglut1), synapsin 1 (syn1), beta III tubulin (tuj1), and brain-derived neurotrophic factor (bdnf) in 8-week-old (young) NSG mice who were treated for 7 consecutive days with old human plasma or saline.

FIG. 29 reports the results of qPCR which was used to quantify mRNA levels of different markers associated with neurogenesis and synaptic function. Relative expression levels of doublecortin (DCX), a marker for newborn neurons, was decreased in agreement with histological analysis of the same marker. In addition, there were trends towards decreased levels of vglut1 (vesicular glutamate transporter 1), a marker of glutamatergic synapses, synaptic marker syn1 (synapsin 1), tuj1 (beta III tubulin), and bdnf (brain-derived neurotrophic factor). These decreases indicate an overall impaired synaptic and neuronal network in the brains of old plasma-injected mice. All data shown are mean±s.e.m. (* P<0.05 by unpaired t-test).

l. Example 12

Figure 30:
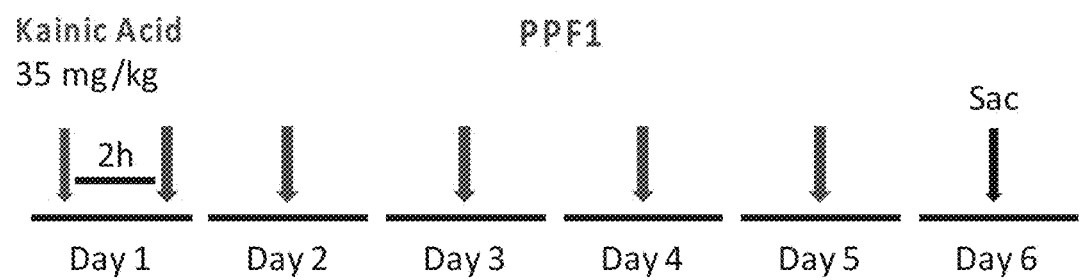
FIG. 30 depicts the dosing paradigm for 8-week-old (young) NSG mice treated with 35 mg/kg of Kainic acid or saline, and subsequently treated with either PPF1 or saline daily for 5 consecutive days.

Young (8-week-old) immunocompromised mice (NOD.Cg-Prkdscid Il2rgtm 1 Wj1/SzJ, "NSG" strain) were homogenized across treatment groups by weight. Animals were injected subcutaneously (s.c) with 35 mg/kg of Kainic acid (Sigma) in sterile saline or saline control. Peripheral Kainic acid administration resulted in acute seizure activity, inflammation in the hippocampus and in a subset of mice also in neuronal loss in the CA1 region of the hippocampus. Two hours after Kainic acid injection, mice were intravenously dosed with 150 µl of PPF1 or saline. Administration of PPF1 or saline was continued daily for a total of 5 days (FIG. 30). Tissue was collected for analysis on day 6. Inflammatory changes in the CA1 region of the hippocampus were analyzed after immunofluorescent staining for microglial activation (CD68) and astrocyte activation (GFAP). Sections were imaged on a Hamamatsu NanoZoomer HT (Hamamatsu) after immunohistochemistry on 30 µm free floating sections and analyzed using Image Pro Software (Media Cybernetics).

Figure 31A:
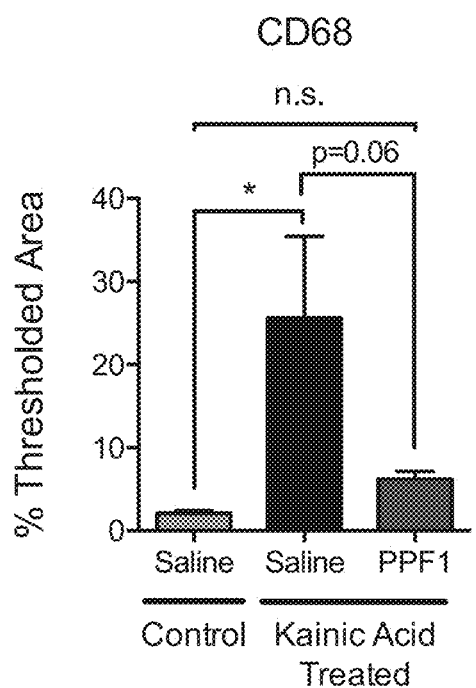
FIG. 31A reports the percent of CD68 positive area in the CA1 region of the hippocampus of mice treated as per the paradigm depicted in FIG. 28.
Figure 31B:
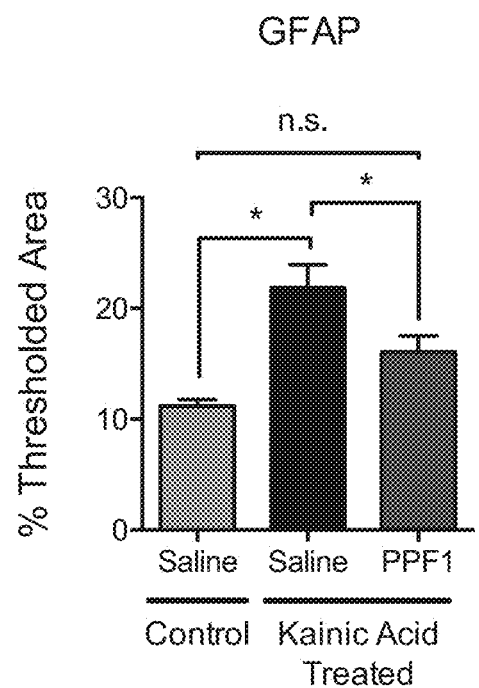
FIG. 31B reports the percent GFAP positive area in the CA1 region of the hippocampus of mice treated as per the paradigm depicted in FIG. 28.

Analysis of the percent CD68 positive area in the CA1 region of the hippocampus shows that Kainic acid administration results in increased CD68 immunoreactivity suggesting increased microglial activation (FIG. 31A). Five days of PPF1 administration results in a significant decrease of the percentage of CD68 positive area and therefore a reduction in microglial activation. Similarly, analysis of the percentage of GFAP positive area (FIG. 31B) shows a significant increase after Kainic acid administration, which is significantly reduced after PPF1 dosing. The data suggests that PPF1 has an acute anti-inflammatory effect in the brains of mice that have been dosed with Kainic acid. * P<0.05 One-Way ANOVA with Dunnett's multiple comparison Post-Hoc analysis.

m. Example 13

NSG mice at 6 months of age were injected daily for one week (7 days), IV, with either PPF1 or saline control at a dose of 150 µL (10 mg/mL). All mice were treated with BrdU 50 mg/kg of BrdU IP once per day on the same days they received PPF1 or saline control. The mice were then divided into two cohorts. The first cohort was sacrificed one day immediately after the 7 days of concurrent treatment with BrdU and PPF1. The second cohort was sacrificed 7 days later, and received an additional 7 days of daily BrdU administration.

Figure 32:
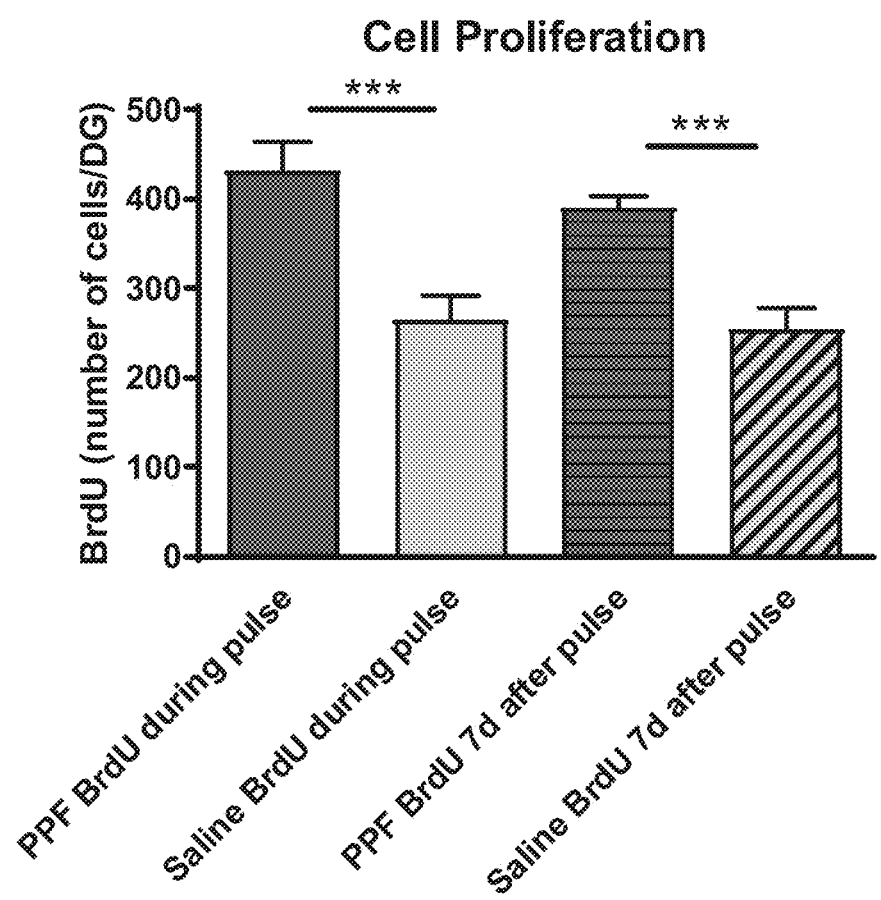
FIG. 32 reports the number of cells stained for BrdU in the dentate gyrus in 6-month-old NSG mice pulse dosed with PPF1 or saline control for 7 consecutive days with concurrent administration of BrdU. The first two columns constitute a cohort analyzed 7 days after the last treatment of PPF1/saline control and BrdU; the second two columns constitute a cohort analyzed 14 days after the last treatment of PPF1/saline control and BrdU.

FIG. 32 shows the number of cells stained in the dentate gyrus of cohorts 1 and 2 (left to right). Both cohorts exhibited increased cell proliferation in the dentate gyrus compared to saline control. (*** p<0.001 unpaired t-test).

n. Example 14

Figure 33:
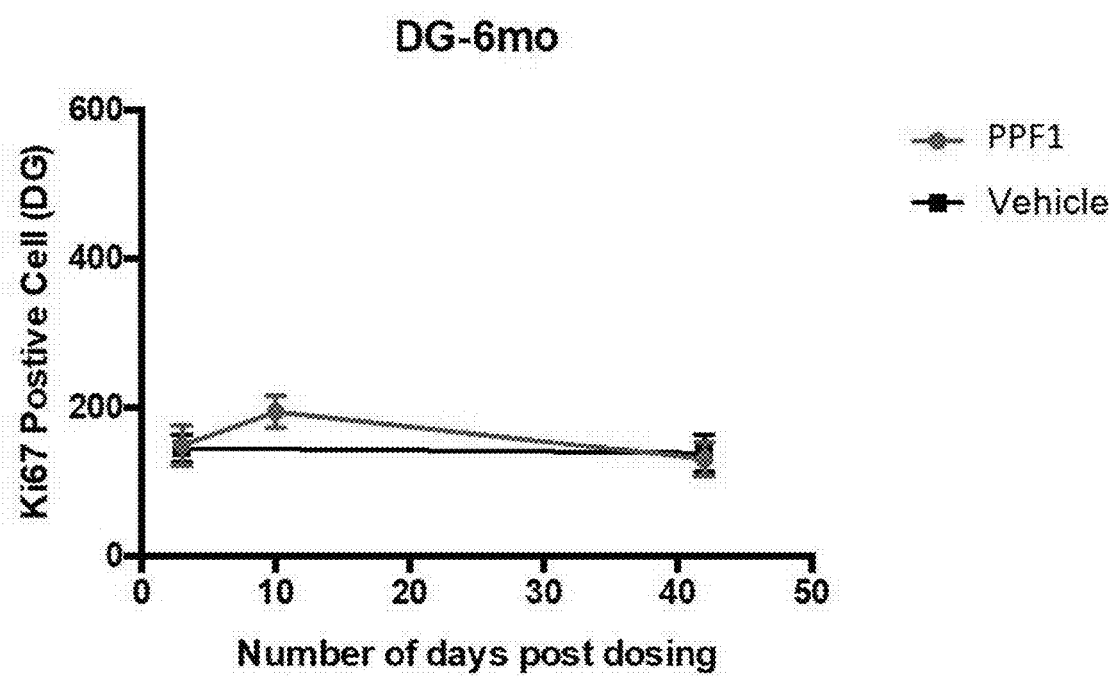
FIG. 33 depicts the increase in proliferating cells (Ki67+) in the dentate gyrus of 6-month-old NSG mice 10 days after completion of a Pulse Dose regimen with PPF1.
Figure 34:
FIG. 34 shows sections of the dentate gyrus and subventricular zone of 6-month-old NSG mice 10 days after completion of a Pulse Dose regimen with PPF1.

NSG mice at either 3 or 6 months of age were injected daily for one week (7 days), IV, with either PPF1 or saline vehicle. Mice were subsequently sacrificed 3, 10, or 42 days after the 7 daily doses were administered. Brains were stained with Ki67, a nuclear marker only present in proliferating cells which marks neural stem and progenitor cells in the blade of the dentate gyrus. FIG. 33 shows that 6-month-old mice exhibited an increase in total progenitor cells (Ki67 positive or "Ki67+") in the dentate gyrus at 10 days following the termination of the 7-consecutive day pulse dosing regimen using PPF1. FIG. 34 shows the staining (bright areas) of Ki67 in the dentate gyrus at 10 days in NSG mice following the termination of the 7-consecutive day pulse dosing regimen using PPF1. This shows that one possible mechanism of action for PPF1 in increasing total cell survival and neurogenesis at 42 days following cessation of dosing could be due to an increase in total progenitor cells (neural stem cells).

o. Example 15

Commercially-available PPF ("PPF1") or saline control was administered to two different populations of 6 and 12-month-old immunocompromised mice (NOD.Cg-Prkdscid Il2rgtm 1 Wj1/SzJ, "NSG" strain). All animals received 50 mg/kg of BrdU in week 1 prior to 7-day pulse dosing of test agent. All mice received IV injections of 150 µL of PPF1 or saline per dose for 7 consecutive days. One cohort from each treatment group was used to investigate proliferation and was sacrificed 6 weeks after the last administered dose.

Figure 35A:
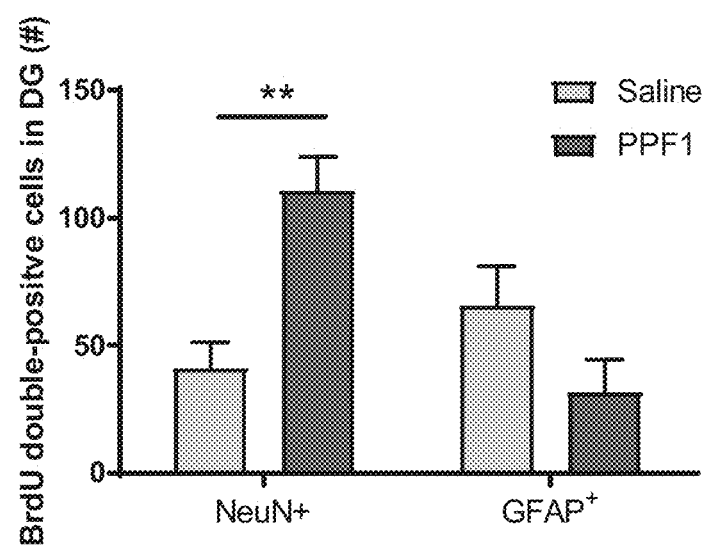
FIG. 35A reports the cell fate of cells in the dentate gyrus in 6-month-old NSG mice treated with either PPF1 or saline control with a 7-day Pulse Dosing regimen, where BrdU was administered for 5 consecutive days immediately prior to the commencement of the Pulse Dosing regimen. The degree of NeuN+co-localization staining with BrdU indicates the degree to which neuroprogenitor cells became neurons. The degree of GFAP+co-localization staining with BrdU indicates the degree to which neuroprogenitor cells became astrocytes.

FIG. 35A reports that the cohort of 6-month-old mice treated with PPF1 exhibited a significant increase in the number of progenitor cells differentiated into neurons (NeuN+) compared to saline control, and a reduction in the number of progenitor cells differentiated into astrocytes (GFAP+) compared to control. All data shown are mean±s.e.m. (** P<0.01 by unpaired t-test).

Figure 35B:
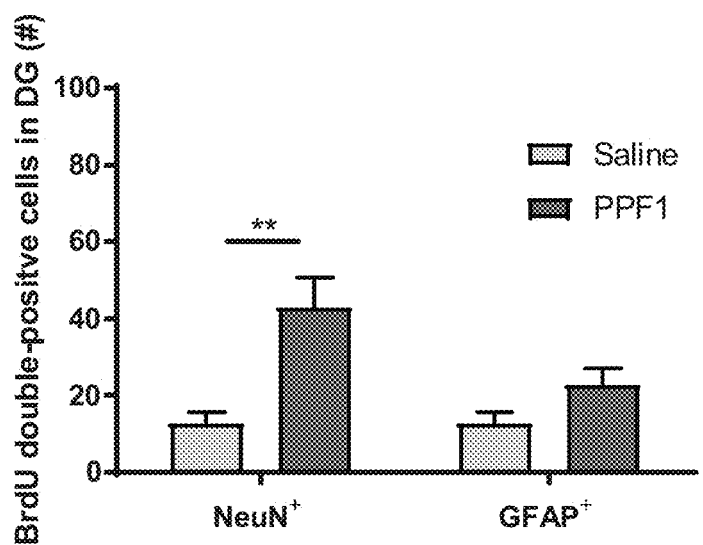
FIG. 35B reports results from a similar experiment as FIG. 35A, but in 12-month-old NSG mice.

FIG. 35B reports that the cohort of 12-month-old mice treated with PPF1 exhibited a significant increase in the number of progenitor cells differentiated into neurons (NeuN+) compared to saline control, and a statistically-insignificant difference in the number progenitor cells differentiated into of astrocytes compared to control. All data shown are mean±s.e.m. (** P<0.01 by unpaired t-test).

p. Example 16

Clarified old human plasma (old plasma) or sterile saline were administered to 3-month-old mice (NOD.Cg-Prkdscid Il2rgtm 1 Wj1/SzJ, "NSG" strain). In each experiment mice were homogenized across treatment groups by weight. All mice were injected IP on 5 consecutive days with 150 mg/kg of BrdU in sterile saline. BrdU injection was followed by IV administration of old plasma or sterile saline at 150 µL per dose daily for 7 consecutive days and analyzed histologically 4 weeks after the last dose.

Figure 36A:
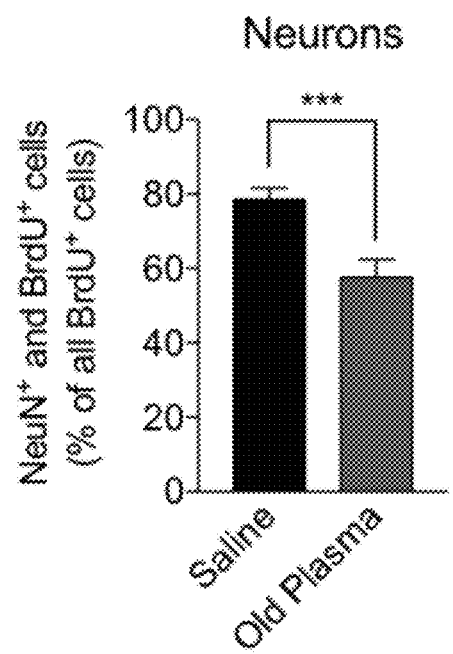
FIG. 36A reports the cell fate of cells in the dentate gyrus in 3-month-old NSG mice treated with either old plasma or saline control with a 7-day Pulse Dosing regimen, where BrdU was administered for 5 consecutive days immediately prior to the commencement of the Pulse Dosing regimen. The degree of NeuN+co-localization staining with BrdU indicates the degree to which neuroprogenitor cells became neurons.
Figure 36B:
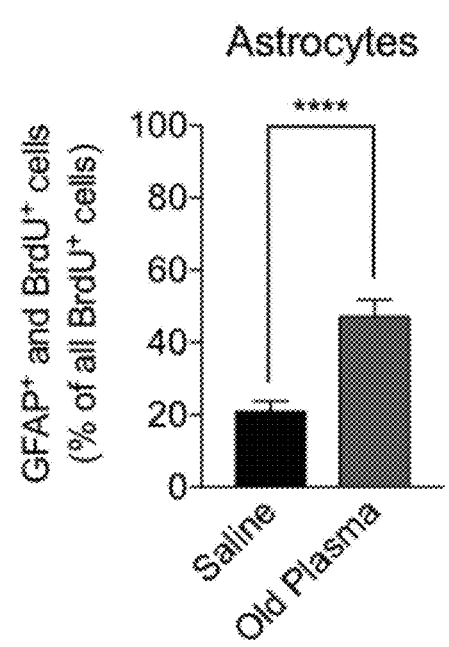
FIG. 36B reports results from the experiment detailed in FIG. 36A, but reports the degree of GFAP+co-localization staining with BrdU, indicating the degree to which neuroprogenitor cells became astrocytes FIGS. 37A-37C report the number of cFos-positive cells in the (FIG. 37A) whole brain, (FIG. 37B) cortex, and (FIG. 37C) isocortex of 18-month-old mice treated with a 7-day Pulse Dosing regimen of PPF1 or saline.

FIGS. 36A and 36B depict the cell fate of BrdU-labeled proliferating neural progenitor cells 4 weeks after the last dose. In mice injected with old plasma, surviving BrdU-labeled cells differentiate significantly less into neurons than into astrocytes. This indicates that old human plasma changes the cell fate of neural progenitor cells in young mice towards the astrocyte lineage (FIG. 36B) and negatively impacts the number of newborn neurons in the dentate gyrus (FIG. 36A) (n=12 per group). All data shown are mean±s.e.m. (* P<0.001; ** P<0.0001 by unpaired t-test).

q. Example 17

Cortical Activation.

Aged (18 months old) C57BL/6 mice received daily IV injections of 150 ul PPF1 or 0.9% sterile saline for 7 days. Two and a half (2.5) hours after the last test agent administration, mice were sacrificed by transcardial perfusion with 0.9% saline followed by 4% formaldehyde under deep anesthesia with ketamine and xylazine. The brains were dissected, post-fixed and then processed with the iDisco procedure to visualize cFos positive cells via Light Sheet Fluorescence Microcopy (LSFM) at 2×2×3 micrometer voxel resolution. The imaged brains were aligned as 3D volumes and activated cFos positive cells were computationally detected. The statistical comparison between groups was performed by negative binomial regression corrected for multiple comparisons by false discovery rate. (* indicates a q-value of less than 0.05).

Figure 37A:
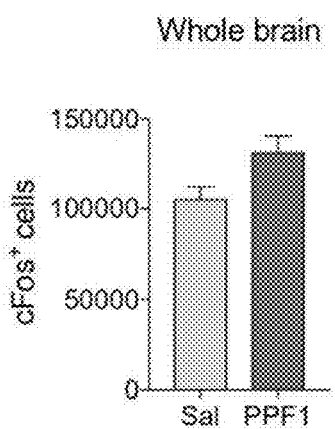
Figure 37B:
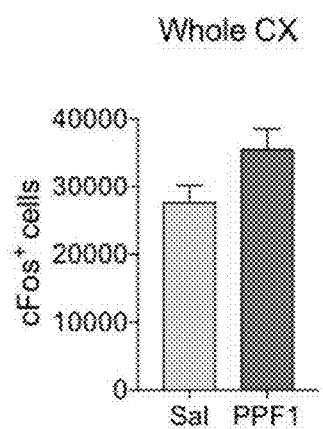
Figure 37C:
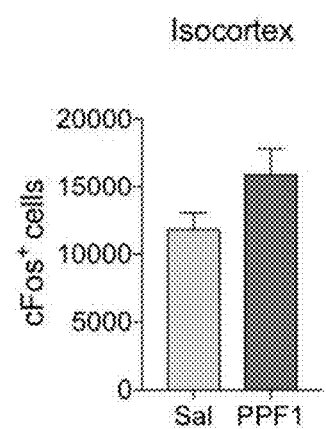
Figure 38A:
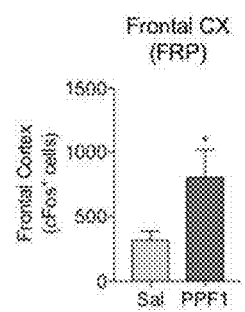
FIGS. 38A-38D report the number of cFos-positive cells in the (FIG. 38A) frontal cortex, (FIG. 38B) orbital cortex, (FIG. 38C) infralimbic cortex, and (FIG. 38D) prelimbic cortex of 18-month-old mice treated with a 7-day Pulse Dosing regimen of PPF1 or saline.
Figure 38B:
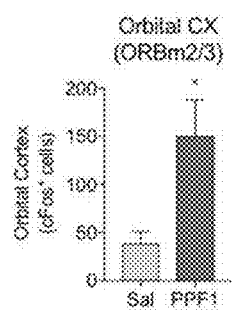
Figure 38C:
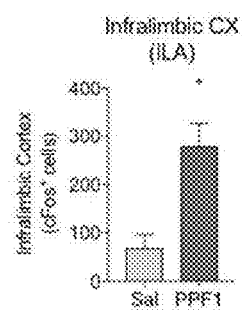
Figure 38D:
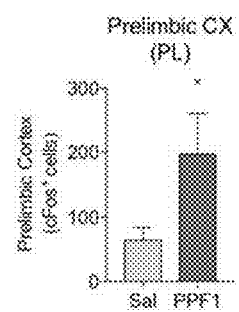
Figure 39A:
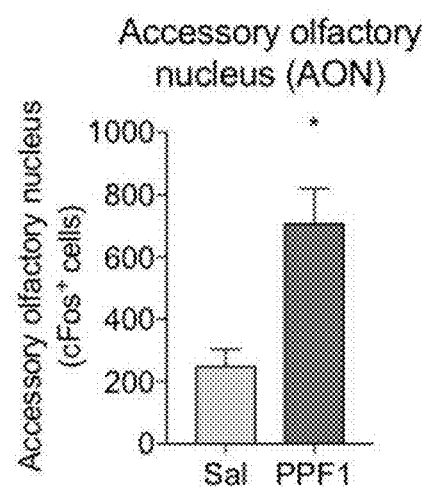
FIGS. 39A and 39B report the number of cFos-positive cells in the (FIG. 39A) accessory olfactory nucleus and the (FIG. 39B) olfactory tubercle of 18-month-old mice treated with a 7-day Pulse Dosing regimen of PPF1 or saline.
Figure 39B:
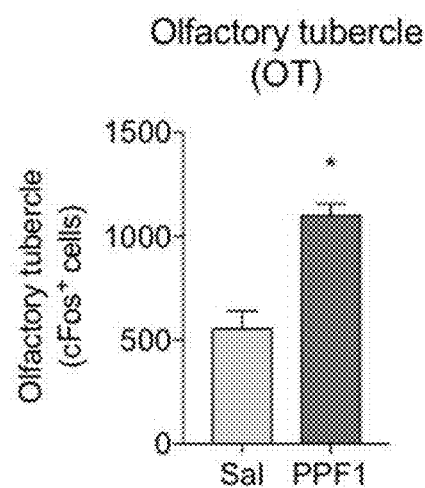
Figure 40:
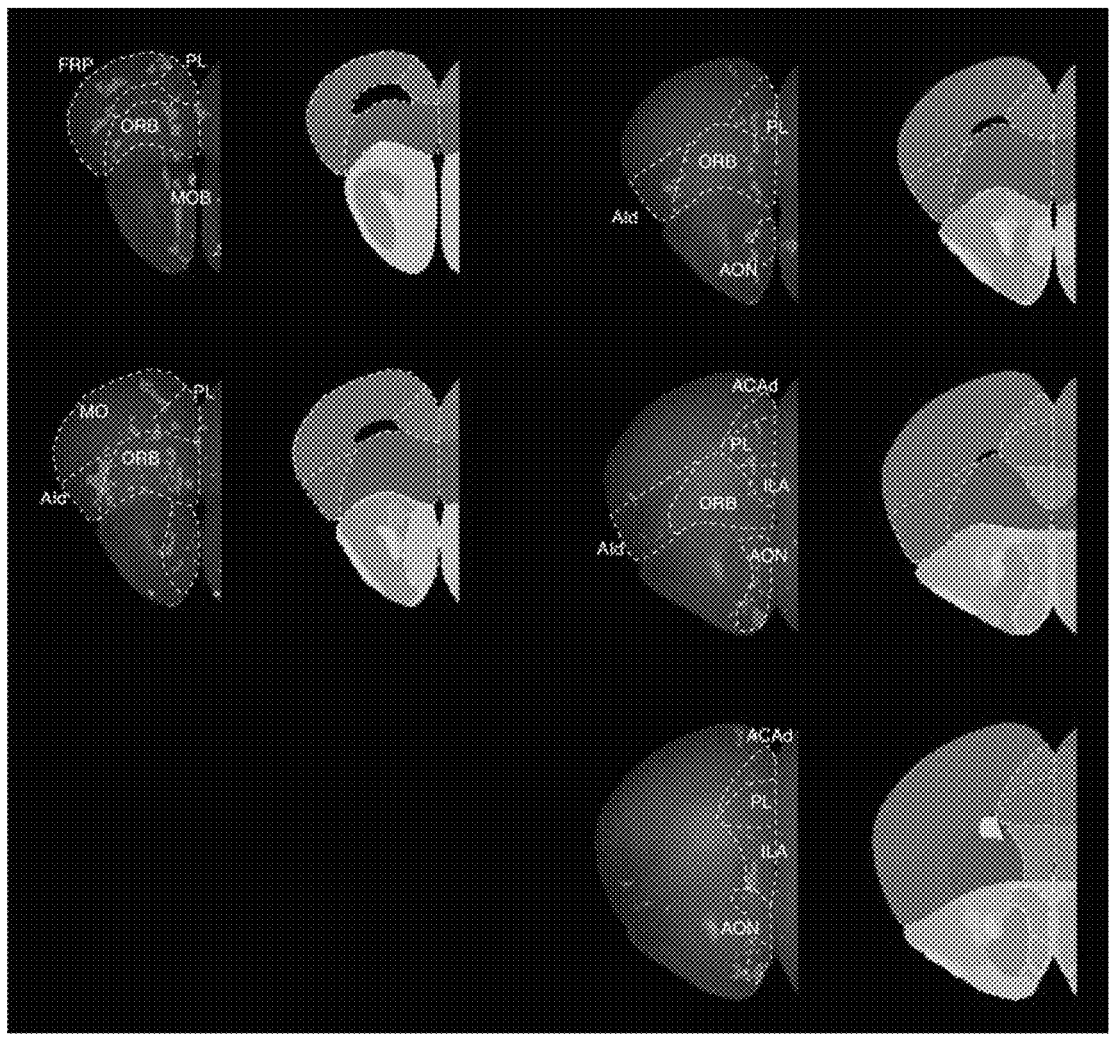
FIG. 40 depicts a Voxel statistics-based visualization of local cortical activation in the frontal cortex (FRP), the orbital cortex (ORB), the infralimbic cortex (ILA), the prelimbic cortex (PL), and the accessory olfactory nucleus (AON) of 18-month-old mice treated with a 7-day Pulse Dosing regimen of PPF1 or saline.

Analysis of the mouse brains showed an overall increase in the number of cFos positive cells in the whole brain volume as well as in cortex and isocortex in PPF1 treated 18-month-old mice (FIGS. 37A-37C). Using the binomial regression corrected for multiple comparison the differences these increases in overall positive cFos numbers did not reach significance. However, analysis of more defined cortical areas, such as the frontal, orbital, infralimbic and prelimbic cortex showed a significant elevation in the number of cFos positive cells (FIGS. 38A-38D) indicative of increased neuronal activity. Enhanced activity in the prefrontal cortex area is correlated with enhanced cognitive performance, suggesting that PPF1 treatment results in cognitive improvements in aged C57BL/6 mice. Similar significant increases in cFos positive cell numbers were also found in the accessory olfactory nucleus and the olfactory tubercle (FIGS. 39A-39B). These areas are associated with processing of olfactory information and the enhancement in activity suggests increased olfactory function. Voxel statistics-based visualization of the cFos activation in red showed the increase of cFos signal in the cortex of mice treated with PPF1 (FIG. 40).

r. Example 18

Commercially-available PPF ("PPF1") or saline control was administered to 22-month-old wild type (WT) mice (C57BL/6J, "WT", Strain Code 0664, Jackson Labs, Bar Harbor, Me.). All animals received 50 mg/kg of BrdU in week 1 prior to 7-day pulse dosing. Subsequently, all mice received IV injections of 150 µL of PPF1 or saline per dose for seven consecutive days. Mice were sacrificed 10 days after the last PPF1 or saline injection and the brains were processed for histology.

Figure 41A:
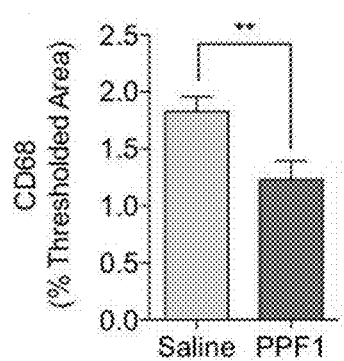
FIG. 41A reports the percent CD68 immunoreactive area in the hippocampus in 22-month-old C57BL/6J wild type mice treated with a 7-day Pulse Dosing regimen with PPF1 or saline control.
Figure 41B:
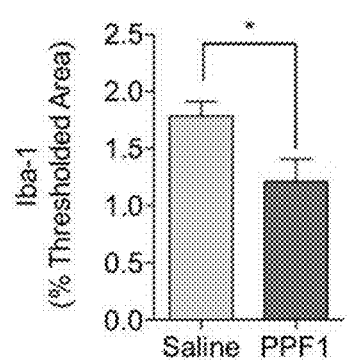
FIG. 41B reports the percent Iba-1 immunoreactive area in the hippocampus in 22-month-old C57BL/6J wild type mice treated with a 7-day Pulse Dosing regimen with PPF1 or saline control.
Figure 41C:
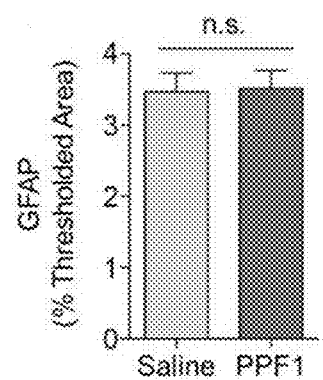
FIG. 41C reports the percent GFAP immunoreactive area in the hippocampus in 22-month-old C57BL/6J wild type mice treated with a 7-day Pulse Dosing regimen with PPF1 or saline control.

FIG. 41A reports the percent CD68 immunoreactive area in the hippocampus (n=10, 10). FIG. 41B reports the percent Iba-1 immunoreactive area in the hippocampus (n=10, 10). FIG. 41C reports the percent GFAP immunoreactive area in the hippocampus (n=10, 10). All data shown are mean±s.e.m. (* P<0.05; ** P<0.01 by unpaired t-test). These results show a significant decrease in the microglial markers, CD68 and Iba-1 in the hippocampus of PPF1-treated old mice.

s. Example 19

Commercially-available PPF ("PPF1") or saline control was administered to 23-month-old wild type (C57BL/6J, "WT", Strain Code 0664, Jackson Labs, Bar Harbor, Me.). All animals received 50 mg/kg of BrdU in week 1 prior to seven consecutive day pulse dosing. Subsequently, all mice received IV injections of 150 µL of PPF1 or saline per dose for seven consecutive days. One cohort from each treatment group was used to investigate histological markers for neuroinflammation and was sacrificed 6 weeks after the last administered dose.

Figure 42A:
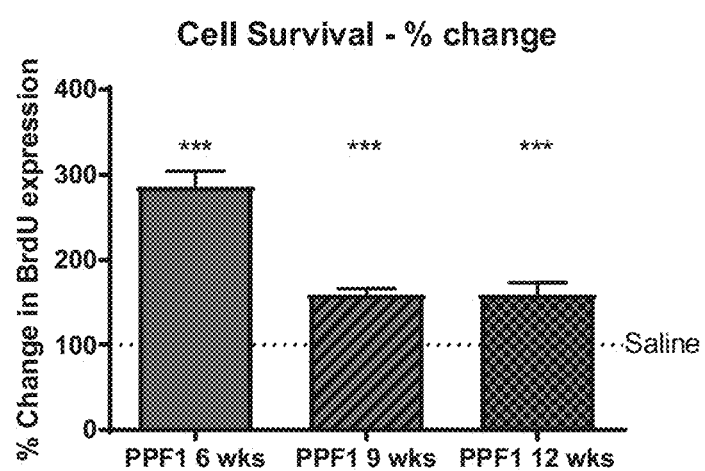
FIG. 42A reports the percent change in BrdU staining in PPF1-treated 23-month-old wild type C57BL/6J mice compared to saline control 6, 9, and 12 weeks post-dosing using a seven-consecutive day Pulsed Dosing regimen.

FIG. 42A reports the percent change in BrdU expression compared to saline control at 6, 9, and 12 weeks post-dosing, which is an indicator of cell survival in the hippocampus. Animals were treated with a 7-consecutive day Pulsed Dosing regimen.

Figure 42B:
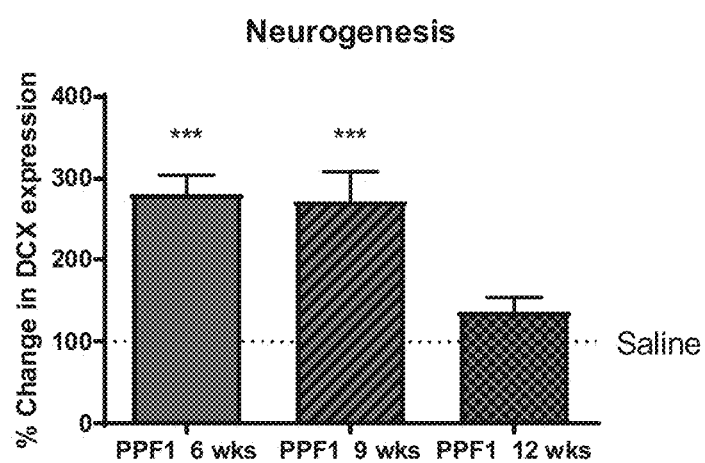
FIG. 42B reports the percent change in DCX staining in PPF1-treated 23-month-old wild type C57BL/6J mice compared to saline control 6, 9, and 12 weeks post-dosing using a seven-consecutive day Pulsed Dosing regimen.

FIG. 42B reports the percent change in doublecortin (DCX) expression compared to saline control at 6, 9, and 12 weeks post-dosing, which is an indicator of neurogenesis in the hippocampus. Animals were treated with a 7-consecutive day Pulsed Dosing regimen.

t. Example 20

Thirty (30) male alpha-synuclein transgenic mice (Line 61, wild type background C57BL/6J), aged 4 to 4.5 month-old, were divided into two groups of 15 and treated with either PPF1 or vehicle for seven (7) consecutive days. PPF1 treatment was administered IV at 5 µL per gram of body weight. Alpha-synuclein mice serve as a transgenic model for Parkinson's Disease and over-expresses the alpha-synuclein protein. This transgenic model is not immunocompromised, unlike NSG mice.

One day after the last treatment of PPF1 or vehicle, all mice were subjected to behavior and motor function testing such as nest building, pasta gnawing, wire suspension, rota-rod and beam walk. Pasta gnawing, wire suspension, and beam walk were executed a second time at the end of the study. Testing was performed in a randomized order.

Figure 43A:
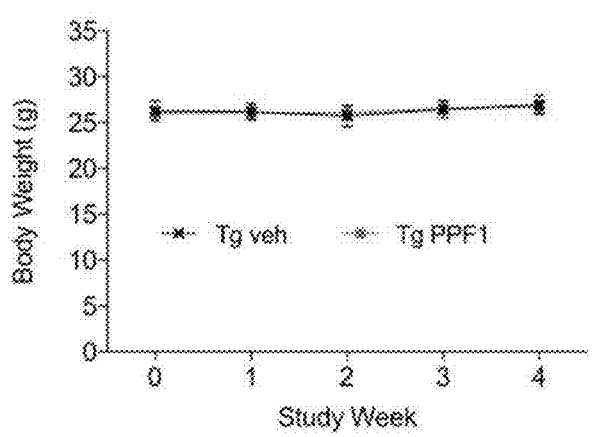
FIGS. 43A and 43B report the results of body weight measurements of 4 to 4.5-month-old male alpha-synuclein mice (Line 61) (a model for Parkinson's Disease) treated with a seven-consecutive day Pulsed Dosing regimen using PPF1 or vehicle control.
Figure 43B:
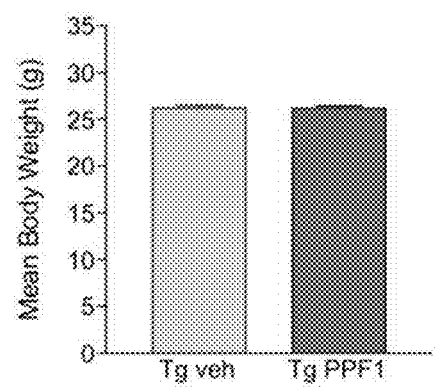

Animals were weighed once weekly. FIGS. 43A and 43B show that there were no significant differences between the PPF1 and vehicle-treated (veh) alpha-synuclein transgenic mice ("Tg").

Figure 44:
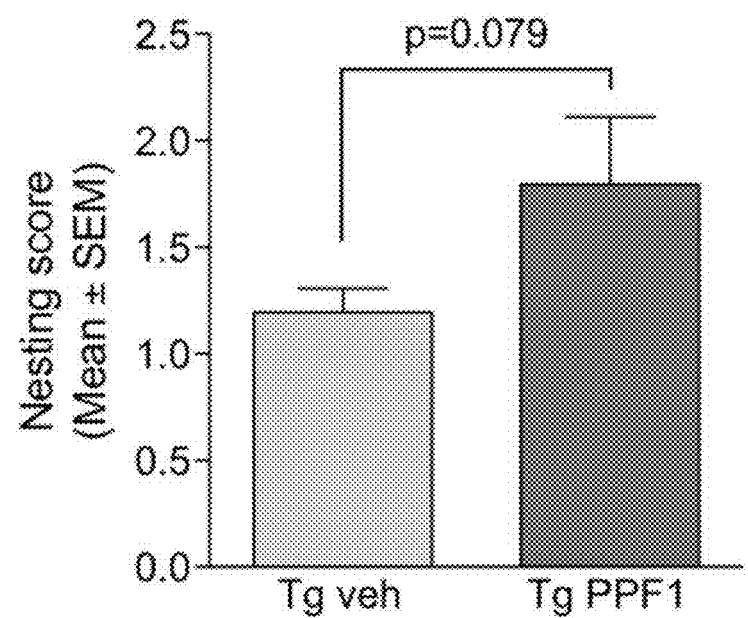
FIG. 44 reports the results of nest building in 4 to 4.5-month-old male alpha-synuclein mice (Line 61) (a model for Parkinson's Disease) treated with a seven-consecutive day Pulsed Dosing regimen using PPF1 or vehicle control.

FIG. 44 reports the results from nest building. Mice were housed individually in cages containing wood chip bedding and one square of pressed cotton ("nestlet"). No other nesting material (e.g. wood wool) was present. The nestlet was introduced on the day before the evaluation of the nest status in about 2 to 3 hours before the dark phase was initiated and the next building behavior was evaluated on the following day of the experiment within about 2 to 3 hours after the light phase started. The time span between introduction of the cotton square and evaluation of the next status was the same for all examinations. The manipulation of the nestlet and the constitution of the built nest were assessed, according to a five-point scale (Deacon, R M 2006, Assessing nest building in mice. Nat Protoc 1:1117-19.) As shown in FIG. 44, there was an increased trend in nesting behavior in PPF1-treated mice compared to vehicle-treated mice.

Figure 45A:
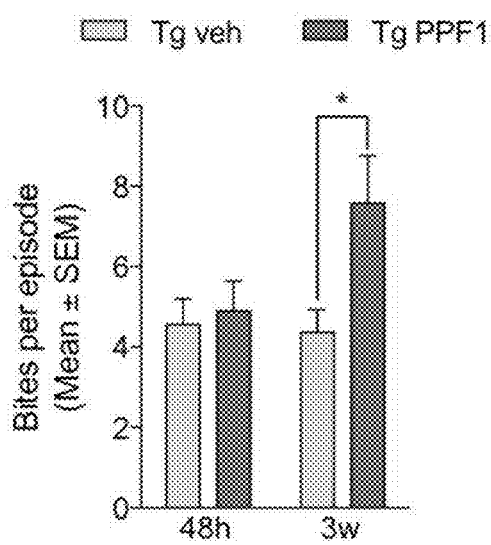
FIGS. 45A and 45B report the results of pasta gnawing and associated motor improvement, respectively, in 4 to 4.5-month-old male alpha-synuclein mice (Line 61) (a model for Parkinson's Disease) treated with a seven-consecutive day Pulsed Dosing regimen using PPF1 or vehicle control.
Figure 45B:
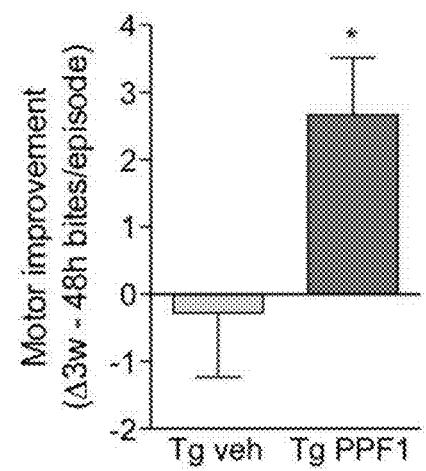

FIGS. 45A and 45B show that there was a significant increase in pasta gnawing in the PPF1-treated group compared to the vehicle-treated group 3 weeks after the last treatment, indicating motor improvement (FIG. 45B). The test was developed to study motor deficits in small rodents. Animals were brought into the experimental room at least 2 hours prior to testing. The cage top, water bottle, and food pellets were removed and a small piece of dry spaghetti (approx. 5 mm) was placed in the cage. A microphone was placed above the noodle pieces. Recording was initiated as soon as an animal started to eat. The number of bites per gnawing episode and the biting frequency were evaluated, and the gnawing pattern analyzed using Avisoft SASLab Pro software. All data shown are mean±s.e.m. (* P<0.05 by unpaired t-test).

Figure 46:
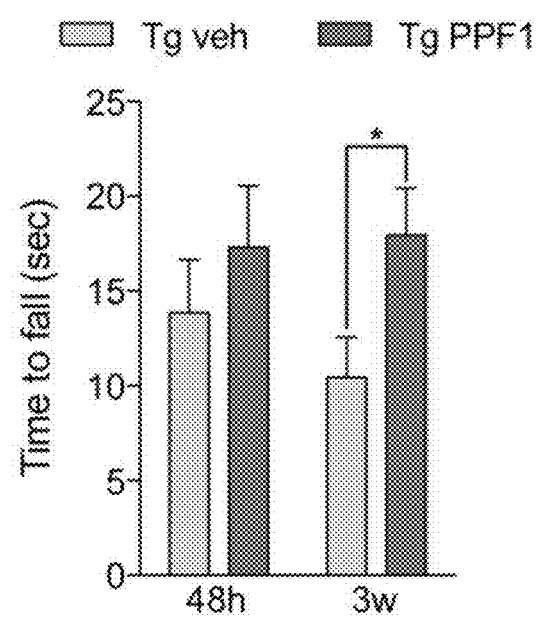
FIG. 46 reports the results of a wire suspension test in 4 to 4.5-month-old male alpha-synuclein mice (Line 61) (a model for Parkinson's Disease) treated with a seven-consecutive day Pulsed Dosing regimen using PPF1 or vehicle control.

FIG. 46 shows the results of a wire suspension test, which assesses neuromuscular abnormalities of motor strength. There was a significant increase in time to fall in the PPF1-treated group compared to the vehicle-treated group 3 weeks after the last treatment. To perform the test, the wire cage lid was used and duct tape placed around the perimeter to prevent the mouse from walking off the ledge. The animal was placed on the top of the cage lid. The lid was lightly shaken three times to force the mouse to grip the wires and then the lid turned upside down. The lid was held at a height of approximately 50-60 cm above a soft underlay, high enough to prevent the mouse from jumping down, but not high enough to cause harm in the event of a fall. The latency to fall down was quantified and a 300-second cut-off time used. Normally, a wild-type mouse can hang upside down for several minutes.

FIGS. 47A, 47B, and 47C depict the results from a beam walk test. FIG. 47A shows the different beam shapes and sizes (square or cylindrical rods) used in five different trials of increasing difficulty. FIG. 47B depicts the results of the five trials 72 hours after the last treatment. FIG. 47C depicts the results of the five trials 3 weeks after the last treatment. Mice treated with PPF1 showed significantly higher success at traversing the beam during Trial 5 of Testing 1 (72-hour post-treatment) and during Trial 4 of Testing 2 (3 weeks post-treatment). All data shown are mean±s.e.m. (** P<0.01 by binomial test).

Figure 48A:
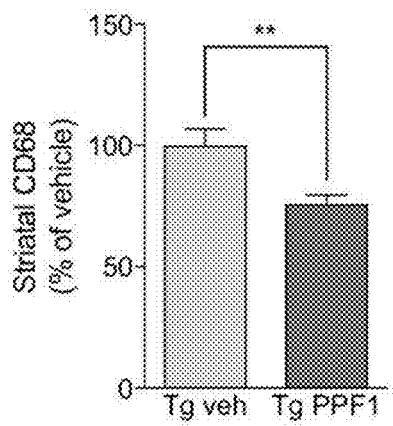
FIGS. 48A through 48F report histological results of striatal and hippocampal staining in 4 to 4.5-month-old male alpha-synuclein mice (Line 61) (a model for Parkinson's Disease) treated with a seven-consecutive day Pulsed Dosing regimen using PPF1 or vehicle control. Histological markers examined include CD68, Iba-1, and NeuN.
Figure 48B:
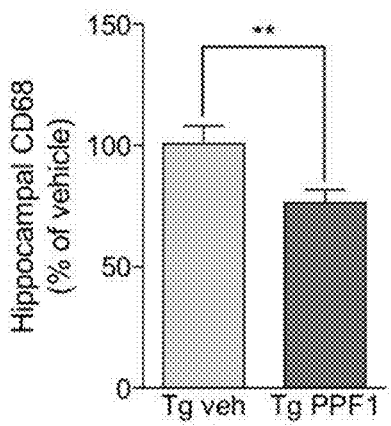
Figure 48C:
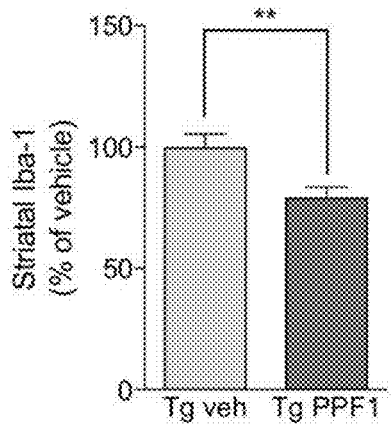
Figure 48D:
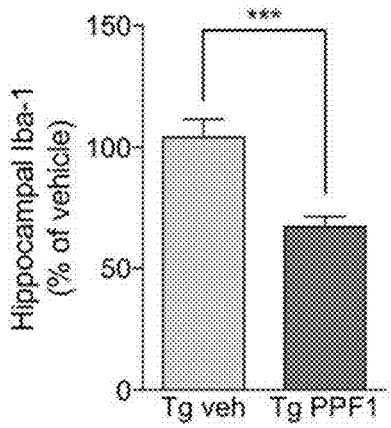

FIGS. 48A through 48F show histological results of striatal and hippocampal staining. FIG. 48A reports striatal CD68 staining. FIG. 48B reports hippocampal CD68 staining. FIG. 48C reports striatal Iba-1 staining. FIG. 48D reports hippocampal Iba-1 staining.

Figure 48E:
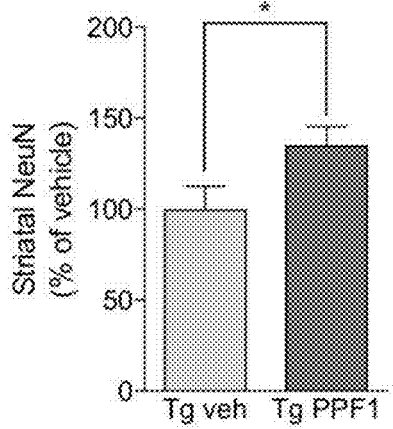
Figure 48F:
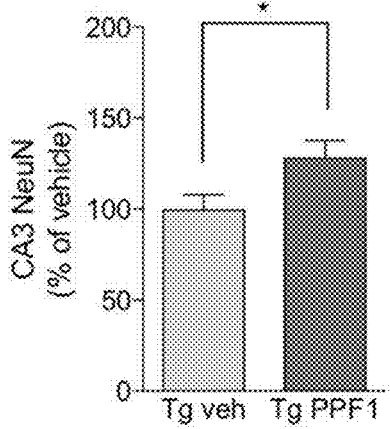

FIG. 48E reports striatal NeuN staining. FIG. 48F reports hippocampal NeuN staining. These figures show that mice treated with PPF1 demonstrated decreased microgliosis (neuroinflammation) by Iba-1 and CD68 in both the striatum and the hippocampus and increased neuronal survival by NeuN staining in the striatum and hippocampus. All data shown are mean±s.e.m. (* P<0.05,  p<0.01, * P<0.001 by unpaired t-test).

u. Example 21

PPF1, HAS1, or saline control were administered to 12-month-old mice (NOD.Cg-Prkdscid Il2rgtm 1 Wj1/SzJ, "NSG" strain). HAS1 is a commercially-available HAS with over 95% human albumin (in relation to total protein) in a 5% solution (w/v, 50 g/L), prepared by a cold alcohol fractionation method, and derived from pooled human plasma from donors. Except where noted, HAS1 was administered in the examples herein in vivo using the 5%. Mice were injected by IV administration of with PPF1, HAS1, or sterile saline at 150 µL per dose daily for 7 consecutive days and analyzed behaviorally 4 weeks after the last dose.

Figure 49:
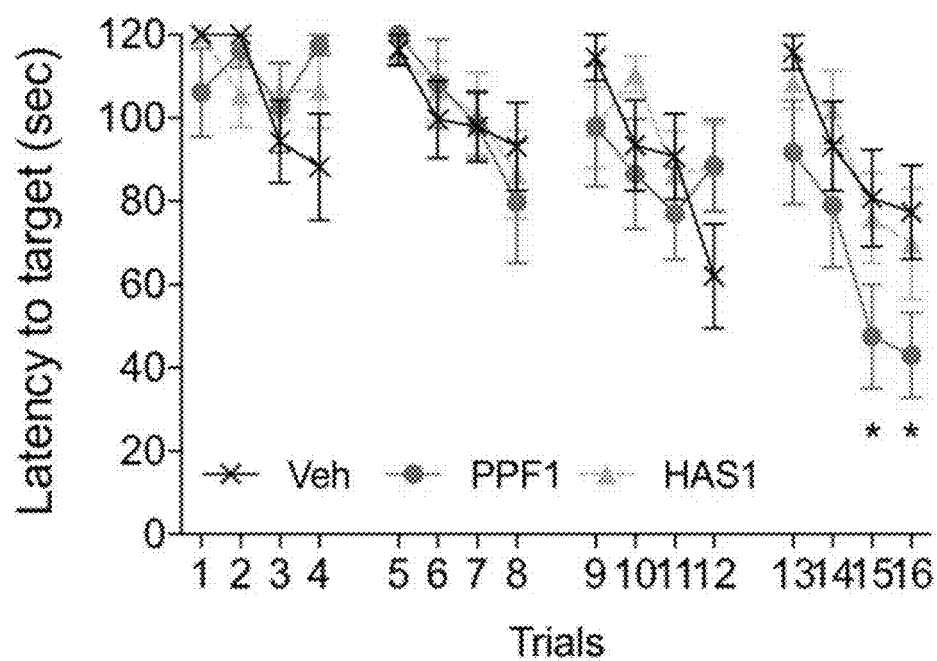
FIG. 49 reports Barnes maze escape latency in 12-month-old NSG mice treated with a seven-consecutive day Pulsed Dosing regimen using PPF1, HAS1, or vehicle control.

FIG. 49 reports Barnes Maze escape latency for a mouse to enter the escape hole for PPF1, HAS1, and vehicle-treated mice. PPF1 treated animals found the escape hole significantly faster than vehicle-treated animals. This data shows that PPF1 efficiently enhances cognition in aged NSG animals, while HAS1 treatment has no effect on hippocampal-dependent memory. All data shown are mean±s.e.m. (* P<0.05 by unpaired t-test).

v. Example 22

Clinical Paradigms Using PPF.
(1) Mild-to-Moderate AD.
Men and women 60 years or older with mild-to-moderate AD are randomly allocated to receive 100 mL or 250 mL once daily of PPF1 for 5 days ("pulsed dosing") during weeks 1 and 13 of the study with a total duration of 6 months. During the two 5-day dosing periods, subjects reside in inpatient observation units to facilitate safety evaluation, and all subjects undergo a screening visit, baseline visit, treatment visits, follow-up visits, and an end of study/early termination visit. Safety and tolerability assessments occur at every visit. Neurocognitive and motor assessments are performed at baseline and at periodic interim visits following dosing.

Primary endpoints are safety, tolerability, and feasibility of each dosing regimen. Safety is measured by the incidence of treatment-emergent adverse events. Tolerability is measured by the number of subjects completing 8 weeks after receiving at least 5 infusions and subject completing 24 weeks after receiving at least 10 infusions. Study feasibility is measured by the number of subjects completing 5 and 10 infusions. Secondary endpoints assess potential effects on cognition using various established cognitive measures including the Alzheimer's Disease Assessment Scale-Cognitive Subscale. Exploratory endpoints include assessment of changes in composition and distribution of blood-based biomarkers, as well as changes in magnetic resonance imaging.

(2) Mild-to-Moderate AD.

Two groups of subjects diagnosed with mild to moderate AD are randomized to active treatment in a double-blind manner. All subjects receive one infusion per day at the randomized dose for 5 consecutive days during weeks 1 and 13 with a study duration totaling 6 months. Subjects are randomized to one of the following two dose levels: 100 mL and 250 mL of PPF1. Dosing groups are also stratified by gender. Administration duration is 2-2.5 hours, and flow rates titrated according to dose-specific guidelines so that the entire dose is administered.

Subjects participate in optional CSF biomarker research. Such subjects undergo two lumbar punctures for CSF collection, the first prior to initial dosing, and the second following final dosing. Neurocognitive and motor assessments are performed at baseline and periodic interim assessments performed following dosing.

Safety, tolerability, and feasibility of each dosing regimen are determined. Cognitive scores are determined and summarized over the study, including: Mini-Mental State Examination (MMSE); 11-item Alzheimer's Disease Assessment Scale-Cognitive Subscale (ADAS-Cog/11); Grooved Pegboard Test; Category Fluency Test (CFT); Clinical Dementia Rating Scale-Sum of Boxes (CDR-SOB); Alzheimer's Disease Cooperative Study-Activities of Daily Living (ADCS-ADL); Alzheimer's Disease Cooperative Study-Clinical Global Impression of Change (ADCS-CGIC); Neuropsychiatric Inventory Questionnaire (NPI-Q); and Savonix Neurocognitive Assessments and Digit Span.

(3) Parkinson's Disease.

Subjects with Parkinson's Disease and cognitive impairment are randomized to two groups: 2 periods of active treatment and placebo. Subjects receive one infusion per day of active or placebo treatment for 5 consecutive days ("pulsed dosing") during the study's first week. During week 13, both groups receive active treatment for 5 consecutive days, and the study duration is approximately 7 months. Administration duration is 2-2.5 hours, and flow rates titrated according to dose-specific guidelines so that the entire dose is administered.

Safety, tolerability, and feasibility of each dosing regimen are determined. Cognitive and motor function are summarized over the study, including: MoCA; Continuity and Power of Attention, Working Memory, and Episodic Memory on the CDR-CCB; MDS-UPDRS3; MDS-UPDRS2; SE-ADL, and CISI-PD.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof.

Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A method of treating a subject diagnosed with a cognitive impairment, the method comprising, administering an effective amount of a Plasma Fraction using a Pulse Dosed dosing regimen, wherein the Plasma Fraction is a Plasma Protein Fraction comprising between 83% to 95% albumin.

2. The method of claim 1 wherein the Plasma Protein Fraction is a commercially available Plasma Protein Fraction.

3. The method of claim 1 wherein the Plasma Fraction is derived from plasma from a pool of young individuals.

4. The method of claim 1 wherein the Plasma Fraction is produced from a mammalian blood product.

5. The method of claim 4 wherein the mammalian blood product is a human blood product.

6. The method of claim 1 further comprising monitoring the subject for improved cognitive function.

7. The method of claim 1 wherein the subject is a mammal.

8. The method of any claim 7 wherein the mammal is a human.

9. The method of claim 1 wherein the Pulse Dosed dosing regimen comprises administering the Plasma Fraction for five to seven consecutive days.

10. The method of claim 1 wherein the subject follows an exercise regimen after the Pulsed Dosed dosing regimen has been fully administered.

* * * * *